(12) United States Patent
Woloszko et al.

(10) Patent No.: US 7,297,145 B2
(45) Date of Patent: *Nov. 20, 2007

(54) BIPOLAR ELECTROSURGICAL CLAMP FOR REMOVING AND MODIFYING TISSUE

(75) Inventors: Jean Woloszko, Austin, TX (US); Craig Tsuji, San Jose, CA (US); Theodore Ormsby, Escondido, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/248,460

(22) Filed: Oct. 11, 2005

(65) Prior Publication Data

US 2006/0129145 A1    Jun. 15, 2006

Related U.S. Application Data

(63) Continuation of application No. 09/839,427, filed on Apr. 20, 2001, now Pat. No. 6,974,453.

(51) Int. Cl.
*A61B 18/14* (2006.01)
(52) U.S. Cl. .............................. 606/41; 606/48; 606/50
(58) Field of Classification Search .................. 606/41, 606/48, 50–52
See application file for complete search history.

(56) References Cited

U.S. PATENT DOCUMENTS

| | | | |
|---|---|---|---|
| 2,056,377 A | 10/1936 | Wappler | 125/303 |
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |

(Continued)

FOREIGN PATENT DOCUMENTS

DE          3930451 A1      3/1991

(Continued)

OTHER PUBLICATIONS

PCT International Search Report for PCT/US04/03614, 1 page, mailed Sep. 14, 2004.

(Continued)

*Primary Examiner*—Lee S. Cohen
(74) *Attorney, Agent, or Firm*—Brian E. Szymczak

(57) ABSTRACT

The present invention provides systems, apparatus and methods for selectively applying electrical energy to body tissue in order to ablate, contract, coagulate, or otherwise modify a target tissue or organ. The closed configuration is adapted for clamping and coagulating a target tissue while the apparatus is operating in the sub-ablation mode, while the open configuration is adapted for ablating the target tissue via molecular dissociation of tissue components. A method of the present invention comprises clamping a target tissue or organ with an electrosurgical probe. A first high frequency voltage is applied between the active electrode and the return electrode to effect coagulation of the clamped tissue. Thereafter, a second high frequency voltage is applied to effect localized molecular dissociation of the coagulated tissue.

21 Claims, 54 Drawing Sheets

U.S. PATENT DOCUMENTS

| | | | |
|---|---|---|---|
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,807 A | 11/1988 | Blanch | 606/45 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 606/41 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 600/439 |
| 4,936,301 A | 6/1990 | Rexroth et al. | 606/45 |
| 4,943,290 A | 7/1990 | Rexroth et al. | 606/45 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble et al. | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,190,541 A | 3/1993 | Abele et al. | 606/46 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,197,964 A | 3/1993 | Parins | 606/48 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,217,460 A | 6/1993 | Knoepfler | 606/52 |
| 5,261,410 A | 11/1993 | Alfano et al. | 600/475 |
| 5,261,905 A | 11/1993 | Doresey | 606/45 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,584,872 A | 12/1996 | LaFontaine et al. | 607/117 |
| 5,609,151 A | 3/1997 | Mulier et al. | 128/642 |
| 5,633,578 A | 5/1997 | Eggers | 323/301 |
| 5,647,869 A | 7/1997 | Goble et al. | 606/37 |
| 5,662,680 A | 9/1997 | Desai | 606/210 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,702,390 A | 12/1997 | Austin et al. | 606/48 |
| 5,725,524 A | 3/1998 | Mulier et al. | 606/41 |
| 5,766,153 A | 6/1998 | Eggers et al. | 604/114 |
| 5,807,392 A | 9/1998 | Eggers | 606/31 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,836,875 A | 11/1998 | Webster, Jr. | 600/374 |

| Patent No. | Date | Inventor | Class |
|---|---|---|---|
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,893,849 A | 4/1999 | Weaver | 606/41 |
| 5,897,553 A | 4/1999 | Mulier et al. | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,063,083 A | 5/2000 | Duong-Yan | 606/45 |
| 6,066,134 A | 5/2000 | Eggers et al. | 606/32 |
| 6,066,137 A | 5/2000 | Greep | 606/45 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,093,186 A | 7/2000 | Goble | 606/34 |
| 6,096,037 A * | 8/2000 | Mulier et al. | 606/49 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,214,001 B1 | 4/2001 | Casscells et al. | 606/41 |
| 6,217,575 B1 | 4/2001 | DeVore et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,261,286 B1 | 7/2001 | Goble et al. | 606/34 |
| 6,264,652 B1 | 7/2001 | Eggers et al. | 606/41 |
| 6,270,460 B1 | 8/2001 | McCartan et al. | 600/459 |
| 6,273,887 B1 | 8/2001 | Yamauchi et al. | 606/48 |
| 6,277,112 B1 | 8/2001 | Underwood et al. | 606/32 |
| 6,280,441 B1 | 8/2001 | Ryan | 606/45 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,427,089 B1 | 7/2002 | Knowlton | 607/101 |
| 6,432,103 B1 | 8/2002 | Ellsberry et al. | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,517,498 B1 | 2/2003 | Burbank et al. | 600/564 |
| 6,530,922 B2 | 3/2003 | Cosman et al. | 606/34 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,749,608 B2 | 6/2004 | Garito et al. | 606/45 |
| 6,780,178 B2 | 8/2004 | Palanker et al. | 600/41 |
| 6,780,180 B1 | 8/2004 | Goble et al. | 606/41 |
| 6,790,217 B2 | 9/2004 | Schulze et al. | 606/171 |
| 6,802,842 B2 | 10/2004 | Ellman et al. | 606/45 |
| 6,808,525 B2 | 10/2004 | Latterell et al. | 606/42 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 2003/0013986 A1 | 1/2003 | Saadat | 600/549 |

FOREIGN PATENT DOCUMENTS

| | | |
|---|---|---|
| EP | 0703461 A2 | 3/1996 |
| EP | 0740926 A2 | 11/1996 |
| EP | 0 754 437 | 1/1997 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| WO | 90/03152 | 4/1990 |
| WO | 90/07303 | 7/1990 |
| WO | 92/21278 | 12/1992 |
| WO | 97/13816 | 7/1993 |
| WO | 93/20747 | 10/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/24073 | 7/1997 |
| WO | 97/24074 | 7/1997 |
| WO | 97/24993 | 7/1997 |
| WO | 97/24994 | 7/1997 |

| WO | 97/48345 | 12/1997 |
| WO | 97/48346 | 12/1997 |
| WO | 98/07468 | 2/1998 |
| WO | 98/27879 | 7/1998 |
| WO | 98/27880 | 7/1998 |
| WO | 99/51155 | 10/1999 |
| WO | 99/51158 | 10/1999 |
| WO | 01/87154 | 5/2001 |
| WO | 02/36028 | 5/2002 |

OTHER PUBLICATIONS

Pearce, John A. "Electrosurgery", pp. 17, 69-75, 87, John Wiley & Sons, New York, 1986.
J.W. Ramsey et al., "A Comparison of Bipolar and Monopolar Diathermy Probes in Experimental Animals", *Urological Research* vol. 13, pp. 99-102, 1985.
V.E. Elsasser et al., "An Instrument for Transurethral Resection without Leakage of Current" *Acta Medicotechnica* vol. 24, No. 4, pp. 129-134, 1976.
P.C. Nardella *SPIE* 1068:42-49 Radio Frequency Energy and Impedance Feedback, 1989.
R. Tucker et al., Abstract p. 14-11, p. 248, "A Bipolar Electrosurgical Turp Loop", Nov. 1989.
R. Tucker et al. "A Comparison of Urologic Application of Bipolar Versus Monopolar Five French Electrosurgical Probes" *J. of Urology* vol. 141, pp. 662-665, 1989.
R. Tucker et al. "In vivo effect of 5 French Bipolar and Monopolar Electrosurgical Probes on the Porcine Bladder" *Urological Research* vol. 18, pp. 291-294, 1990.
Kramolowsky et al. "Use of 5F Bipolar Electrosurgical Probe in Endoscopic Urological Procedures" *J. of Urology* vol. 143, pp. 275-277, 1990.
Kramolowsky et al. "The Urological App of Electrosurgery" *J. of Urology* vol. 146, pp. 669-674, 1991.
Slager et al. "Spark Erosion of Arteriosclerotic Plaques" *Z. Kardiol.* 76:Suppl. 6, 67-71, 1987.
Slager et al. "Vaporization of Atherosclerotice Plaques by Spark Erosion" *JACC* 5(6):1382-6, Jun. 1985.
Olsen MD, Bipolar Laparoscopic Cholecstectomy Lecture (marked confidential), 12 pgs, Oct. 7, 1991.
Codman & Shurtleff, Inc. "The Malis Bipolar Electrosurgical System CMC-III Instruction Manual", 15 pgs, Jul. 1991.
Valley Forge's New Products, CLINICA, 475, 5, Nov. 6, 1991.
Valley Forge Scientific Corp., "Summary of Safety and Effective Information form 510K", 2pgs, 1991.
Codman & Shurtleff, Inc. "The Malis Bipolar Coagulating and Bipolar Cutting System CMC-II" brochure, early, 2pgs, 1991.
L. Malis, "The Value of Irrigation During Bipolar Coagulation" See ARTC 21602, 1 pg, Apr. 9, 1993.
L. Malis, "Excerpted from a seminar by Leonard I. Malis, M.D. at the 1995 American Association of Neurological Surgeons Meeting," 1pg, 1995.
L. Malis, "Electrosurgery, Technical Note," *J. Neursurg.*, vol. 85, 970-975, Nov. 1996.
Ian E. Shuman, "Bipolar Versus Monopolar Electrosurgery: Clinical Applications," *Dentistry Today*, vol. 20, No. 12, 7 pgs, Dec. 2001.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Cook et al., "Therapeutic Medical Devices: Application and Design", Prentice Hall, Inc., 3pgs, 1982.
Valleylab SSE2L Instruction Manual, 11 pgs, Jan. 6, 1983.
Robert D. Tucker et al., "Demodulated Low Frequency Currents from Electrosurgical Procedures," *Surgery, Gynecology and Obstetrics*, 159:39-43, 1984
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Selikowitz et al., "Electric Current and Voltage Recordings on the Myocardium During Electrosurgical Procedures in Canines," *Surgery, Gynecology & Obstetrics*, vol. 164, 219-224, Mar. 1987.
J. O'Malley, Schaum's Outline of Theory and Problems of Basic Circuit Analysis, McGraw-Hill, $2^{nd}$ Ed., pp. 3-5, 1992.
Arnaud Wattiez et al., "Electrosurgery in Operative Endoscopy," Electrosurgical Effects, Blackwell Science, pp. 85-93, 1995.
Leslie A. Geddes, "Medical Device Accidents: With Illustrative Cases" CRC Press, 3 pgs, 1998.
Wyeth, "Electrosurgical Unit" pp. 1181-1202.
C.P. Swain, et al., "Which Electrode, A Comparison of four endoscopic methods of electrocoagulation in experimental bleeding ulcers" *Gut* vol. 25, pp. 1424-1431, 1987.
Piercey et al., "Electrosurgical Treatment of Experimental Bleeding Canine Gastric Ulcers" *Gastroenterology* vol. 74(3), pp. 527-534, 1978.
A.K. Dobbie, "The Electrical Aspects of Surgical Diathermy, Bio Medical Engineering" *Bio-Medical Engineering* vol. 4, pp. 206-216, May 1969.
B. Lee et al. "Thermal Compression and Molding of Artheroscleotic Vascular Tissue with Use" *JACC* vol. 13(5), pp. 1167-1171, 1989.
K. Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
W. Honig, "The Mechanism of Cutting in Electrosurgery" *IEEE* pp. 58-65, 1975.
Pearce, John C., "Electrosurgery", Handbook of Biomedical Engineering, chapter 3, Academic Press Inc., N.Y., pp. 98-113, 1988.
M.B. Dennis et al. "Evolution of Electrofulguration in Control of Bleeding of Experimental Gastric Ulcers," Digestive Diseases and Sciences, vol. 24, No. 11, 845-848, Nov. 1979.
Letter from Department of Health to Jerry Malis dated Jul. 25, 1985, 1 pg.
Letter from Jerry Malis to FDA dated Jul. 25, 1985, 2 pgs.
Letter from Department of Health to Jerry Malis dated Jan. 24, 1991, 3 pgs.
Leonard Malis, "Instrumentation for Microvascular Neurosurgery" *Cerebrovascular Surgery*, vol. 1, 245-260, 1985.
Valleylab, Inc. "Valleylab Part No. 945 100 102 A" Surgistat Service Manual, pp. 1-46, Jul. 1988.
Leonard I. Malis, "New Trends in Microsurgery and Applied Technology," *Advanced Technology in Neurosurgery*, 1-16, 1988.
Wyeth, "Electrosurgical Unit" pp. 1181-1202, 1985.

* cited by examiner

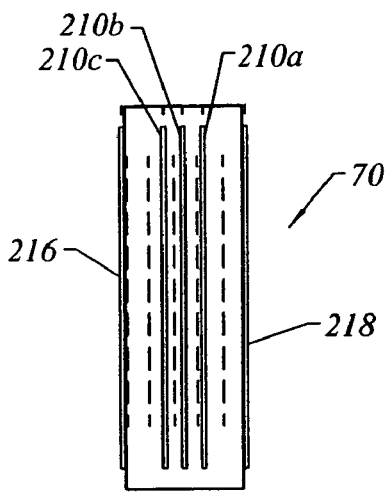
FIG. 6
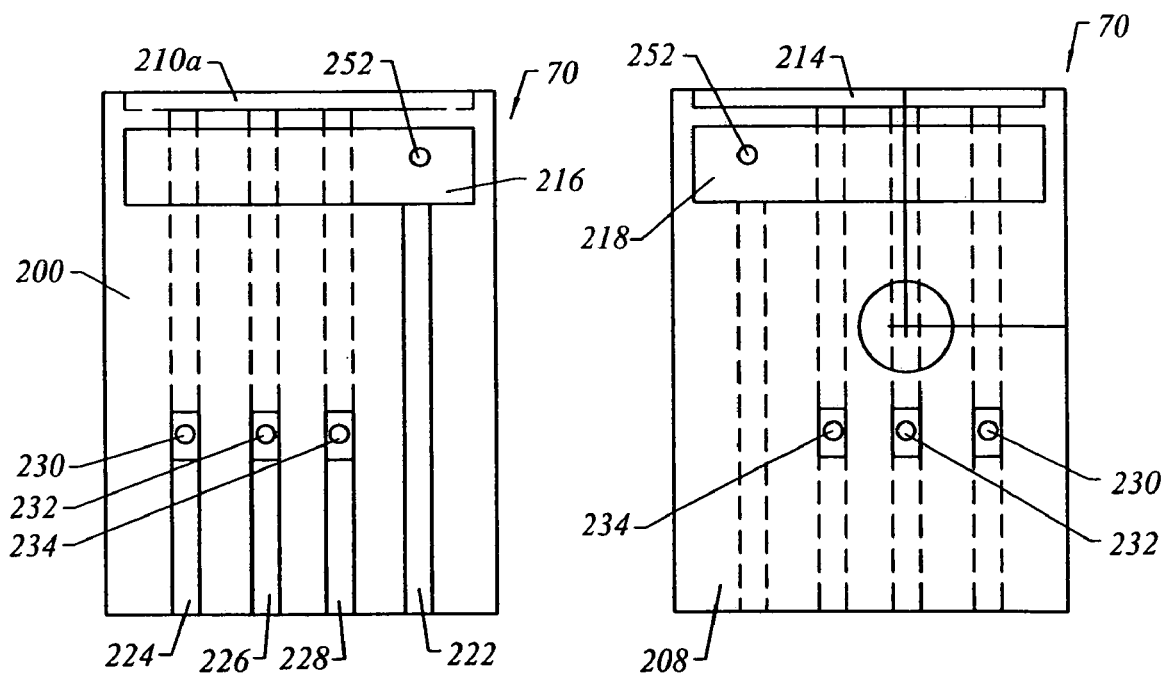
FIG. 7
FIG. 8

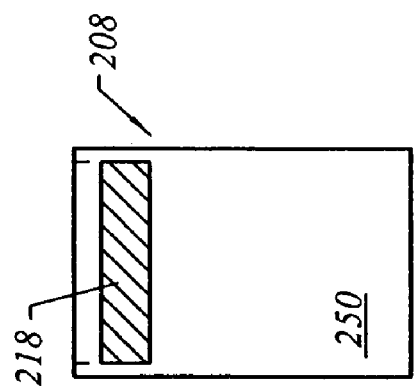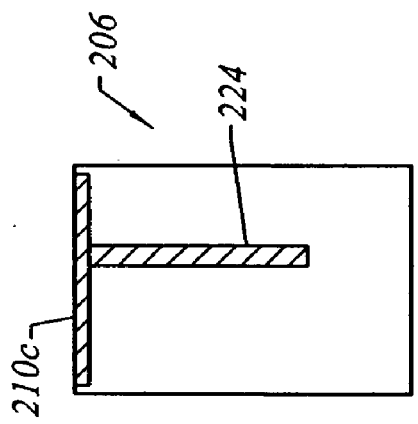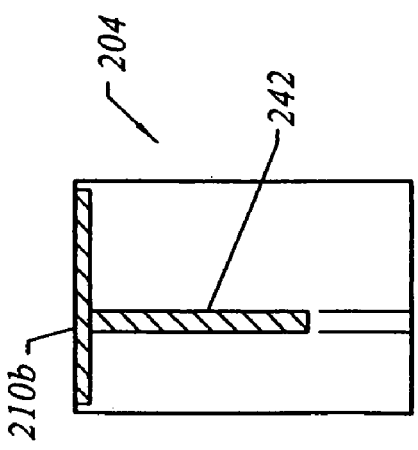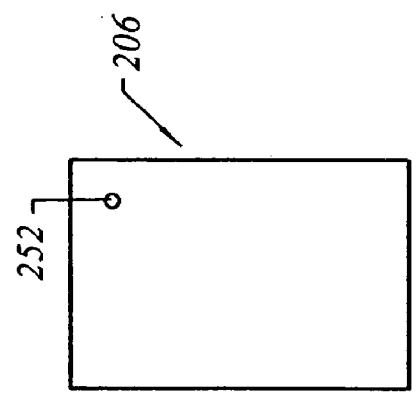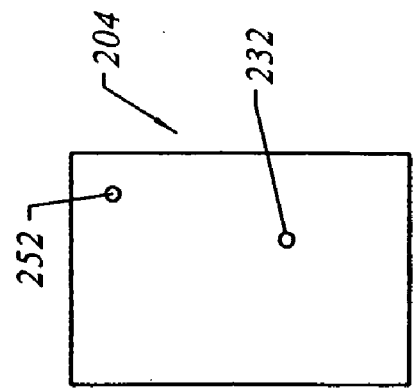

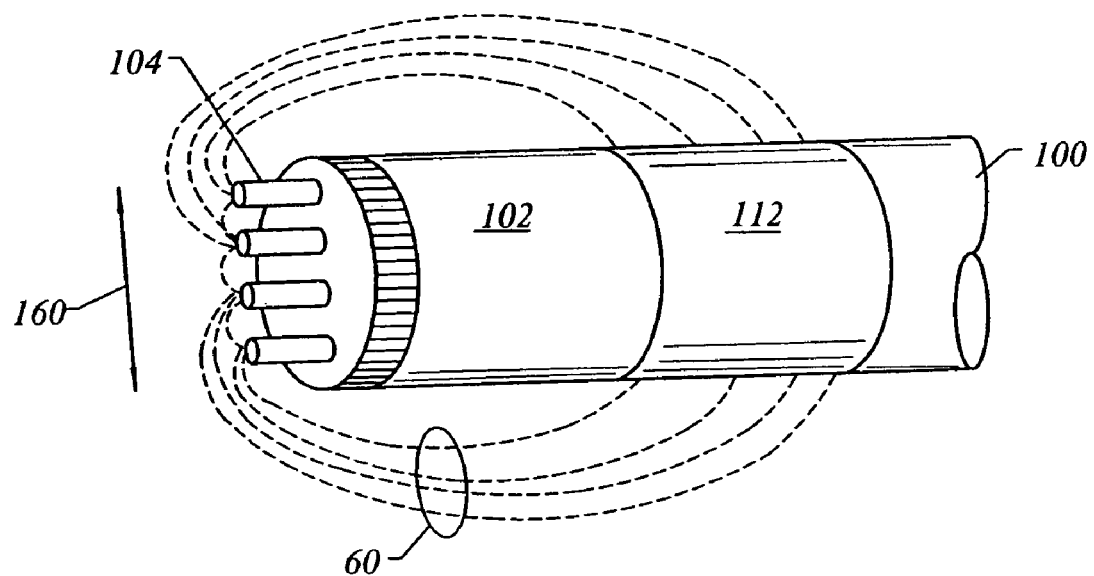
FIG. 21
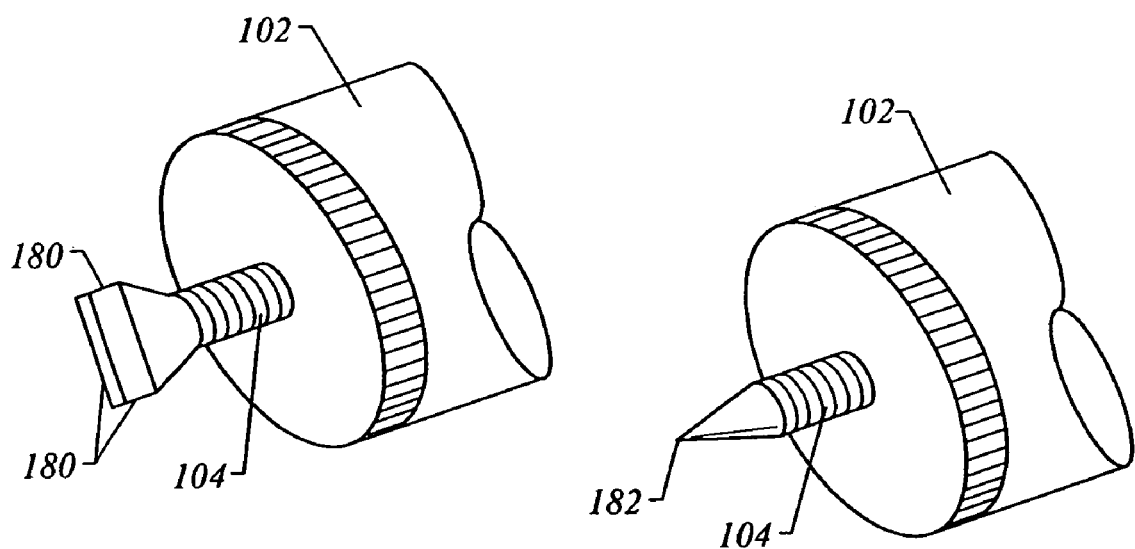
FIG. 22
FIG. 23

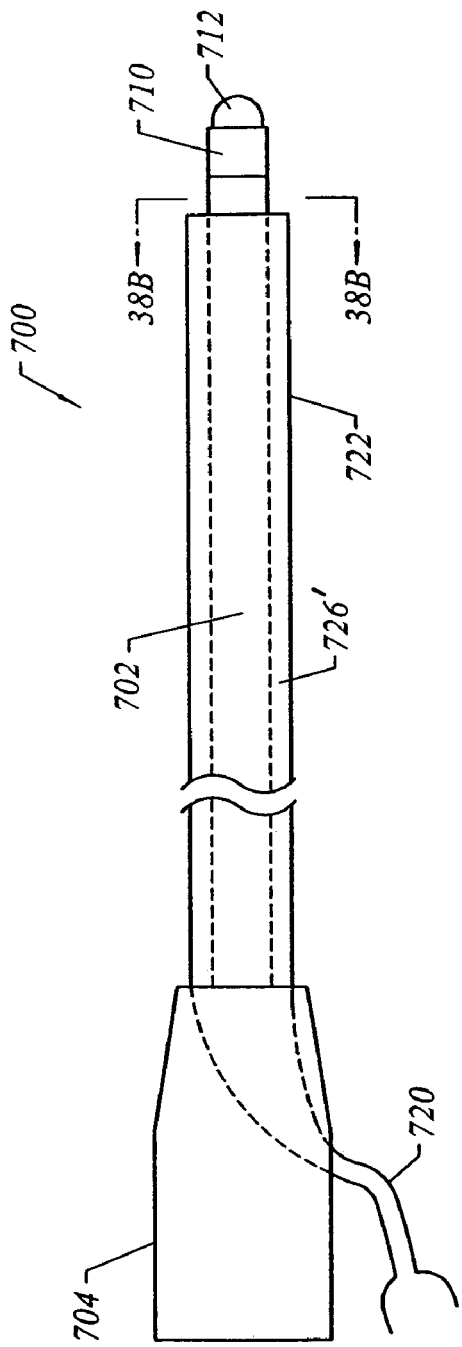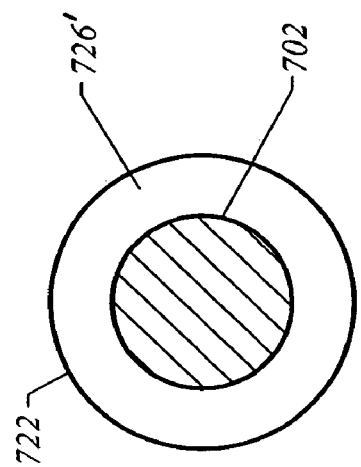
FIG. 38A
FIG. 38B

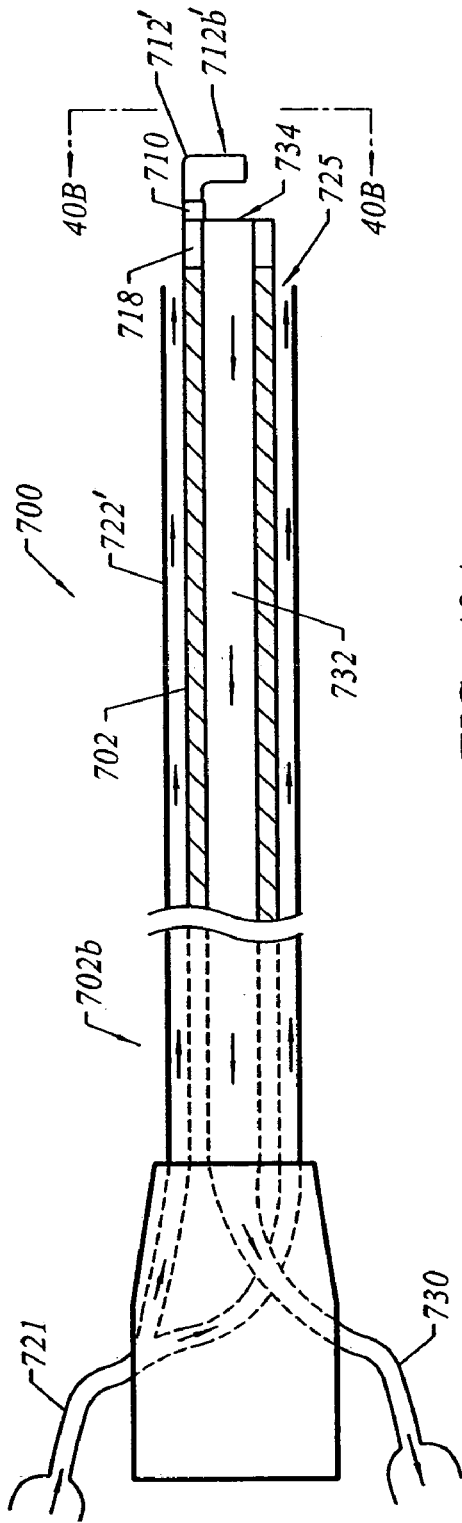
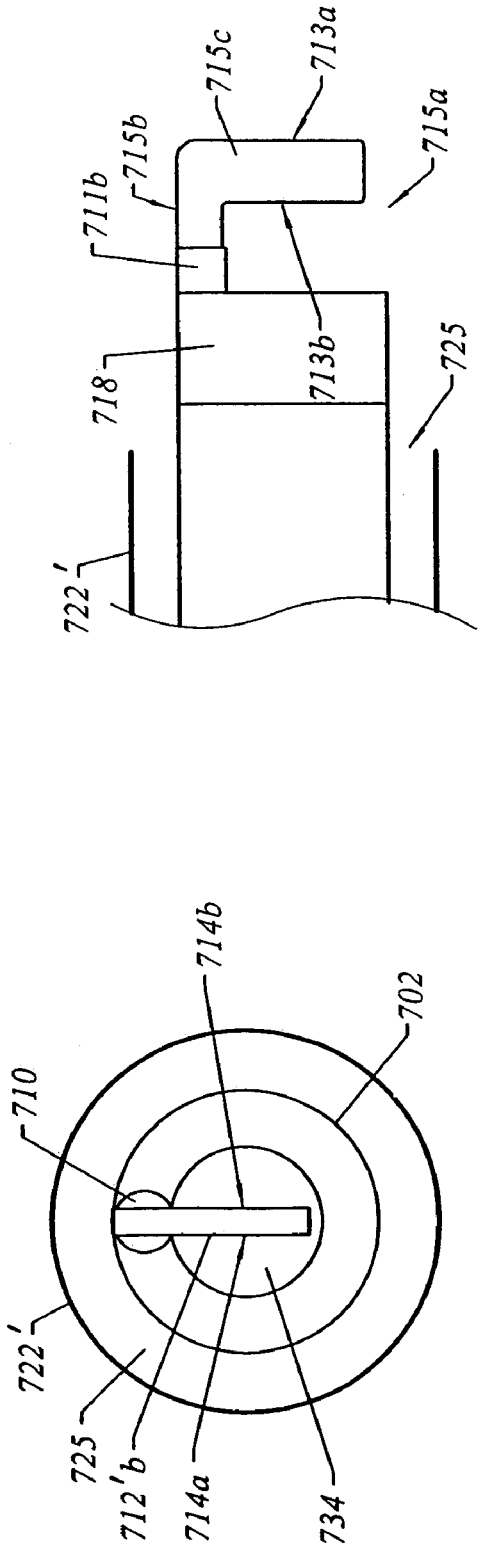
FIG. 40A
FIG. 40B
FIG. 40C

BIPOLAR ELECTROSURGICAL CLAMP FOR REMOVING AND MODIFYING TISSUE

CROSS-REFERENCES TO RELATED APPLICATIONS

The present application is a continuation of U.S. patent application Ser. No. 09/839,427 filed Apr. 20, 2001 now U.S. Pat. No. 6,974,453, which is a continuation-in-part of U.S. patent application Ser.No. 09/780,745 filed Feb. 9, 2001, now U.S. Patent No. 6,770,071 the complete disclosures of which are incorporated herein by reference for all purposes.

The present invention is also related to commonly assigned U.S. Provisional Patent Application No. 60/062,996, filed Oct. 23, 1997, U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively) and U.S. patent application Ser. No. 09/054,323, filed on Apr. 2, 1998, U.S. patent application Ser. No. 09/010,382, filed Jan. 21, 1998, and U.S. patent application Ser. No. 09/032,375, filed Feb. 27, 1998, U.S. patent application Ser. No. 08/977,845, filed on Nov. 25, 1997, Ser. No. 08/942,580, filed on Oct. 2, 1997, U.S. application Ser. No. 08/753,227, filed on Nov. 22, 1996, U.S. application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention generally relates to electrosurgical systems and methods for ablating, severing, contracting, or otherwise modifying target tissues or organs. The invention relates more particularly to electrosurgical apparatus and methods for coagulating a tissue or organ and for ablating the coagulated tissue or organ via molecular dissociation of tissue components. The present invention further relates to electrosurgical methods and apparatus for clamping a target tissue or blood vessel prior to coagulating and severing the tissue or blood vessel.

Conventional electrosurgical instruments and techniques are widely used in surgical procedures because they generally reduce patient bleeding and trauma associated with cutting operations, as compared with mechanical cutting and the like. Conventional electrosurgical procedures may be classified as operating in monopolar or bipolar mode. Monopolar techniques rely on external grounding of the patient, where the surgical device defines only a single electrode pole. Bipolar devices have two electrodes for the application of current between their surfaces. Conventional electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and the tissue. At the point of contact of the electric arcs with the tissue, rapid tissue heating occurs due to high current density between the electrode and the tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue.

Further, monopolar electrosurgical devices generally direct electric current along a defined path from the exposed or active electrode through the patient's body to the return electrode, the latter externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high electrical impedance, large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue.

Bipolar electrosurgical devices have an inherent advantage over monopolar devices because the return current path does not flow through the patient. In bipolar electrosurgical devices, both the active and return electrode are typically exposed so that both electrodes may contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

In addition, conventional electrosurgical methods are generally ineffective for ablating certain types of tissue, and in certain types of environments within the body. For example, loose or elastic connective tissue, such as the synovial tissue in joints, is extremely difficult (if not impossible) to remove with conventional electrosurgical instruments because the flexible tissue tends to move away from the instrument when it is brought against this tissue. Since conventional techniques rely mainly on conducting current through the tissue, they are not effective when the instrument cannot be brought adjacent to, or in contact with, the elastic tissue for a sufficient period of time to energize the electrode and conduct current through the tissue.

There is a need for a general-purpose electrosurgical apparatus adapted for the precise removal or modification of a target tissue or organ at a specific location, wherein the target tissue or organ can be ablated, severed, resected, contracted, and/or coagulated, with minimal, or no, collateral tissue damage. The instant invention provides such an apparatus and related methods, wherein the apparatus includes at least one moveable electrode, and at least a portion of the target tissue or organ may be clamped between an active electrode and a return electrode prior to coagulation of the tissue or organ. Following coagulation, the coagulated tissue or organ may be ablated or severed.

SUMMARY OF THE INVENTION

The present invention generally provides systems, apparatus, and methods for selectively applying electrical energy to cut, incise, ablate, or otherwise modify a tissue or organ of a patient. In one aspect, the electrosurgical systems and methods of the invention are useful for resecting a tissue or organ having a plurality of blood vessels running therethrough, wherein, using a single probe, each blood vessel encountered during resection of the tissue or organ may be clamped, coagulated, and then severed.

In one aspect, the present invention provides a method of creating an incision in a body structure. An electrosurgical probe is positioned adjacent the target tissue so that one or more active electrode(s) are brought into at least partial contact or close proximity with the target tissue. High frequency voltage is then applied between the active electrode(s) and one or more return electrode(s) and the active electrode(s) are moved, translated, reciprocated, or otherwise manipulated to cut through a portion of the tissue. In some embodiments, an electrically conductive fluid, e.g., isotonic saline or conductive gel, is delivered or applied to the target site to substantially surround the active electrode(s) with the fluid. In other embodiments, the active electrode(s) are immersed within the electrically conductive fluid. In both embodiments, the high frequency voltage may be selected to locally ablate or sever a target tissue, and/or to effect a controlled depth of hemostasis of severed blood vessels within the tissue.

In one aspect, tissue is cut or otherwise modified by molecular dissociation or disintegration processes. (In contrast, in conventional electrosurgery tissue is cut by rapidly heating the tissue until cellular fluids explode, producing a cutting effect along the pathway of localized heating.) The present invention volumetrically removes the tissue along the cutting pathway in a cool ablation process that minimizes thermal damage to surrounding tissue. In these embodiments, the high frequency voltage applied to the active electrode(s) is sufficient to vaporize the electrically conductive fluid (e.g., gel or saline) between the active electrode(s) and the tissue. Within the vaporized fluid, a plasma is formed and charged particles (e.g., electrons) cause the molecular breakdown or disintegration of the tissue, perhaps to a depth of several cell layers. This molecular dissociation is accompanied by the volumetric removal of the tissue, e.g., along the incision of the tissue. This process can be precisely controlled to effect the volumetric removal of tissue as thin as 10 microns to 150 microns with minimal heating of, or damage to, surrounding or underlying tissue structures. A more complete description of this phenomenon is described in commonly assigned U.S. Pat. No. 5,683,366, the complete disclosure of which is incorporated herein by reference.

Apparatus according to the present invention generally include an electrosurgical instrument, such as a probe or catheter, having a shaft with proximal and distal ends, one or more active electrode(s) at the distal end and one or more connectors coupling the active electrode(s) to a source of high frequency electrical energy. The active electrode(s) are preferably designed for cutting tissue; i.e., they typically have a distal edge or point. In one embodiment, a plurality of active electrodes are aligned with each other to form a linear electrode array for cutting a path through the tissue. In another exemplary embodiment, the active electrode(s) include a sharp distal point to facilitate the cutting of the target tissue. In one specific configuration, the active electrode is a blade having a sharp distal point and sides. As the sharp distal point incises the tissue, the sides of the blade slidingly contact the incised tissue. The electrical current flows through that portion of the tissue in the vicinity of the active electrode and/or the conductive fluid to the return electrode, such that the target tissue is first severed, and then the severed tissue is coagulated.

The apparatus can further include a fluid delivery element for delivering electrically conductive fluid to the active electrode(s) and the target site. The fluid delivery element may be located on the probe, e.g., a fluid lumen or tube, or it may be part of a separate instrument. Alternatively, an electrically conductive gel or spray, such as a saline electrolyte or other conductive gel, may be applied the target site. In this embodiment, the apparatus may not have a fluid delivery element. In both embodiments, the electrically conductive fluid preferably provides a current flow path between the active electrode(s) and one or more return electrode(s). In an exemplary embodiment, the return electrode is located on the probe and spaced a sufficient distance from the active electrode(s) to substantially avoid or minimize current shorting therebetween and to shield the return electrode from tissue at the target site.

In a specific configuration, the electrosurgical probe includes an electrically insulating electrode support member having a tissue treatment surface at the distal end of the probe. One or more active electrode(s) are coupled to, or integral with, the electrode support member such that the active electrode(s) are spaced from the return electrode. In one embodiment, the probe includes a plurality of active electrode(s) having distal edges linearly aligned with each other to form a sharp cutting path for cutting tissue. The active electrodes are preferably electrically isolated from each other, and they extend about 0.2 mm to about 10 mm distally from the tissue treatment surface of the electrode support member. In this embodiment, the probe may further include one or more lumens for delivering electrically conductive fluid to one or more openings around the tissue treatment surface of the electrode support member. In an exemplary embodiment, the lumen extends through a fluid tube exterior to the probe shaft that ends proximal to the return electrode.

In another aspect of the invention, there is provided an electrosurgical probe having a blade-like active electrode affixed to an electrically insulating electrode support on the distal end of a shaft. In a specific configuration, the active electrode is in the form of a blade, comprising a substantially flat metal blade having at least one active edge and first and second blade sides. In one embodiment, the active electrode comprises a hook. The hook may include a curved portion. One or more portions of the hook may have a serrated edge. The return electrode is typically located on the shaft distal end proximal to the electrode support. In use, the active electrode and the return electrode are coupled to opposite poles of a high frequency power supply. The active edge may have a variety of shapes, and is adapted for generating high current densities thereon, and for precisely severing or ablating tissue or an organ in a highly controlled manner via molecular dissociation of tissue components. The first and second blade sides are adapted for engaging with tissue, such as tissue severed by the active edge, and for coagulating tissue engaged therewith.

According to one aspect of the invention, there is provided a method for modifying a tissue using an electrosurgical probe having an active electrode in the form of a single blade which includes at least one active edge and first and second blade sides. The method involves positioning the probe such that the active electrode makes contact with, or is in close proximity to, a target tissue; and applying a high frequency voltage between the active and return electrodes sufficient to precisely sever or remove target tissue via molecular dissociation of tissue components adjacent to the active edge. The probe may be manipulated during the application of the high frequency voltage such that the active electrode is moved with respect to the target tissue. According to one aspect of the invention, the configuration of the active electrode (e.g., a hook shaped electrode) is adapted for severing tissue as the probe distal end is drawn or pulled towards the operator of the probe. In this manner, the extent to which the tissue is severed can be precisely controlled. Thereafter, the severed tissue may be coagulated upon engagement of the tissue against the first and second blade sides of the active electrode.

According to one aspect of the invention, there is provided an electrosurgical system including a probe having a shaft distal end. An active electrode and a return electrode are disposed at the shaft distal end. At least one of the active electrode and the return electrode are moveable, such that the probe can adopt an open configuration or a closed configuration. In the open configuration, a target tissue or organ may be positioned between the active and return electrodes, and thereafter the probe may be urged towards the closed configuration such that the target tissue or organ is effectively clamped between the active and return electrodes. While the target tissue or organ is thus clamped, a suitable high frequency voltage may be applied between the active and return electrodes so as to coagulate the tissue or organ. Thereafter, the coagulated tissue or organ may be unclamped or released by forcing the probe towards the open configuration. With the target tissue or organ in at least close proximity to the active electrode, a second high frequency voltage may be applied between the active and return electrodes so as to ablate or sever the coagulated tissue or organ via localized molecular dissociation of tissue components.

In one embodiment, the probe is shifted between the open and closed configurations via an actuator unit including at least one of a clamp unit and a release unit. In one aspect, actuation of the actuator unit serves to switch the electrosurgical system, via a mode switch, between an ablation mode and a sub-ablation mode. In another aspect, a mode switch is responsive either to a change in configuration of the probe between the open and closed configurations, or to movement of a moveable electrode.

In another aspect, there is provided a bipolar electrosurgical clamp including a return electrode in the form of a moveable cowl or hood. In one embodiment, the cowl includes a distal notch for accommodating a portion of the active electrode which protrudes laterally from the probe. In another embodiment, the moveable cowl includes an undulating perimeter adapted for gripping a target tissue or organ. In one embodiment, the moveable cowl is pivotable about its proximal end between a closed- and an open configuration. In yet another aspect, there is provided a bipolar electrosurgical clamp including a moveable active electrode, which can be pivoted between a closed- and an open configuration.

The electrosurgical probe of the invention is applicable to a broad range of procedures, including without limitation: cutting, resection, ablation, and/or hemostasis of tissues and organs such as prostate, liver, bowel, intestine, gall bladder, uterus, tissue in laparascopic or open surgical procedures (e.g., cholecystectomy, Nissen fundoplication, bowel resection, hysterectomy, adhesiolysis and the like), scar tissue, myocardial tissue, and tissues of the knee, shoulder, hip, and other joints; procedures of the head and neck, such as of the ear, mouth, throat, pharynx, larynx, esophagus, nasal cavity, and sinuses; as well as procedures involving skin tissue removal and/or collagen shrinkage in the epidermis or dermis. A more detailed account of various treatments and procedures which may be carried out according to the invention is set forth in enabling detail hereinbelow.

For a further understanding of the nature and advantages of the invention, reference should be made to the following description taken in conjunction with the accompanying drawings.

BRIEF DESCRIPTION OF THE DRAWINGS

FIG. 6 is an end view of an exemplary electrode support comprising a multi-layer wafer with plated conductors for electrodes;

FIGS. 7 and 8 are side views of the electrode support of FIG. 6;

FIGS. 9A-12A are side views of the individual wafer layers of the electrode support;

FIGS. 9B-12B are cross-sectional views of the individual wafer layers;

FIG. 13 is a side view of an individual wafer layer;

FIG. 21 is a detailed end view of an electrosurgical probe having an elongate, linear array of active electrodes suitable for use in surgical cutting;

FIG. 22 is a detailed view of a single active electrode having a flattened end at its distal tip;

FIG. 23 is a detailed view of a single active electrode having a pointed end at its distal tip;

FIGS. 38A, and 38B are a side view and an end view, respectively, of an electrosurgical probe having an outer sheath surrounding the probe shaft, according to another embodiment of the invention;

FIGS. 40A and 40B schematically represent a longitudinal sectional view, and an end view, respectively, of an electrosurgical probe, according to another embodiment of the invention;

FIG. 40C shows detail of the distal portion of the probe of FIGS. 40A, 40B;

DESCRIPTION OF THE SPECIFIC EMBODIMENTS

Figure 1:
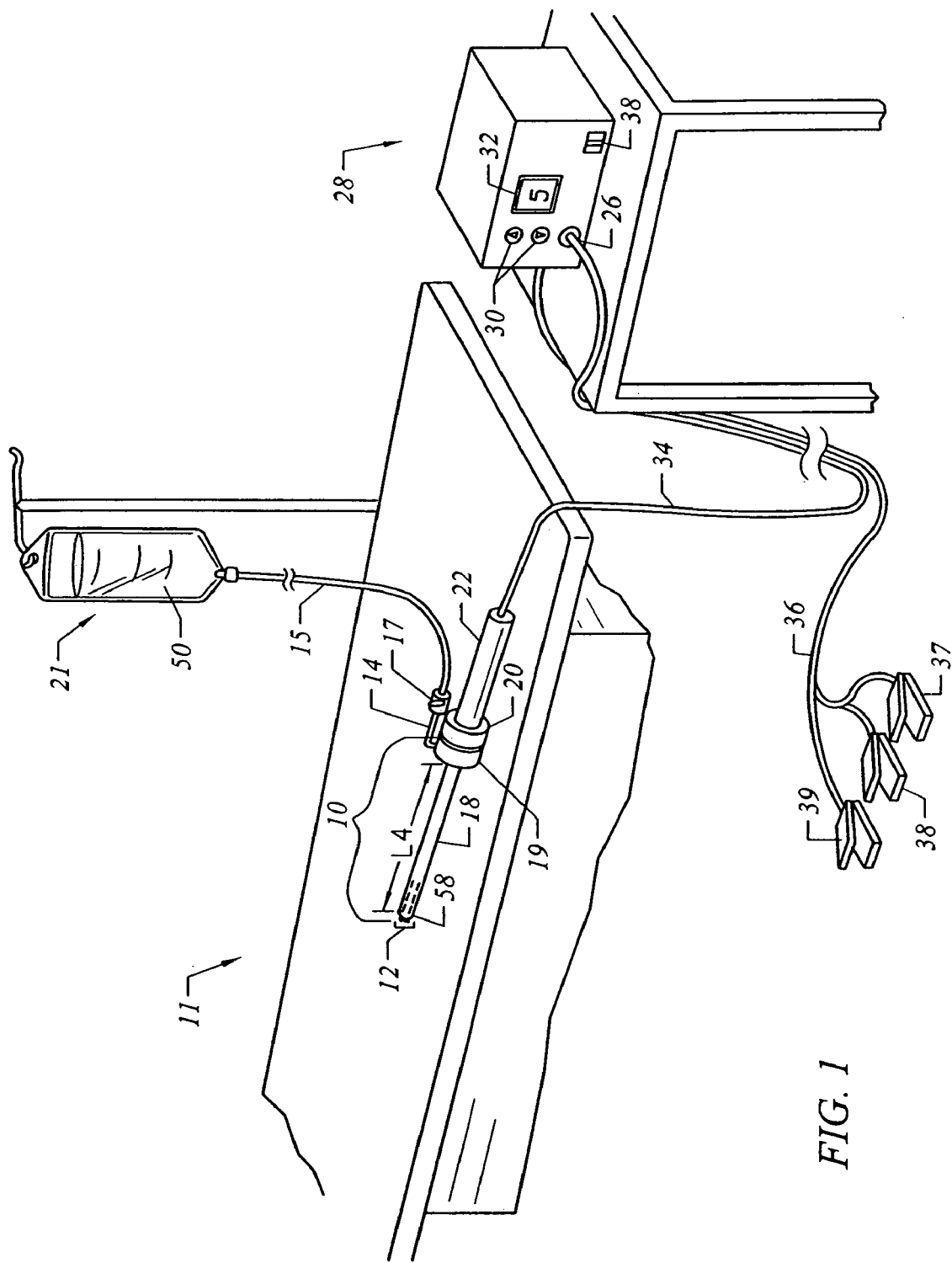
FIG. 1 is a perspective view of an electrosurgical system incorporating a power supply and an electrosurgical probe for tissue ablation, resection, incision, contraction, vessel harvesting, and hemostasis, according to the present invention.

The present invention provides systems and methods for selectively applying electrical energy to a target location within or on a patient's body, particularly for cutting, ablating, clamping, and coagulating a tissue using an electrosurgical probe. The instant invention also provides apparatus and methods for making incisions to access a tissue or organ within a patient's body, to dissect or harvest the tissue or organ from the patient, and to transect, resect, or otherwise modify the tissue or organ. The present invention is useful in procedures where the target tissue or organ is, or can be, flooded or submerged with an electrically conductive fluid, such as isotonic saline. In addition, tissues which may be treated by the system and method of the present invention further include, but are not limited to, tissues of the heart, chest, knee, shoulder, ankle, hip, elbow, hand or foot; as well as prostate tissue, leiomyomas (fibroids) located within the uterus, gingival tissues and mucosal tissues located in the mouth, tumors, scar tissue, myocardial tissue, collagenous tissue within the eye; together with epidermal and dermal tissues on the surface of the skin. The present invention is also useful for resecting tissue within accessible sites of the body that are suitable for electrode loop resection, such as the resection of prostate tissue, leiomyomas (fibroids) located within the uterus, or other tissue to be removed from the body.

The present invention is also useful for procedures in the head and neck, such as the ear, mouth, throat, pharynx, larynx, esophagus, nasal cavity, and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for cutting, resection, ablation and/or hemostasis of tissue in procedures for treating snoring and obstructive sleep apnea (e.g., UPPP procedures), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies, myringotomies, or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck region, e.g., the removal of pigmentations, vascular lesions, scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

The present invention is also useful for harvesting blood vessels, such as a blood vessel to be used as a graft vessel during the CABG procedure, e.g., the saphenous vein and the internal mammary artery (IMA). One or more embodiments of the invention may be used as follows: i) to access the blood vessel to be harvested, e.g., by opening the leg to access the saphenous vein, or opening the chest (either via a longitudinal incision of the sternum during an open-chest procedure, or during a minimally invasive inter-costal procedure); ii) to dissect the blood vessel to be harvested from the surrounding connective tissue along at least a portion of its length; and iii) to transect the dissected blood vessel at a first position only in the case of a pedicled graft (IMA), or at the first position and at a second position in the case of a free graft (saphenous vein). In each case i) to iii), as well as for other embodiment of the invention, the procedure involves removal of tissue by a cool ablation procedure in which a high frequency voltage is applied to an active electrode in the vicinity of a target tissue, typically in the presence of an electrically conductive fluid. The cool ablation procedure of the invention is described fully elsewhere herein.

The electrically conductive fluid may be a bodily fluid such as blood or synovial fluid, intracellular fluid of the target tissue, or isotonic saline delivered to the target tissue during the procedure. In one embodiment, apparatus of the invention includes a probe adapted for being shifted between an open configuration and a closed configuration. The present invention is useful for coagulating blood or blood vessels, for example, for coagulating blood vessels traversing a target tissue during incising or resecting the target tissue. The present invention is also useful for clamping a target tissue or blood vessel prior to coagulating the tissue or blood vessel, and for severing or ablating the coagulated tissue or blood vessel. Apparatus of the present invention may also be used to ablate or otherwise modify a target tissue without prior coagulation of the target tissue.

Although certain parts of this disclosure are directed specifically to creating incisions for accessing a patient's thoracic cavity and the harvesting and dissection of blood vessels within the body during a CABG procedure, systems and methods of the invention are equally applicable to other procedures involving other organs or tissues of the body, including minimally invasive procedures, other open procedures, intravascular procedures, urological procedures, laparascopy, arthroscopy, thoracoscopy or other cardiac procedures, cosmetic surgery, orthopedics, gynecology, otorhinolaryngology, spinal and neurologic procedures, oncology, and the like.

In methods of the present invention, high frequency (RF) electrical energy is usually applied to one or more active electrodes in the presence of an electrically conductive fluid to remove and/or modify target tissue, an organ, or a body structure. Depending on the specific procedure, the present invention may be used to: (1) create incisions in tissue; (2) dissect or harvest tissue; (3) volumetrically remove tissue or cartilage (i.e., ablate or effect molecular dissociation of the tissue); (4) cut, incise, transect, or resect tissue or an organ (e.g., a blood vessel); (5) create perforations or holes within tissue; and/or (6) coagulate blood and severed blood vessels.

In one method of the present invention, the tissue structures are incised by volumetrically removing or ablating tissue along a cutting path. In this procedure, a high frequency voltage difference is applied between one or more active electrode (s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has a relatively high electrical impedance, it minimizes the current flow into the electrically conductive fluid. Within the vaporized fluid a plasma is formed, and charged particles (e.g., electrons) cause the localized molecular dissociation or disintegration of components of the target tissue, to a depth of perhaps several cell layers. This molecular dissociation results in the volumetric removal of tissue from the target site. This ablation process, which typically subjects the target tissue to a temperature in the range of 40° C. to 70° C., can be precisely controlled to effect the removal of tissue to a depth as little as about 10 microns, with little or no thermal or other damage to surrounding tissue. This cool ablation phenomenon has been termed Coblation®.

While not being bound by theory, applicant believes that the principle mechanism of tissue removal in the Coblation® mechanism of the present invention is energetic electrons or ions that have been energized in a plasma adjacent to the active electrode(s). When a liquid is heated sufficiently that atoms vaporize from the liquid at a greater rate than they recondense, a gas is formed. When the gas is heated sufficiently that the atoms collide with each other and electrons are removed from the atoms in the process, an ionized gas or plasma is formed. (A more complete description of plasmas (the so-called "fourth state of matter") can be found in Plasma Physics, by R. J. Goldston and P. H. Rutherford of the Plasma Physics Laboratory of Princeton University (1995), the complete disclosure of which is incorporated herein by reference.) When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating and ionizing a gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; electrical insulators over the electrodes; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) contains a large amount of lipid material having double bonds, the breakage of which requires an energy level substantially higher than 4 eV to 5 eV. Accordingly, the present invention can be configured such that lipid components of adipose tissue are selectively not ablated. Of course, the present invention may be used to effectively ablate cells of adipose tissue such that the inner fat content of the cells is released in a liquid form. Alternatively, the invention can be configured (e.g., by increasing the voltage or changing the electrode configuration to increase the current density at the electrode tips) such that the double bonds of lipid materials are readily broken leading to molecular dissociation of lipids into low molecular weight condensable gases, generally as described hereinabove. A more complete description of the Coblation® phenomenon can be found in commonly assigned U.S. Pat. No. 5,683,366 and co-pending U.S. patent application Ser. No. 09/032,375, filed Feb. 27, 1998, the complete disclosures of which are incorporated herein by reference.

Methods of the present invention typically involve the application of high frequency (RF) electrical energy to one or more active electrodes in an electrically conductive environment to remove (i.e., resect, incise, perforate, cut, or ablate) a target tissue, structure, or organ; and/or to seal one or more blood vessels within the region of the target tissue. The present invention is particularly useful for sealing larger arterial vessels, e.g., having a diameter on the order of 1 mm or greater. In some embodiments, a high frequency power supply is provided having an ablation mode, wherein a first voltage is applied to an active electrode sufficient to effect molecular dissociation or disintegration of the tissue; and a coagulation mode, wherein a second, lower voltage is applied to an active electrode (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to both coagulate with the coagulation electrode(s), and to ablate or contract tissue with the active electrode(s). In other embodiments, the power supply is combined with the coagulation probe such that the coagulation electrode is used when the power supply is in the coagulation mode (low voltage), and the active electrode(s) are used when the power supply is in the ablation mode (higher voltage).

In one method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described above. During this process, vessels within the tissue are severed. Smaller vessels may be automatically sealed with the system and method of the present invention. Larger vessels and those with a higher flow rate, such as arterial vessels, may not be automatically sealed in the ablation mode. In these cases, the severed vessels may be sealed by actuating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different probe may be pressed against the severed vessel. Once the vessel is adequately sealed or coagulated, the surgeon may activate a control (e.g., another foot pedal) to increase the voltage of the power supply back into the ablation mode. According to another aspect of the invention, larger vessels may be clamped against the active electrode and coagulated prior to being severed via the cool ablation process of the invention.

The present invention is also useful for removing or ablating tissue around nerves, such as spinal, or cranial nerves, e.g., the hypoglossal nerve, the optic nerve, facial nerves, vestibulocochlear nerves and the like. This is particularly advantageous when removing tissue that is located close to nerves. One of the significant drawbacks with the conventional RF devices, scalpels, and lasers is that these devices do not differentiate between the target tissue and the surrounding nerves or bone. Therefore, the surgeon must be extremely careful during these procedures to avoid damage to the nerves within and around the target tissue. In the present invention, the Coblation® process for removing tissue results in no, or extremely small amounts, of collateral tissue damage, as described above. This allows the surgeon to remove tissue close to a nerve without causing collateral damage to the nerve fibers and surrounding tissue.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue that is treated. The system of the present invention measures the electrical properties of the tissue at the tip of the probe with one or more active electrode(s). These electrical properties may include electrical conductivity at one, several, or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode(s) either individually or to the complete array of electrodes, if and when the tissue encountered at the tip or working end of the probe is normal tissue based on the measured electrical properties.

In one embodiment, the current limiting elements are configured such that the active electrodes will shut down or turn off when the electrical impedance reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to target tissue, will continue to conduct electric current to the return electrode. This selective ablation or removal of lower impedance tissue in combination with the Coblation® mechanism of the present invention allows the surgeon to precisely remove tissue around nerves or bone. Applicant has found that the present invention is capable of volumetrically removing tissue closely adjacent to nerves without impairing the function of the nerves, and without significantly damaging the tissue of the epineurium.

The present invention can be also be configured to create an incision in a bone of the patient. For example, the systems of the present invention can be used to create an incision in the sternum for access to the thoracic cavity. Applicant has found that the Coblation® mechanism of the present invention allows the surgeon to precisely create an incision in the sternum while minimizing or preventing bone bleeding. The high frequency voltage is applied between the active electrode(s) and the return electrode(s) to volumetrically remove the bone from a specific site targeted for the incision. As the active electrode(s) are passed through the incision in the bone, the sides of the active electrodes (or a third coagulation electrode) slidingly contact the bone surrounding the incision to provide hemostasis in the bone. A more complete description of such coagulation electrodes can be found in U.S. patent application Ser. No. 09/162,117, filed Sep. 28, 1998, the complete disclosure of which is incorporated herein by reference.

The present invention can also be used to dissect and harvest blood vessels from the patient's body during a CABG procedure. The system of the present invention allows a surgeon to dissect and harvest blood vessels, such as the right or left IMA or saphenous vein, while concurrently providing hemostasis at the harvesting site. In some embodiments, a first high frequency voltage, can be delivered in an ablation mode to effect molecular disintegration of connective tissue adjacent to the blood vessel targeted for harvesting; and a second, lower voltage can be delivered to achieve hemostasis of the connective tissue adjacent to the blood vessel. In other embodiments, the targeted blood vessel can be transected at one or more positions along its length, and one or more coagulation electrode(s) can be used to seal the transected blood vessel at the site of transection. The coagulation electrode(s) may be configured such that a single voltage can be applied to the active electrodes to ablate the tissue and to coagulate the blood vessel and target site.

The present invention also provides systems, apparatus, and methods for selectively removing tumors or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team, or viable cancerous cells to other locations within the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the active electrode(s) and one or more return electrode(s) to volumetrically remove at least a portion of the tissue cells in the tumor or lesion by the molecular dissociation of tissue components into non-condensable gases. The high frequency voltage is preferably selected to effect controlled removal of these tissue cells while minimizing substantial tissue necrosis to surrounding or underlying tissue. A more complete description of this phenomenon can be found in co-pending U.S. patent application Ser. No. 09/109,219, filed Jun. 30, 1998, the complete disclosure of which is incorporated herein by reference.

A current flow path between the active electrode(s) and the return electrode(s) may be generated by submerging the tissue site in an electrically conductive fluid (e.g., within a viscous fluid, such as an electrically conductive gel) or by directing an electrically conductive fluid along a fluid path to the target site (i.e., a liquid, such as isotonic saline, or a gas, such as argon). This latter method is particularly effective in a dry field procedure (i.e., the tissue is not submersed in fluid). The use of a conductive gel allows a slower, more controlled delivery rate of conductive fluid as compared with a liquid or a gas. In addition, the viscous nature of the gel may allow the surgeon to more easily contain the gel around the target site (e.g., as compared with containment of isotonic saline). A more complete description of an exemplary method of directing electrically conductive fluid between the active and return electrodes is described in U.S. Pat. No. 5,697,281, the full disclosure of which is incorporated herein by reference. Alternatively, the body's natural conductive fluids, such as blood, may be sufficient to establish a conductive path between the return electrode(s) and the active electrode(s), and to provide the conditions for establishing a vapor layer, as described above. However, conductive fluid that is introduced into the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the tissue at or adjacent to the target site.

In some embodiments of the invention, an electrosurgical probe includes an electrode support for electrically isolating the active electrode(s) from the return electrode, and a fluid delivery port or outlet for directing an electrically conductive fluid to the target site or to the distal end of the probe. The electrode support and the fluid outlet may be recessed from an outer surface of the instrument to confine the electrically conductive fluid to the region immediately surrounding the electrode support. In addition, a shaft of the instrument may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, thereby reducing any thermal damage that might otherwise occur if the vapor layer were extinguished due to a lack of conductive fluid. Provision of the electrically conductive fluid around the target site also helps to maintain the tissue temperature at desired levels.

The electrically conductive fluid should have a threshold conductivity to provide a suitable conductive path between the return electrode and the active electrode(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

An electrosurgical probe or instrument of the invention typically includes a shaft having a proximal end and a distal end, and one or more active electrode(s) disposed at the shaft distal end. The shaft serves to mechanically support the active electrode(s) and permits the treating physician to manipulate the shaft distal end via a handle attached to the proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually have one or more wires, electrode connectors, leads, or other conductive elements running axially therethrough, to permit connection of the electrode(s) to a connection block located at the proximal end of the instrument. The connection block is adapted for coupling the electrode(s) to the power supply or controller. Typically, the connection block is housed within the handle of the probe.

The shaft of an instrument under the invention may have a variety of different shapes and sizes. Generally, the shaft will have a suitable diameter and length to allow the surgeon to access the target site with the distal or working end of the shaft. Thus, the shaft may be provided in a range of sizes according to the particular procedure or tissue targeted for treatment. Typically, the shaft will have a length in the range of from about 5 cm to 30 cm, and have a diameter in the range of from about 0.5 mm to 10 mm. Specific shaft designs will be described in detail in connection with the drawings hereinafter.

The present invention may use a single active electrode or a plurality of electrodes distributed across a contact surface of a probe (e.g., in a linear fashion). In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The active electrodes may be independently current-limited by isolating the terminals from each other and connecting each terminal to a separate power source that is isolated from the other active electrodes. Alternatively, the active electrodes may be connected to each other at either the proximal or distal ends of the probe to form a single wire that couples to a power source.

In one configuration, each individual active electrode is electrically insulated from all other active electrodes within the probe and is connected to a power source which is isolated from each of the other active electrodes in the array, or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the probe, connectors, cable, power supply or along the conductive path from the power supply to the distal tip of the probe. Alternatively, the resistance and/or capacitance may occur on the surface of the active electrode(s) due to oxide layers which form selected active electrodes (e.g., titanium or a resistive coating on the surface of metal, such as platinum).

The distal end of the probe may comprise many independent active electrodes designed to deliver electrical energy in the vicinity of the distal end. The selective application of electrical energy to the conductive fluid is achieved by connecting each individual active electrode and the return electrode to a power source having independently controlled or current limited channels. The return electrode(s) may comprise a single tubular member of electrically conductive material at the distal end of the probe proximal to the active electrode(s) The same tubular member of electrically conductive material may also serve as a conduit for the supply of the electrically conductive fluid between the active and return electrodes. The application of high frequency voltage between the return electrode(s) and the active electrode(s) results in the generation of high electric field intensities at the distal tip of the active electrode(s), with conduction of high frequency current from each active electrode to the return electrode. The current flow from each active electrode to the return electrode(s) is controlled by either active or passive means, or a combination thereof, to deliver electrical energy to the surrounding conductive fluid while minimizing energy delivery to surrounding (non-target) tissue.

The application of a suitable high frequency voltage between the return electrode(s) and the active electrode(s) for appropriate time intervals effects cutting, removing, ablating, shaping, contracting or otherwise modifying the target tissue. In one embodiment, the tissue volume over which energy is dissipated (i.e., over which a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per active electrode) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$. In one embodiment the probe may include a plurality of relatively small active electrodes disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The portion of the electrode support on which the active electrode(s) are mounted generally defines a tissue treatment surface of the probe. The area of the tissue treatment surface can vary widely, and the tissue treatment surface can assume a variety of geometries, with particular areas and geometries being selected for specific applications. The area of the tissue treatment surface can range from about 0.25 $mm^2$ to 75 $mm^2$, usually being from about 0.5 $mm^2$ to 40 $mm^2$. The geometries of the active electrode(s) can be planar, concave, convex, hemispherical, conical, a linear "in-line" array, or virtually any other regular or irregular shape. Most commonly, the active electrode(s) will be located at the shaft distal end of the electrosurgical probe, frequently having planar, disk-shaped, or hemispherical surfaces for use in reshaping procedures, ablating, cutting, dissecting organs, coagulating, or transecting blood vessels. The active electrode(s) may be arranged terminally or laterally on the electrosurgical probe (e.g., in the manner of a scalpel or a blade). However, it should be clearly understood that the active electrode of the invention does not cut or sever tissue mechanically as for a scalpel blade, but rather by the localized molecular dissociation of tissue components due to application of high frequency electric current to the active electrode. In one embodiment, a distal portion of the shaft may be flattened or compressed laterally (e.g., FIGS. 32A-32C). A probe having a laterally compressed shaft may facilitate access to certain target sites or body structures during various surgical procedures.

In embodiments having a plurality of active electrodes, it should be clearly understood that the invention is not limited to electrically isolated active electrodes. For example, a plurality of active electrodes may be connected to a single lead that extends through the probe shaft and is coupled to a high frequency power supply. Alternatively, the probe may incorporate a single electrode that extends directly through the probe shaft or is connected to a single lead that extends to the power source. The active electrode may have a planar or blade shape, a screwdriver or conical shape, a sharpened point, a ball shape (e.g., for tissue vaporization and desiccation), a twizzle shape (for vaporization and needle-like cutting), a spring shape (for rapid tissue debulking and desiccation), a twisted metal shape, an annular or solid tube shape, or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode, or the like.

In one embodiment, the probe comprises a single blade active electrode that extends from an insulating support member, spacer, or electrode support, e.g., a ceramic or silicone rubber spacer located at the distal end of the probe. The insulating support member may be a tubular structure or a laterally compressed structure that separates the blade active electrode from a tubular or annular return electrode positioned proximal to the insulating member and the active electrode. The blade electrode may include a distal cutting edge and sides which are configured to coagulate the tissue as the blade electrode advances through the tissue. In yet another embodiment, the catheter or probe includes a single active electrode that can be rotated relative to the rest of the catheter body, or the entire catheter may be rotated relative to the electrode lead(s). The single active electrode can be positioned adjacent the abnormal tissue and energized and rotated as appropriate to remove or modify the target tissue.

The active electrode(s) are preferably supported within or by an insulating support member positioned near the distal end of the instrument shaft. The return electrode may be located on the instrument shaft, on another instrument, or on the external surface of the patient (i.e., a dispersive pad). For certain procedures, the close proximity of nerves and other sensitive tissue makes a bipolar design more preferable because this minimizes the current flow through non-target tissue and surrounding nerves. Accordingly, the return electrode is preferably either integrated with the instrument body, or located on another instrument. The proximal end of the probe typically includes the appropriate electrical connections for coupling the return electrode(s) and the active electrode(s) to a high frequency power supply, such as an electrosurgical generator.

One exemplary power supply of the present invention delivers a high frequency current selectable to generate average power levels ranging from several milliwatts to tens of watts per electrode, depending on the volume of target tissue being treated, and/or the maximum allowed temperature selected for the instrument tip. The power supply allows the user to select the voltage level according to the specific requirements of a particular otologic procedure, neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power supply having a higher operating frequency, e.g., 300 kHz to 500 kHz may be used in certain procedures in which stray low frequency currents may be problematic. A description of one suitable power supply can be found in co-pending patent application Ser. Nos. 09/058,571 and 09/058,336, filed Apr. 10, 1998, the complete disclosure of both applications are incorporated herein by reference for all purposes.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. The RMS (root mean square) voltage applied will usually be in the range from about 5 volts to 1000 volts, preferably being in the range from about 10 volts to 500 volts depending on the active electrode size, the operating frequency, and the operation mode of the particular procedure or desired effect on the tissue (e.g., contraction, coagulation, cutting or ablation). Typically, the peak-to-peak voltage for ablation or cutting will be in the range of 10 volts to 2000 volts and preferably in the range of 200 volts to 1800 volts, and more preferably in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably 100 to 1000, and more preferably 120 to 600 volts peak-to-peak.

The voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The power supply may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

The power supply may also be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from the active electrode into the low resistance medium (e.g., saline irrigant or blood).

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, purulent fluid, the gaseous products of ablation, or the like. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, co-pending patent application Ser. No. 09/010,382, filed Jan. 21, 1998, the complete disclosure of which is incorporated herein by reference.

During a surgical procedure, the distal end of the instrument and the active electrode(s) may be maintained at a small distance away from the target tissue surface. This small spacing allows for the continuous flow of electrically conductive fluid into the interface between the active electrode(s) and the target tissue surface. The continuous flow of the electrically conductive fluid helps to ensure that the thin vapor layer will remain between the active electrode(s) and the tissue surface. In addition, dynamic movement of the active electrode(s) over the tissue site allows the electrically conductive fluid to cool the tissue underlying and surrounding the target tissue to minimize thermal damage to this surrounding and underlying tissue. Accordingly, the electrically conductive fluid may be cooled to facilitate the cooling of the tissue. Typically, the active electrode(s) will be about 0.02 mm to 2 mm from the target tissue and preferably about 0.05 mm to 0.5 mm during the ablation process. One method of maintaining this space is to move, translate and/or rotate the probe transversely relative to the tissue, i.e., for the operator to use a light brushing motion, to maintain a thin vaporized layer or region between the active electrode and the tissue. Of course, if coagulation or collagen shrinkage of a deeper region of tissue is necessary (e.g., for sealing a bleeding vessel embedded within the tissue), it may be desirable to press the active electrode(s) against the tissue to effect joulean heating therein.

Referring to FIG. 1, an exemplary electrosurgical system 11 for cutting, ablating, resecting, or otherwise modifying tissue will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 211 (see FIG. 2) in the probe 10 for aspirating the target site.

As shown, probe 10 generally includes a proximal handle 19 and an elongate shaft 18 having one or more active electrodes 58 at its distal end. A connecting cable 34 has a connector 26 for electrically coupling the active electrodes 58 to power supply 28. In embodiments having a plurality of active electrodes, active electrodes 58 are electrically isolated from each other and the terminal of each active electrode 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site.

Power supply 28 has an operator controllable voltage level adjustment 30 to change the applied voltage level, which is observable at a voltage level display 32. Power supply 28 also includes first, second, and third foot pedals 37, 38, 39 and a cable 36 which is removably coupled to power supply 28. The foot pedals 37, 38, 39 allow the surgeon to remotely adjust the energy level applied to active electrode(s) 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the ablation mode. In the ablation mode, a sufficient voltage is applied to the active electrodes to establish the requisite conditions for molecular dissociation of the tissue (i.e., vaporizing a portion of the electrically conductive fluid, ionizing the vapor layer and accelerating charged particles against the tissue). As discussed above, the requisite voltage level for ablation will vary depending on the number, size, shape and spacing of the electrodes, the distance in which the electrodes extend from the support member, etc. When the surgeon is using the power supply in the ablation mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient means for controlling the power supply while manipulating the probe during a surgical procedure.

In the coagulation mode, the power supply 28 applies a low enough voltage to the active electrode(s) (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in Provisional Patent Application No. 60/062,997, filed Oct. 23, 1997, the contents of which are incorporated herein by reference in their entirety.

Figure 2:
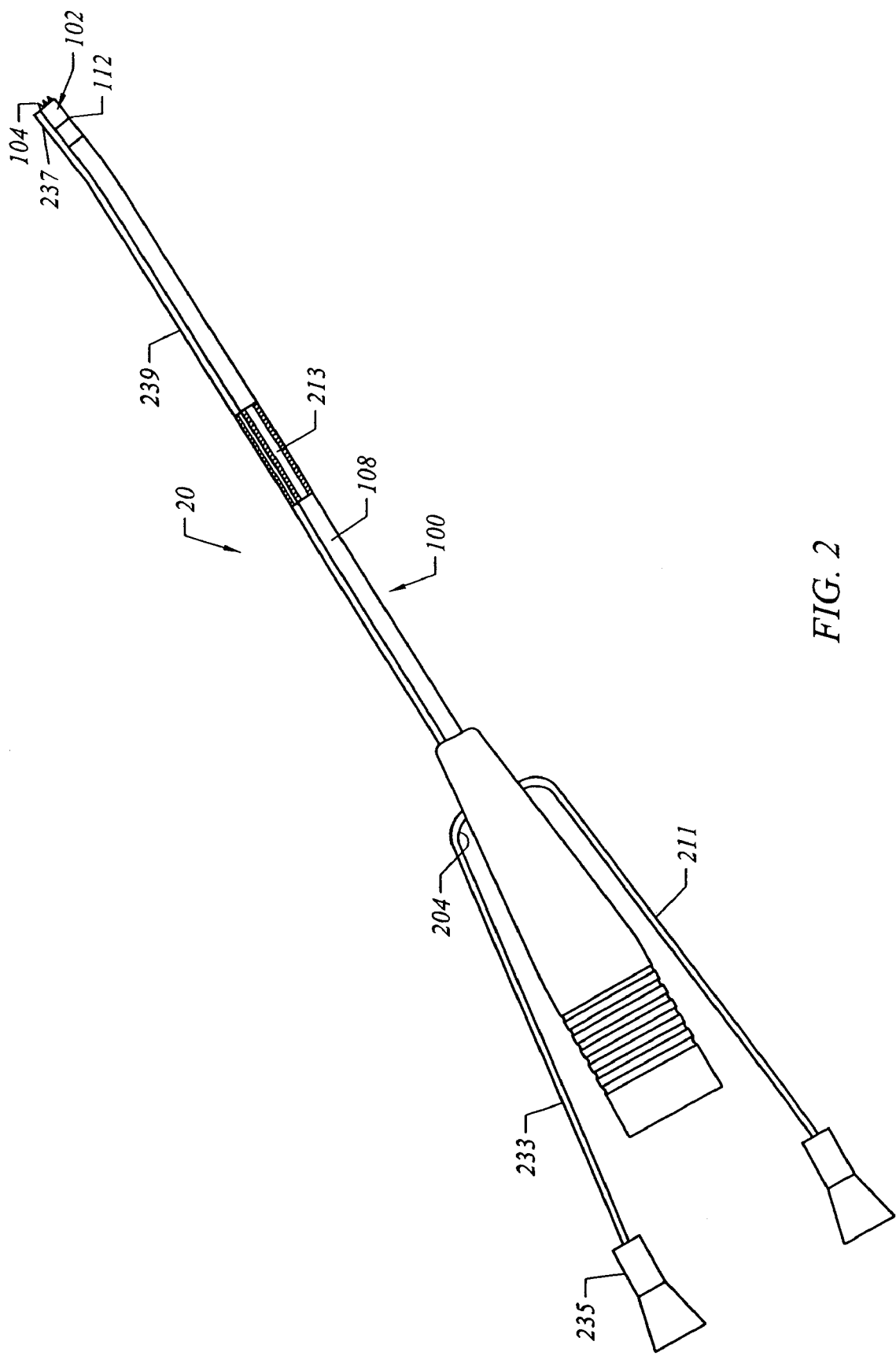
FIG. 2 is a side view of an electrosurgical probe according to the present invention.

FIG. 2 shows an electrosurgical probe 20 according to one embodiment of the invention. Probe 20 may be used in conjunction with a system similar or analogous to system 11 (FIG. 1). As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 may comprise a plastic material that is easily molded into the shape shown in FIG. 3, or shaft 100 may comprise an electrically conductive material, usually a metal, such as tungsten, stainless steel alloys, platinum or its alloys, titanium or its alloys, molybdenum or its alloys, and nickel or its alloys. In the latter case (i.e., shaft 100 is electrically conductive), probe 20 includes an electrically insulating jacket 108, which is typically formed as one or more electrically insulating sheaths or coatings, such as polytetrafluoroethylene, polyimide, and the like. The provision of electrically insulating jacket 108 over shaft 100 prevents direct electrical contact between the metal shaft and any adjacent body structure or the surgeon. Such direct electrical contact between a body structure (e.g., heart, bone, nerves, skin, or other blood vessels) and an exposed electrode could result in unwanted heating and necrosis of the structure at the point of contact.

Handle 204 typically comprises a plastic material that is easily molded into a suitable shape for handling by the surgeon. Handle 204 defines an inner cavity (not shown) that houses an electrical connections unit 250 (FIG. 5), and provides a suitable interface for coupling probe 20 to power supply 28 via an electrical connecting cable. Electrode support member 102 extends from the distal end of shaft 100 (usually about 1 mm to 20 mm), and provides support for an active electrode or a plurality of electrically isolated active electrodes 104. In the specific configuration shown in FIG. 2, probe 20 includes a plurality of active electrodes. As shown in FIG. 2, a fluid tube 233 extends through an opening in handle 204, and includes a connector 235 for connection to a fluid supply source for supplying electrically conductive fluid to the target site. Fluid tube 233 is coupled to a distal fluid tube 239 that extends along the outer surface of shaft 100 to an opening 237 at the distal end of the probe 20, as will be discussed in detail below. Of course, the invention is not limited to this configuration. For example, fluid tube 233 may extend through a single lumen (not shown) in shaft 100, it may be coupled to a plurality of lumens (also not shown) that extend through shaft 100 to a plurality of openings at its distal end, or the fluid tube may be completely independent of shaft 100. Probe 20 may also include a valve or equivalent structure for controlling the flow rate of the electrically conductive fluid to the target site.

Figure 3:
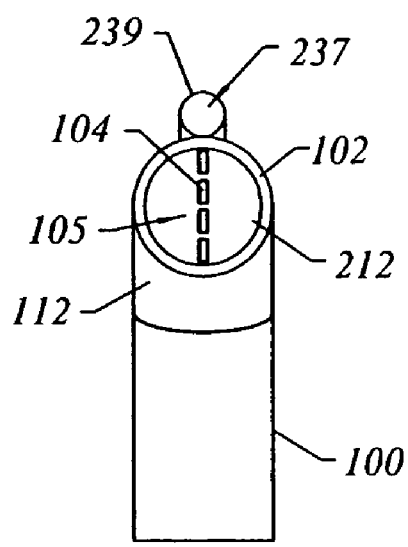
FIG. 3 is an end view of the distal portion of the probe of FIG. 2.
Figure 4:
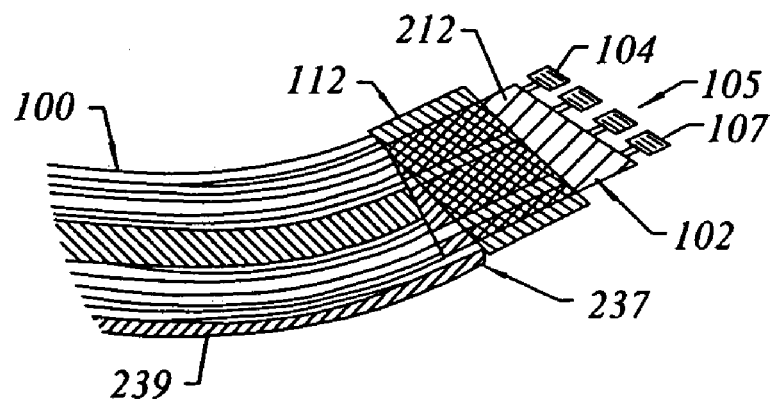
FIG. 4 is a cross sectional view of the distal portion of the electrosurgical probe of FIG. 2.

As shown in FIGS. 3 and 4, electrode support member 102 has a substantially planar tissue treatment surface 212 and comprises a suitable insulating material (e.g., a ceramic or glass material, such as alumina, zirconia and the like)

which could be formed at the time of manufacture in a flat, hemispherical or other shape according to the requirements of a particular procedure. The preferred support member material is alumina (Kyocera Industrial Ceramics Corporation, Elkgrove, Ill.), because of its high thermal conductivity, good electrically insulative properties, high flexural modulus, resistance to carbon tracking, biocompatibility, and high melting point. Electrode support member 102 is adhesively joined to a tubular support member (not shown) that extends most or all of the distance between support member 102 and the proximal end of probe 20. The tubular member preferably comprises an electrically insulating material, such as an epoxy or silicone-based material.

In a preferred construction technique, active electrodes 104 extend through pre-formed openings in the support member 102 so that they protrude above tissue treatment surface 212 by the desired distance. The electrodes are then bonded to the tissue treatment surface 212 of support member 102, typically by an inorganic sealing material. The sealing material is selected to provide effective electrical insulation, and good adhesion to both support member 102 and active electrodes 104. In one embodiment, active electrodes 104 comprise an electrically conducting, corrosion resistant metal, such as platinum or titanium. The sealing material additionally should have a compatible thermal expansion coefficient and a melting point well below that of platinum or titanium and alumina or zirconia, typically being a glass or glass ceramic.

In the embodiment shown in FIGS. 2-5, probe 20 includes a return electrode 112 for completing the current path between active electrodes 104 and a high frequency power supply 28 (see FIG. 1). As shown, return electrode 112 preferably comprises an annular conductive band coupled to the distal end of shaft 100 at a location proximal to tissue treatment surface 212 of electrode support member 102, typically about 0.5 mm to 10 mm proximal to surface 212, and more preferably about 1 mm to 10 mm proximal to surface 212. Return electrode 112 is coupled to a connector 258 that extends to the proximal end of probe 20, where it is suitably connected to power supply 28 (FIGS. 1 and 2).

As shown in FIG. 2, return electrode 112 is not directly connected to active electrodes 104. To complete this current path so that active electrodes 104 are electrically connected to return electrode 112, electrically conductive fluid (e.g., isotonic saline) is caused to flow therebetween. In the representative embodiment, the electrically conductive fluid is delivered through an external fluid tube 239 to opening 237, as described above (FIGS. 2 and 4). Alternatively, the fluid may be continuously delivered by a fluid delivery element (not shown) that is separate from probe 20.

In alternative embodiments, the fluid path may be formed in probe 20 by, for example, an inner lumen or an annular gap between the return electrode and a tubular support member within shaft 100 (not shown). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in U.S. Pat. No. 5,697,281, filed on Jun. 7, 1995, the complete disclosure of which is incorporated herein by reference.

Referring to FIGS. 3 and 4, the electrically isolated active electrodes 104 are preferably spaced from each other and aligned to form a linear array 105 of electrodes for cutting a substantially linear incision in the tissue. The tissue treatment surface and individual active electrodes 104 will usually have dimensions within the ranges set forth above. Active electrodes 104 preferably have a distal edge 107 to increase the electric field intensities around terminals 104, and to facilitate cutting of tissue. Thus, active electrodes 104 have a screwdriver shape in the representative embodiment of FIGS. 2-4. In one representative embodiment, the tissue treatment surface 212 has a circular cross-sectional shape with a diameter in the range of about 1 mm to 30 mm, usually about 2 mm to 20 mm. The individual active electrodes 104 preferably extend outward from tissue treatment surface 212 by a distance of about 0.1 mm to 8 mm, usually about 1 mm to 4 mm. Applicant has found that this configuration increases the high electric field intensities and associated current densities around active electrodes 104 to facilitate the ablation of tissue as described in detail above.

Probe 20 may include a suction or aspiration lumen 213 (see FIG. 2) within shaft 100 and a suction tube 211 (FIG. 2) for aspirating tissue, fluids and/or gases from the target site. In this embodiment, the electrically conductive fluid generally flows from opening 237 of fluid tube 239 radially inward and then back through one or more openings (not shown) in support member 102. Aspirating the electrically conductive fluid during surgery allows the surgeon to see the target site, and it prevents the fluid from flowing into the patient's body (e.g., the thoracic cavity). This aspiration should be controlled, however, so that the conductive fluid maintains a conductive path between the active electrode(s) and the return electrode. In some embodiments, the probe 20 will also include one or more aspiration electrode(s) (not shown) coupled to the aspiration lumen for inhibiting clogging during aspiration of tissue fragments from the surgical site. A more complete description of these embodiments can be found in commonly assigned co-pending U.S. patent application Ser. No. 09/010,382, filed Jan. 21, 1998, the complete disclosure of which is incorporated herein by reference for all purposes.

Figure 5:
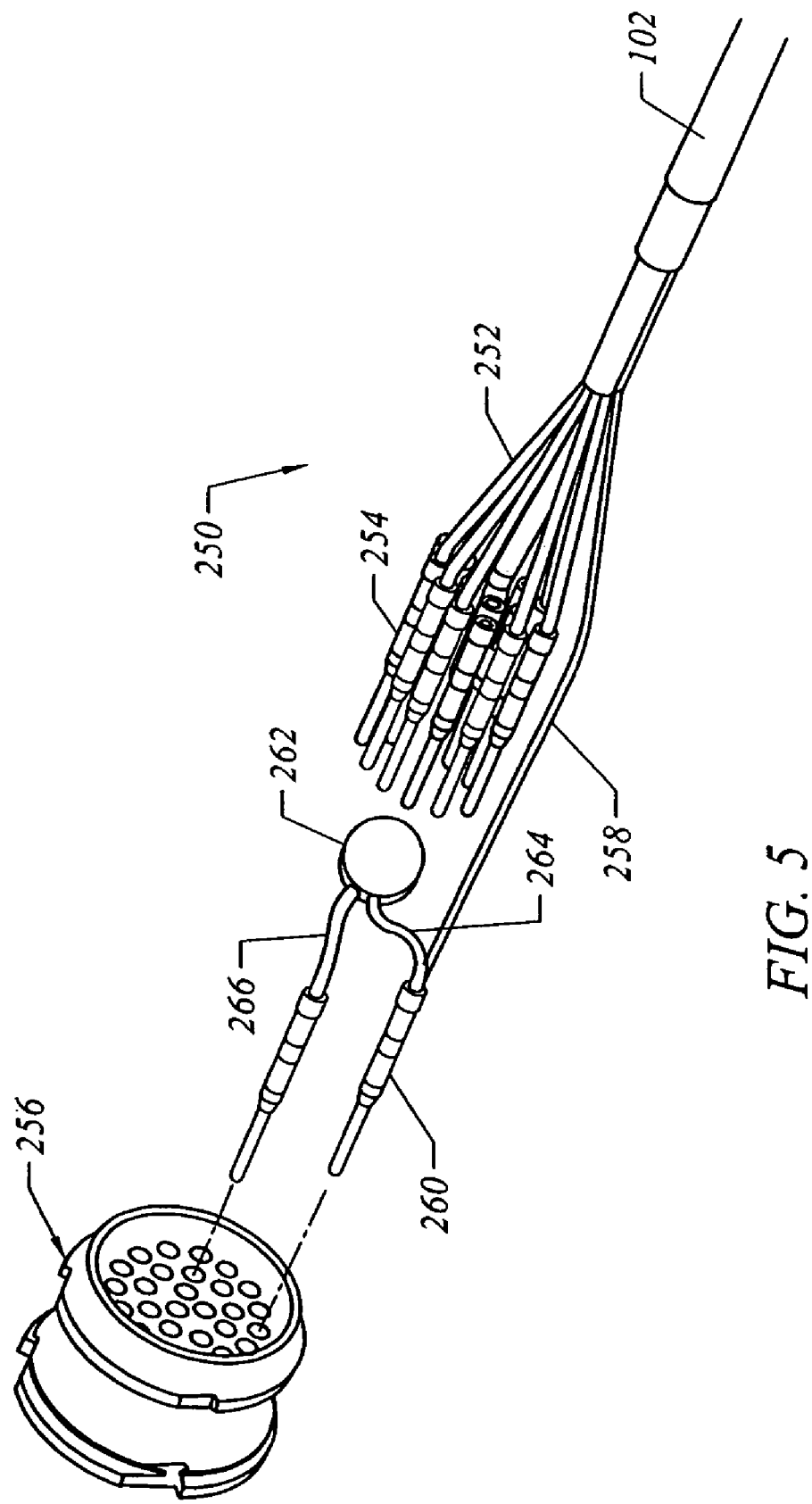
FIG. 5 is an exploded view of a proximal portion of the electrosurgical probe.

FIG. 5 illustrates the electrical connections 250 within handle 204 for coupling active electrodes 104 and return electrode 112 to the power supply 28. As shown, a plurality of wires 252 extend through shaft 100 to couple electrodes 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, probe 20 further includes an identification element that is characteristic of the particular electrode assembly so that the same power supply 28 can be used for different electrosurgical operations. In one embodiment, for example, probe 20 includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conductive medium and/or the tissue at the target site. The voltage reduction element primarily allows the electrosurgical probe 10/20 to be compatible with a range of different power supplies that are adapted to apply higher voltages for ablation or vaporization of tissue (e.g., various power supplies or generators manufactured by ArthroCare Corporation, Sunnyvale, Calif.). For contraction of tissue, for example, the voltage reduction element will serve to reduce a voltage of about 100 to 135 volts RMS (which corresponds to a setting of 1 on the ArthroCare Model 970 and 980 (i.e., 2000) Generators) to about 45 to 60 volts RMS, which is a suitable voltage for contraction of tissue without ablation (e.g., molecular dissociation) of the tissue.

Again with reference to FIG. 5, n the representative embodiment the voltage reduction element is a dropping capacitor 262 which has a first leg 264 coupled to the return electrode wire 258 and a second leg 266 coupled to connector block 256. Of course, the capacitor may be located in other places within the system, such as in, or distributed along the length of, the cable, the power supply, the connector, etc. In addition, it will be recognized that other voltage reduction elements, such as diodes, transistors, inductors, resistors, capacitors or combinations thereof, may be used in conjunction with the present invention. For example, probe 20 may include a coded resistor (not shown) that is constructed to lower the voltage applied between return electrode 112 and active electrodes 104 to a suitable level for contraction of tissue. In addition, electrical circuits may be employed for this purpose.

Alternatively or additionally, the cable 22 that couples the power supply 28 to probe 10/20 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor.

Further, it should be noted that various electrosurgical probes of the present invention can be used with a particular power supply that is adapted to apply a voltage within a selected range for a certain procedure or treatment. In which case, a voltage reduction element or circuitry may not be necessary nor desired.

With reference to FIGS. 6-8, electrode support member 70 according to one embodiment includes a multi-layer substrate comprising a suitable high temperature, electrically insulating material, such as ceramic. The multi-layer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material. A more complete description of such support members 370 can be found in U.S. patent application Ser. No. 08/977,845, filed Nov. 25, 1997, the entire disclosure of which is incorporated herein by reference.

Figure 9A:
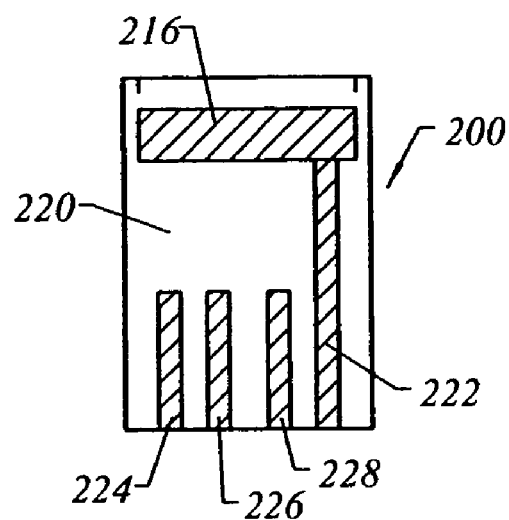
Figure 9B:
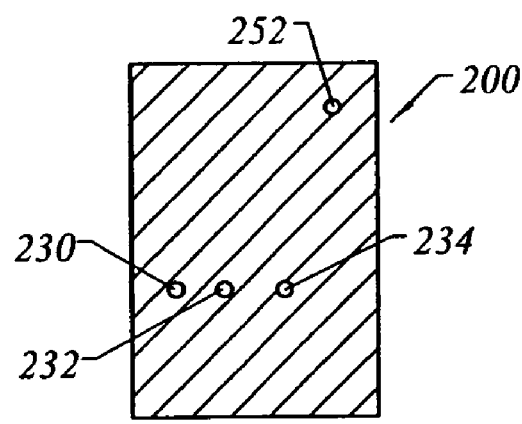

In the representative embodiment, support member 70 comprises five ceramic layers 200, 202, 204, 206, 208 (see FIGS. 6-10), three gold plated active electrodes 210a, 210b, 210c and first and second gold plated return electrodes 216, 218. As shown in FIGS. 9A and 9B, a first ceramic layer 200, which is one of the outer layers of support 70, includes first gold plated return electrode 216 on a lateral surface 220 of layer 200. First ceramic layer 200 further includes a gold conductive strip 222 extending from return electrode 216 to the proximal end of layer 200 for coupling to a lead wire (not shown), and three gold conductive lines 224, 226, 228 extending from a mid-portion of layer 200 to its proximal end. Conductive strips 224, 226, 228 are each coupled to one of the active electrodes 210a, 210b, 210c by conductive holes or vias 230, 232, 234, respectively. As shown, all three vias 230, 232, 234 extend through wafer layer 200.

Figure 10A:
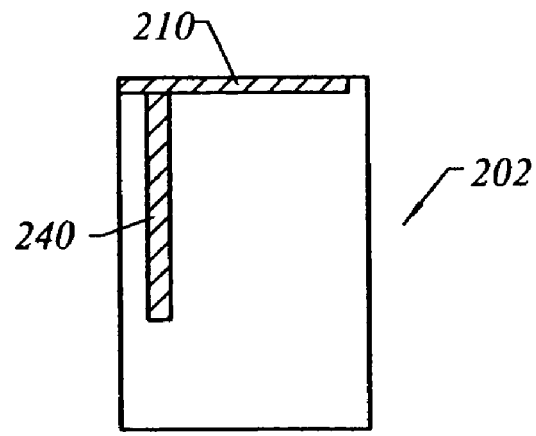
Figure 10B:
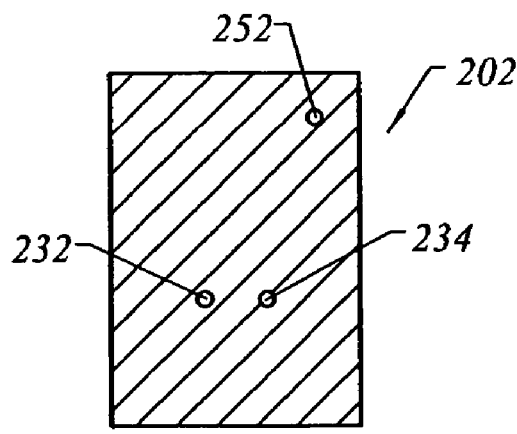

Referring to FIGS. 10A and 10B, a second wafer layer 202 is bonded between first outer wafer layer 200 and a middle wafer layer 204 (See FIGS. 11A and 11B). As shown, first active electrode 210a is attached to the distal surface of second wafer layer 202, and a conductive strip 240 extends to via 230 to couple active electrode 210a to a lead wire. Similarly, wafer layers 204 and 206 (FIGS. 11A, 11B, 12A, and 12B) each have an active electrode 210b, 210c plated to their distal surfaces, and a conductive strip 242, 244, respectively, extending to one of the vias 232, 234, respectively. Note that the vias only extend as far as necessary through the ceramic layers. As shown in FIG. 13, a second outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
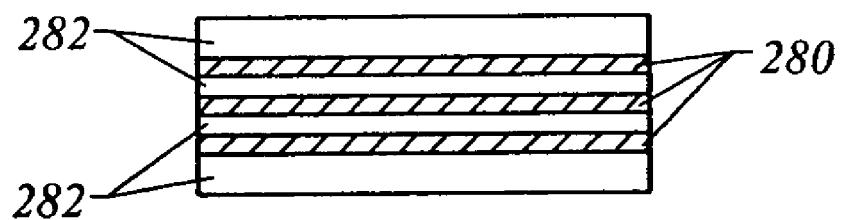
FIGS. 14 and 15 illustrate an alternative multi-layer wafer design according to the present invention.
Figure 15:
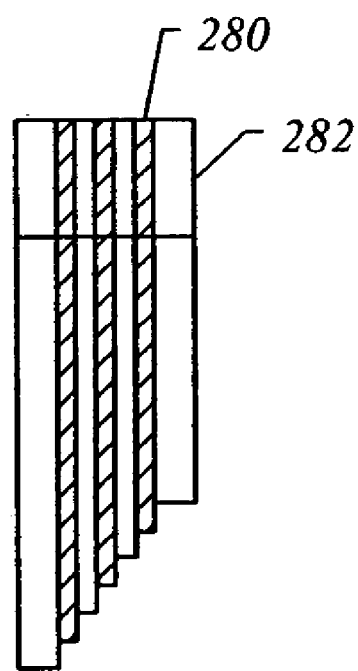

Of course, it will be recognized that a variety of different types of single layer and multi-layer wafers may be constructed according to the present invention. For example, FIGS. 14 and 15 illustrate an alternative embodiment of the multi-layer ceramic wafer, wherein the active electrodes comprise planar strips 280 that are plated or otherwise bonded between the ceramic wafer layers 282. Each of the planar strips 280 has a different length, as shown in FIG. 15, so that the active electrodes can be electrically isolated from each other, and coupled to lead wires by vias (not shown).

Figure 16:
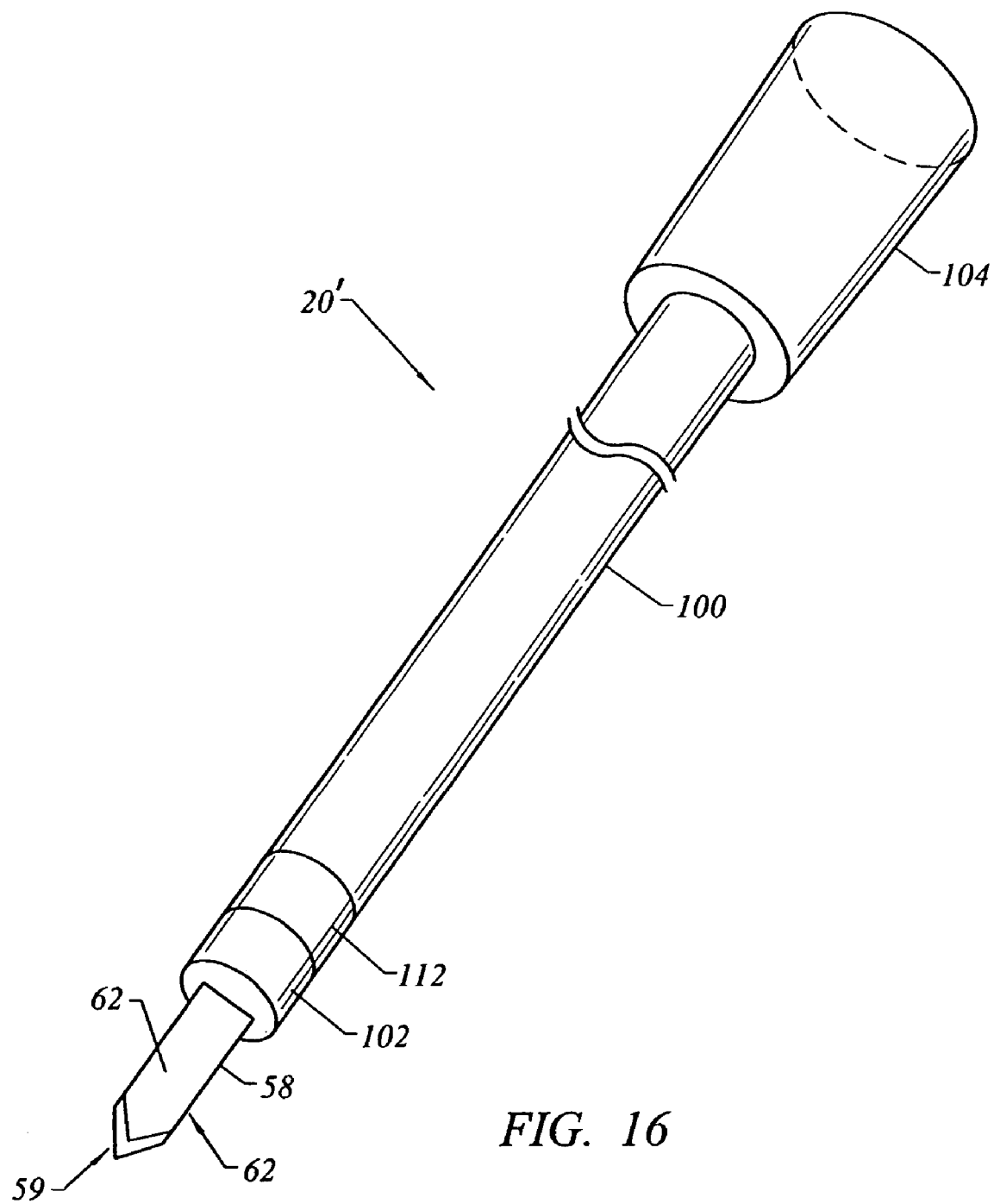
FIG. 16 is a perspective view of an electrosurgical probe having an elongated, blade-like active electrode.

FIG. 16 illustrates an electrosurgical probe 20' according to another embodiment of the present invention. Probe 20' generally includes handle 104 attached to shaft 100, and has a single, thin, elongated active blade electrode 58. Active electrode 58 is mechanically and electrically separated from return electrode 112 by a support structure 102. The active blade electrode 58 has a sharp distal edge 59 which helps facilitate the cutting process, and sides 62 which contact the tissue (e.g., bone) as the blade electrode 58 passes through the tissue or body structure. By contacting the sides of the blade electrode 58 directly with the tissue or body structure, the electrical power supplied to electrode 58 by power supply 28 can provide hemostasis to the body structure during the cutting process. Optionally, probe 20' can further include one or more coagulation electrode(s) (not shown) configured to seal a severed vessel, bone, or other tissue that is being incised. Such coagulation electrode(s) may be configured such that a single voltage can be applied to coagulate with the coagulation electrode(s) while ablating tissue with the active electrode(s). According to one aspect of the invention, probe 20' is particularly useful for creating an incision in a patient's chest. For example, in an open-chest CABG procedure a median sternotomy is first performed in which the sternum is sectioned longitudinally so as to allow the chest to be opened for access to the thoracic cavity. Active electrodes 58 include distal edge 59 suitable for sectioning the sternum, and sides 62 suitable for arresting bone bleeding within the incised sternum. Sides 62 are configured to slidably engage the sternum as active electrode 58 is moved with respect to the sternum. Return electrode 112 is spaced proximally from active electrode 58 such that the electrical current is drawn away from the surrounding tissue. Alternatively, the return electrode 112 may be a dispersive pad located on the external surface of the patient's body. By minimizing bleeding of the sternum during an open-chest procedure, the patient's recovery time can be substantially shortened and patient suffering is alleviated.

Figure 17A:
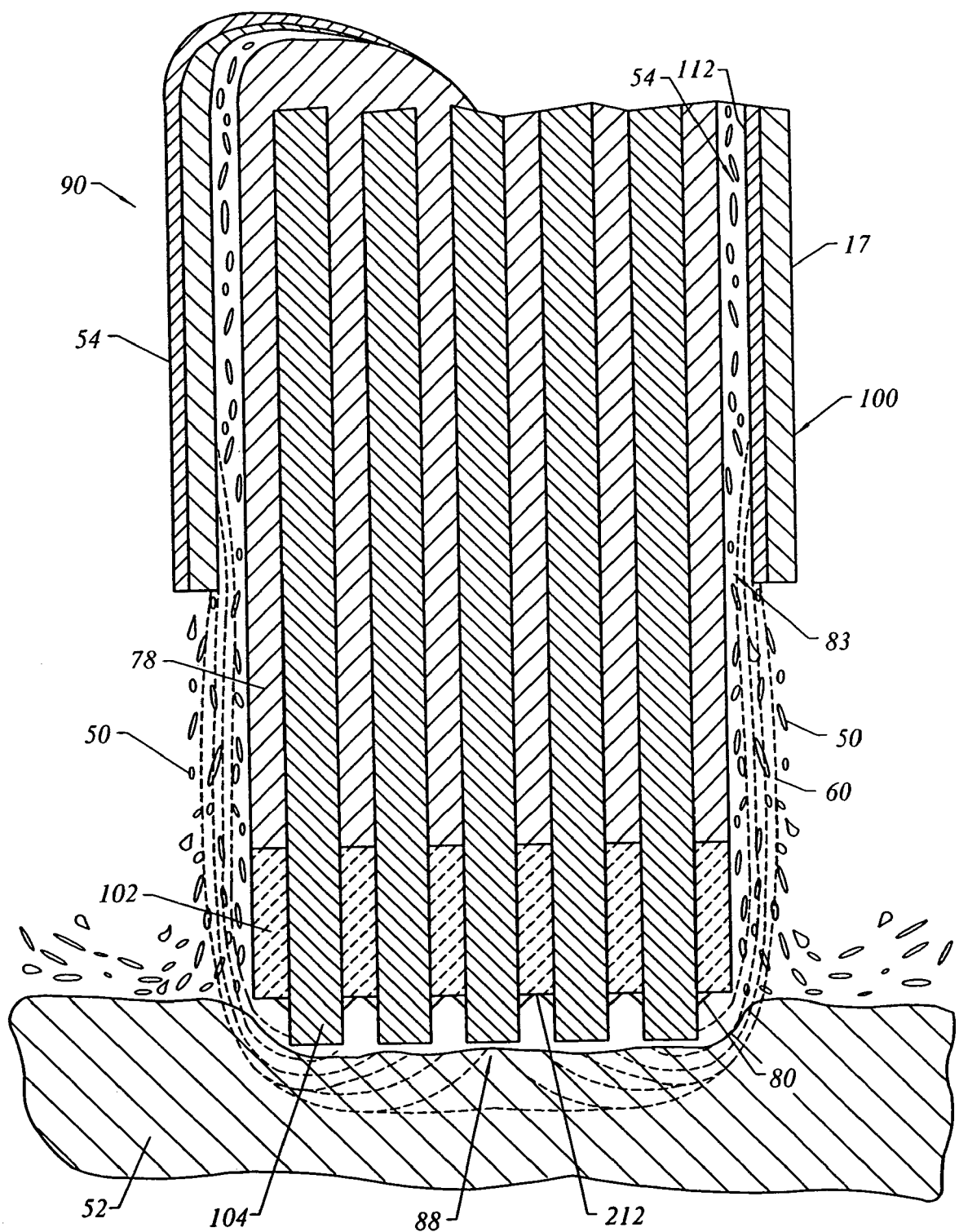
FIG. 17A-17C are cross-sectional views of the distal portions of three different embodiments of an electrosurgical probe according to the present invention.
Figure 17B:
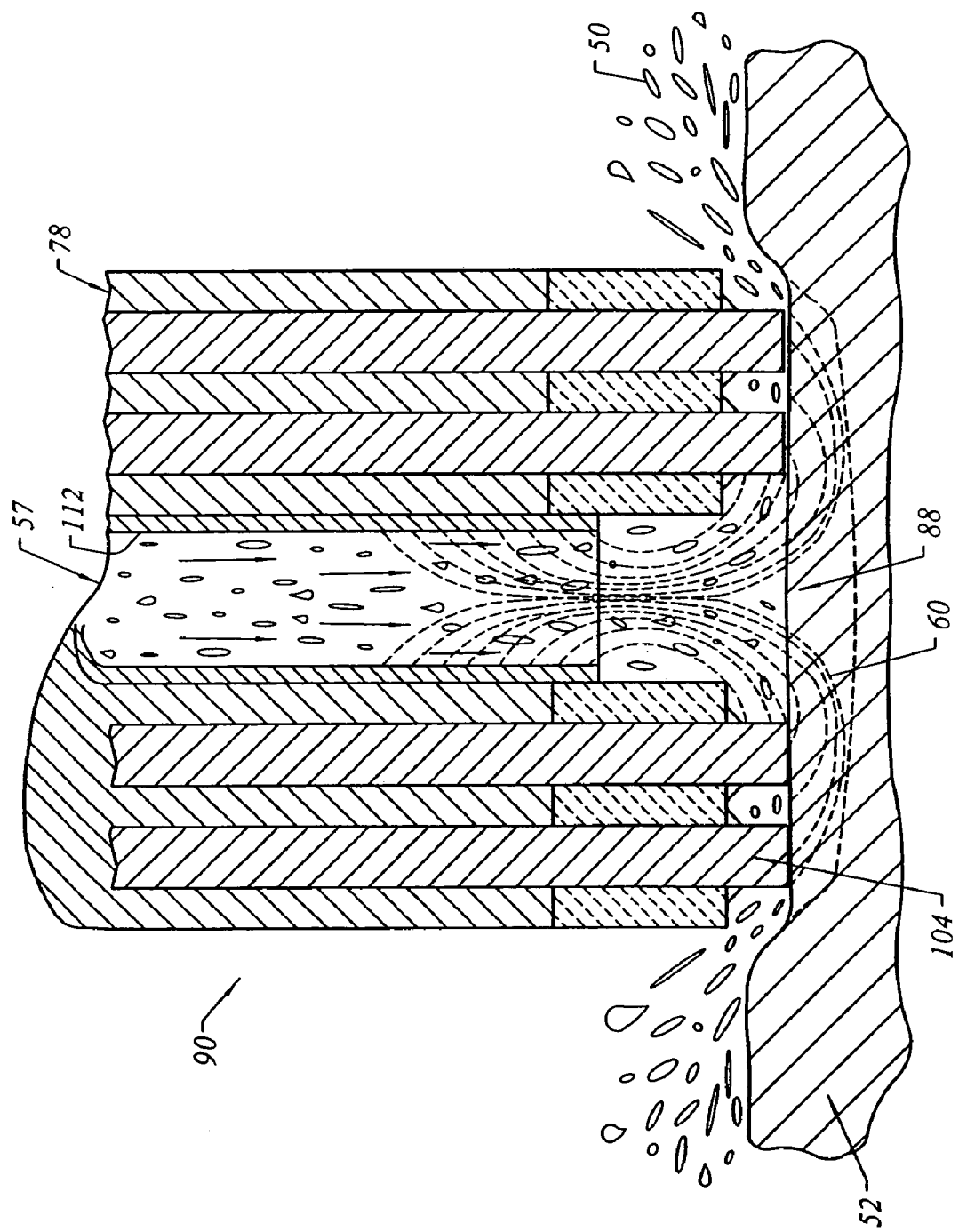
Figure 17C:
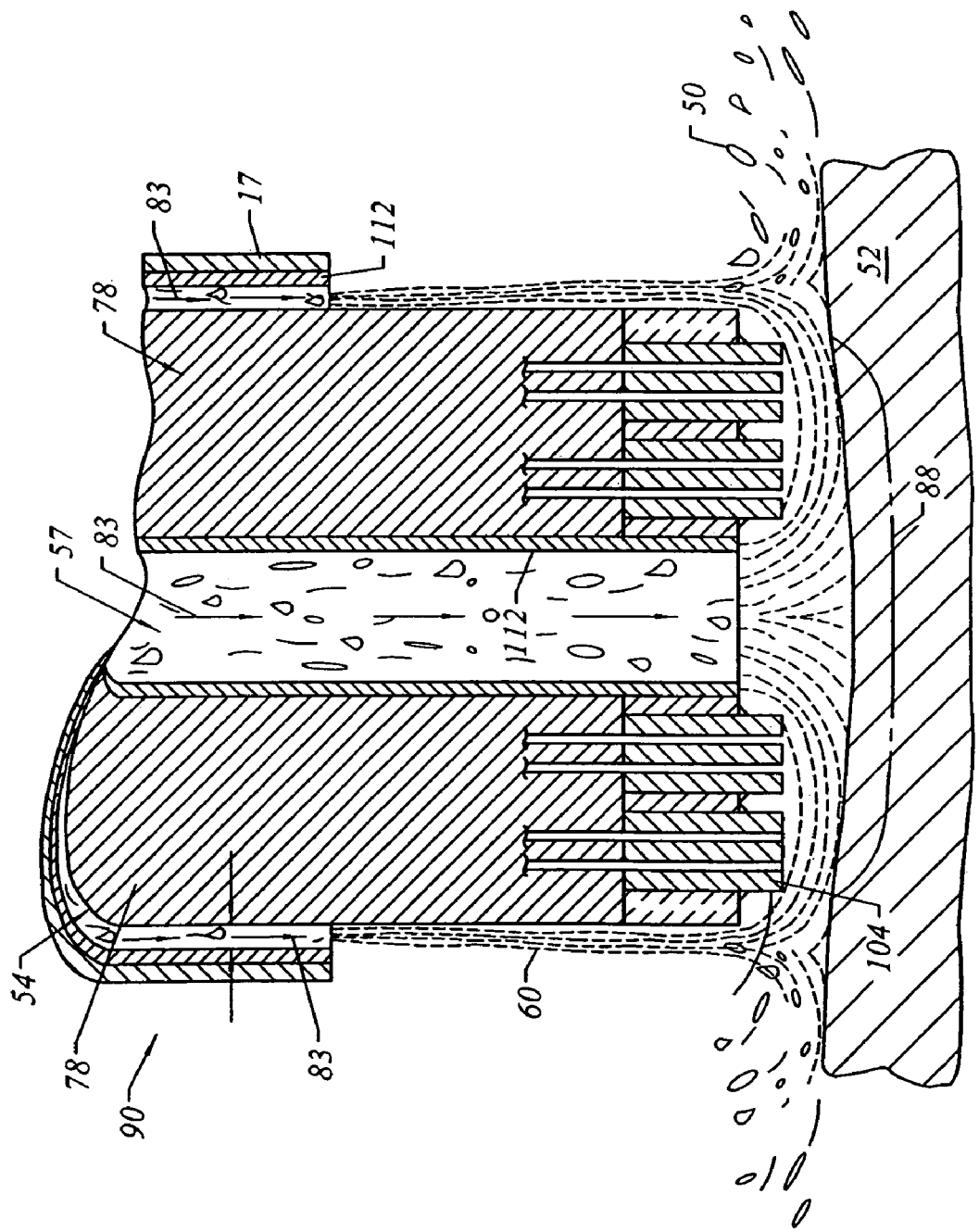

FIGS. 17A-17C schematically illustrate the distal portion of three different embodiments of a probe 90 according to the present invention. As shown in FIG. 17A, active electrodes 104 are anchored in a support 102 of suitable insulating material (e.g., ceramic or glass material, such as alumina, zirconia and the like) which could be formed at the time of manufacture in a flat, hemispherical or other shape according to the requirements of a particular procedure. In one embodiment, the support material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support 102 is adhesively joined to a tubular support member 78 that extends most or all of the distance between matrix 102 and the proximal end of probe 90. Tubular member 78 preferably comprises an electrically insulating material, such as an epoxy or silicone-based material.

According to one construction technique, active electrodes 104 extend through pre-formed openings in the support 102 so that they protrude above tissue treatment surface 212 by the desired distance. The electrodes are then bonded to the tissue treatment surface 212 of support 102, typically by an inorganic sealing material 80. Sealing material 80 is selected to provide effective electrical insulation, and good adhesion to both the support 102 and the platinum or titanium active electrodes. Sealing material 80 additionally should have a compatible thermal expansion coefficient, and a melting point well below that of platinum or titanium and alumina or zirconia, typically being a glass or glass ceramic.

In the embodiment shown in FIG. 17A, return electrode 112 comprises an annular member positioned around the exterior of shaft 100 of probe 90. Return electrode 112 may fully or partially circumscribe tubular member 78 to form an annular gap 54 therebetween for flow of electrically conductive liquid 50 therethrough, as discussed below. Gap 54 preferably has a width in the range of 0.25 mm to 4 mm. Alternatively, probe 90 may include a plurality of longitudinal ribs between tubular member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 17, which is typically formed as one or more electrically insulative sheaths or coatings, such as polytetrafluoroethylene, polyimide, and the like. The provision of the electrically insulative jacket 17 over return electrode 112 prevents direct electrical contact between return electrode 112 and any adjacent body structure. Such direct electrical contact between a body structure (e.g., the heart) and an exposed electrode member 112 could result in unwanted heating and necrosis of the structure at the point of contact.

As shown in FIG. 17A, return electrode 112 is not directly connected to active electrodes 104. To complete a current path so that active electrodes 104 are electrically connected to return electrode 112, electrically conductive liquid 50 (e.g., isotonic saline) is caused to flow along fluid path(s) 83. Fluid path 83 is formed by annular gap 54 between outer return electrode 112 and tubular support member 78. The electrically conductive liquid 50 flowing through fluid path 83 provides a pathway for electrical current flow between active electrodes 104 and return electrode 112, as illustrated by the current flux lines 60 in FIG. 17A. When a voltage difference is applied between active electrodes 104 and return electrode 112, high electric field intensities will be generated at the distal tips of active electrodes 104 with current flow from electrodes 104 through the target tissue to the return electrode, the high electric field intensities causing ablation of tissue 52 in zone 88.

FIG. 17B illustrates another alternative embodiment of electrosurgical probe 90 which has a return electrode 112 positioned within tubular member 78. Return electrode 112 may comprise a tubular member defining an inner lumen 57 for allowing electrically conductive liquid 50 (e.g., isotonic saline) to flow therethrough in electrical contact with return electrode 112. In this embodiment, a voltage difference is applied between active electrodes 104 and return electrode 112 resulting in electrical current flow through the electrically conductive liquid 50 as shown by current flux lines 60. As a result of the applied voltage difference and concomitant high electric field intensities at the tips of active electrodes 104, tissue 52 becomes ablated or transected in zone 88.

FIG. 17C illustrates another embodiment of probe 90 that is a combination of the embodiments in FIGS. 17A and 17B. As shown, this probe includes both an inner lumen 57 and an outer gap or plurality of outer lumens 54 for flow of electrically conductive fluid. In this embodiment, the return electrode 112 may be positioned within tubular member 78 as in FIG. 17B, outside of tubular member 78 as in FIG. 17A, or in both locations.

Figure 18:
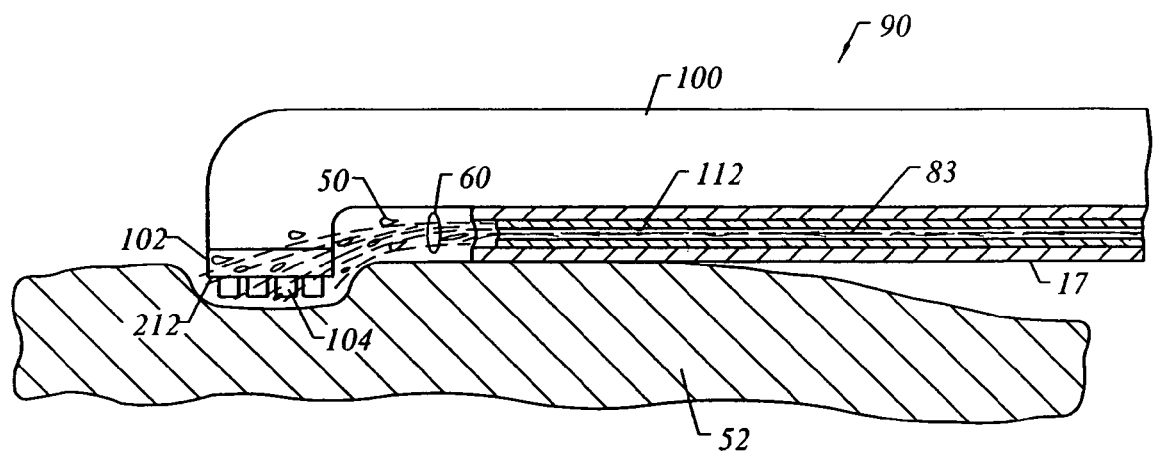
FIG. 18 illustrates an electrosurgical probe with a 90° distal bend and a lateral fluid lumen.

FIG. 18 illustrates another embodiment of probe 90 where the distal portion of shaft 100 is bent so that active electrodes extend transversely to the shaft. Preferably, the distal portion of shaft 100 is perpendicular to the rest of the shaft so that tissue treatment surface 212 is generally parallel to the shaft axis. In this embodiment, return electrode 112 is mounted to the outer surface of shaft 100 and is covered with an electrically insulating jacket 17. The electrically conductive fluid 50 flows along flow path 83 through return electrode 112 and exits the distal end of electrode 112 at a point proximal of tissue treatment surface 212. The fluid is directed exterior of shaft to surface 212 to create a return current path from active electrodes 104, through the fluid 50, to return electrode 112, as shown by current flux lines 60.

Figure 19:
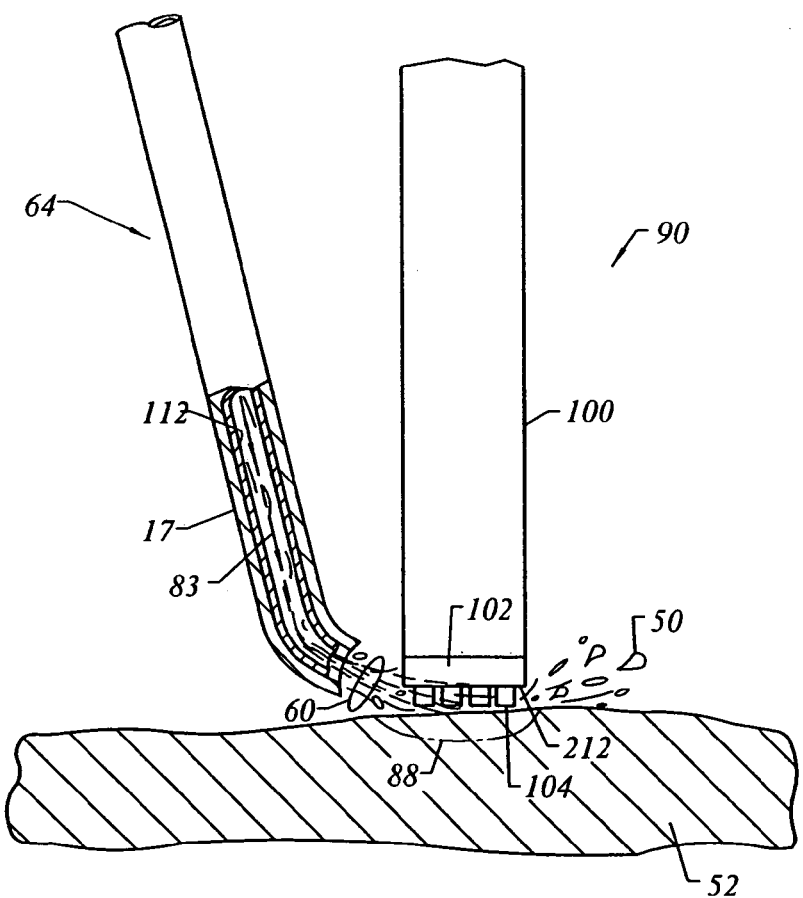
FIG. 19 illustrates an electrosurgical system with a separate fluid delivery instrument according to the present invention.

FIG. 19 illustrates another embodiment of the invention where electrosurgical system 11 further includes a liquid supply instrument 64 for supplying electrically conductive fluid 50 between active electrodes 104 and a return electrode 112'. Liquid supply instrument 64 comprises an inner tubular member or return electrode 112' surrounded by an electrically insulating jacket 17. Return electrode 112' defines an inner passage 83 for flow of fluid 50. As shown in FIG. 19, the distal portion of instrument 64 is preferably bent so that liquid 50 is discharged at an angle with respect to instrument 64. This allows the surgical team to position liquid supply instrument 64 adjacent tissue treatment surface 212 with the proximal portion of supply instrument 64 oriented at a similar angle to probe 90.

Figure 20A:
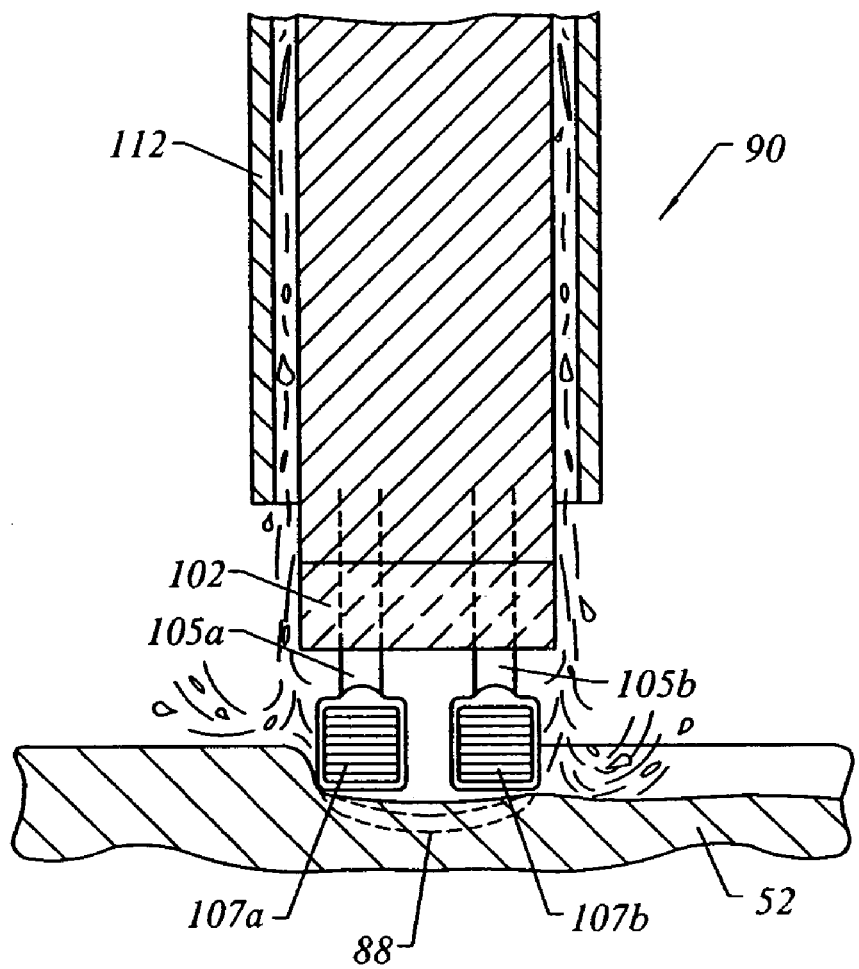
FIGS. 20A and 20B are cross-sectional and end views, respectively, of yet another electrosurgical probe incorporating flattened active electrodes.
Figure 20B:
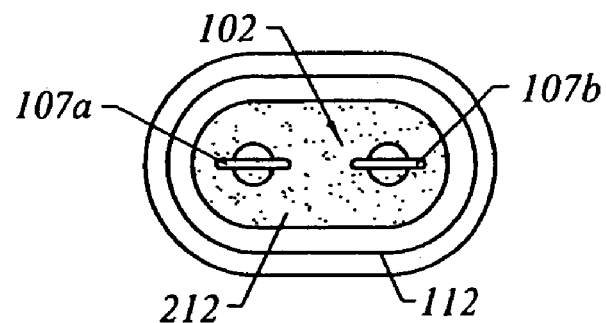

The present invention is not limited to an electrode array disposed on a relatively planar surface at the distal tip of probe 90, as described above. Referring to FIGS. 20A and 20B, an alternative probe 90 includes a pair of electrodes 105a, 105b mounted to the distal end of shaft 100. Electrodes 105a, 105b are electrically connected to a power supply, as described above, and preferably have tips 107a, 107b having a screwdriver shape. The screwdriver shape provides a greater amount of "edges" to electrodes 105a, 105b, to increase the electric field intensity and current density at tips 107*a*, 107*b*, thereby improving the cutting ability as well as the ability to provide hemostasis of the incised tissue.

FIG. 21 illustrates yet another embodiment designed for cutting of body tissue, organs, or structures. In this embodiment, the active electrodes 104 are arranged in a linear or columnar array of one of more closely spaced columns so that as the electrodes 104 are moved along the longer axis (denoted by arrow 160 in FIG. 21), the current flux lines are narrowly confined at the tip of the active electrodes 104 and result in a cutting effect in the body structure being treated. As before, the current flux lines 60 emanating from the active electrodes 104 pass through the electrically conductive liquid to the return electrode structure 112 located proximal to the probe tip.

Referring now to FIGS. 22 and 23, alternative geometries are shown for the active electrodes 104. These alternative electrode geometries allow the electrical current densities emanating from the active electrodes 104 to be concentrated to achieve an increased ablation rate and/or a more concentrated ablation effect due to the fact that sharper edges (i.e., regions of smaller radii of curvature) result in higher current densities. FIG. 22 illustrates a flattened extension of a round wire active electrode 104 which results in higher current densities at the edges 180. Another example is shown in FIG. 23 in which the active electrode 104 is formed into a cone shaped point 182 resulting in higher current densities at the tip of the cone.

Figure 24:
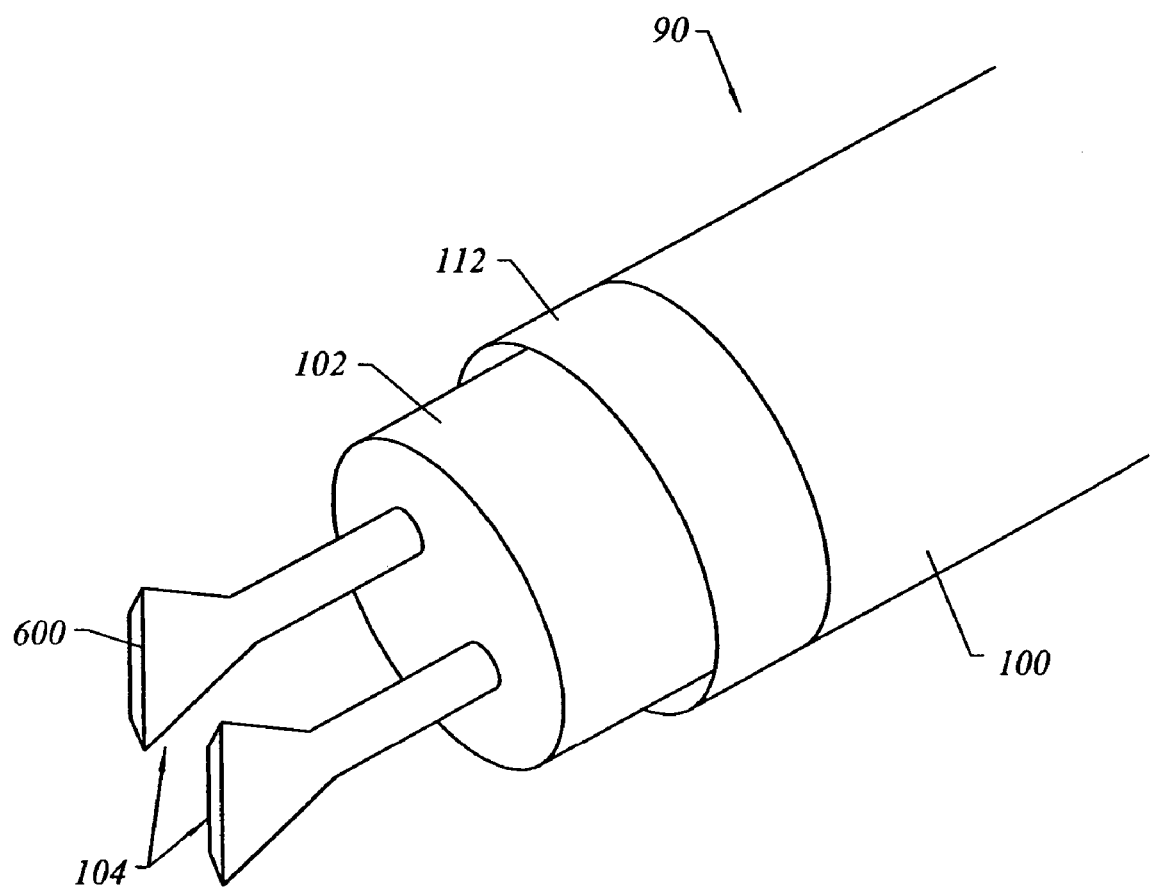
FIG. 24 is a perspective view of the distal portion of another electrosurgical probe according to the present invention.

Another embodiment of the electrosurgical probe is illustrated in FIG. 24. The electrosurgical probe 90 comprises a shaft 100 and at least two active electrodes 104 extending from a support 102 at the distal end of the shaft. The active electrodes 104 preferably define a distal edge 600 for making an incision in tissue. The edges 600 of the active electrodes 104 are substantially parallel with each other and usually spaced a distance of about 4 mm to 15 mm apart, preferably about 8 mm to 10 mm apart. The edges 600 extend from the distal end of support 102 by a distance of about 0.5 mm to 10 mm, preferably about 2 mm to 5 mm. In the exemplary embodiment, probe 90 will include a return electrode 112 spaced proximally from the active electrodes 104. In an alternative embodiment (not shown), one of the active electrodes 104 may function as a return electrode, or the return electrode may be a dispersive pad located on an external surface of the patient's body.

Figure 25:
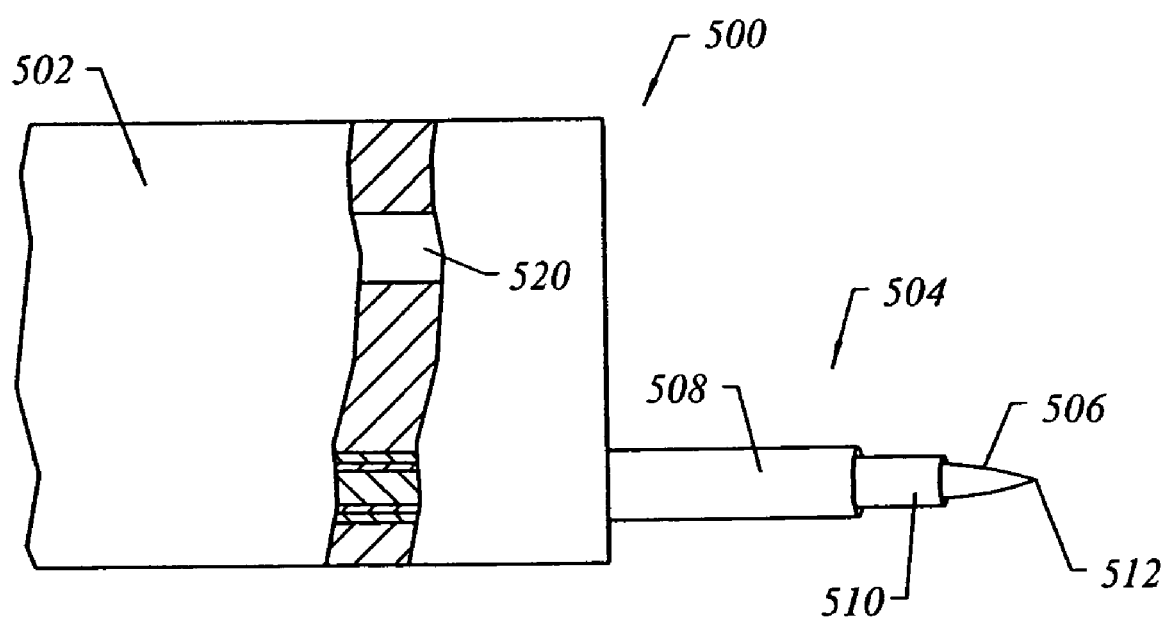
FIG. 25 illustrates another embodiment of the probe of the present invention, specifically designed for creating incisions in external skin surfaces.

FIG. 25 illustrates a distal portion of an electrosurgical probe 500 according to another embodiment of the present invention The embodiment of FIG. 25 is particularly useful for cutting or creating incisions in tissue structures. Probe 500 comprises a support member 502 coupled to a shaft or disposable tip (not shown) as described in previous embodiments. Support member 502 preferably comprises an inorganic electrically insulating material, such as ceramic, glass or glass-ceramic. In this embodiment, however, support member 502 may comprise an organic material, such as plastic, because the active electrode 506 and return electrode 508 are both spaced away from support member 502. Thus, the high intensity electric fields may be far enough away from support member 502 so as to allow an organic material.

An electrode assembly 504 extends from a distal end of support member 502, preferably by a distance of about 2 mm to 20 mm. Electrode assembly 504 comprises a single, active electrode 506 and a return electrode sleeve 508 spaced proximally from active electrode 506 by an insulation member 510, which preferably comprises an inorganic material, such as ceramic, glass or glass-ceramic. As shown, active electrode 506 preferably tapers to a sharp distal end 512 to facilitate the cutting or incising of tissue. In the exemplary embodiment, active electrode 506 has a proximal diameter of about 0.2 to 20 mm and a distal diameter of less than about 0.2 mm. Return electrode 508 is spaced from active electrode 506 a sufficient distance to prevent shorting or arcing therebetween at sufficient voltages to allow the volumetric removal of tissue. In the representative embodiment, the distal exposed portion of return electrode 508 is spaced about 0.5 to about 5 mm from the proximal exposed portion of active electrode 506. Of course, it will be recognized that the present invention is not limited to the particular dimensions and configuration of the electrode assembly 504 described herein, and a variety of different configurations may be envisioned depending on the surgical application.

As shown, probe 500 includes a fluid lumen 520 passing through support member 502 to a distal opening (not shown) at the distal end of support member 502. Fluid lumen 520 is coupled to a supply of electrically conductive fluid, such as isotonic saline, or other suitable conductive fluid for delivery of such fluid to the target site. In the exemplary embodiment, probe 500 is designed such that lumen 520 will be positioned above electrode assembly 504 during use such that the conductive fluid exiting the distal opening of lumen 520 will naturally pass over return electrode 508 and active electrode 506 thereby creating a current path therebetween. In addition, the conductive fluid will be sufficient to cover the active electrode 506 such that the conditions for plasma formation can be met, as described in detail above.

Figure 26:
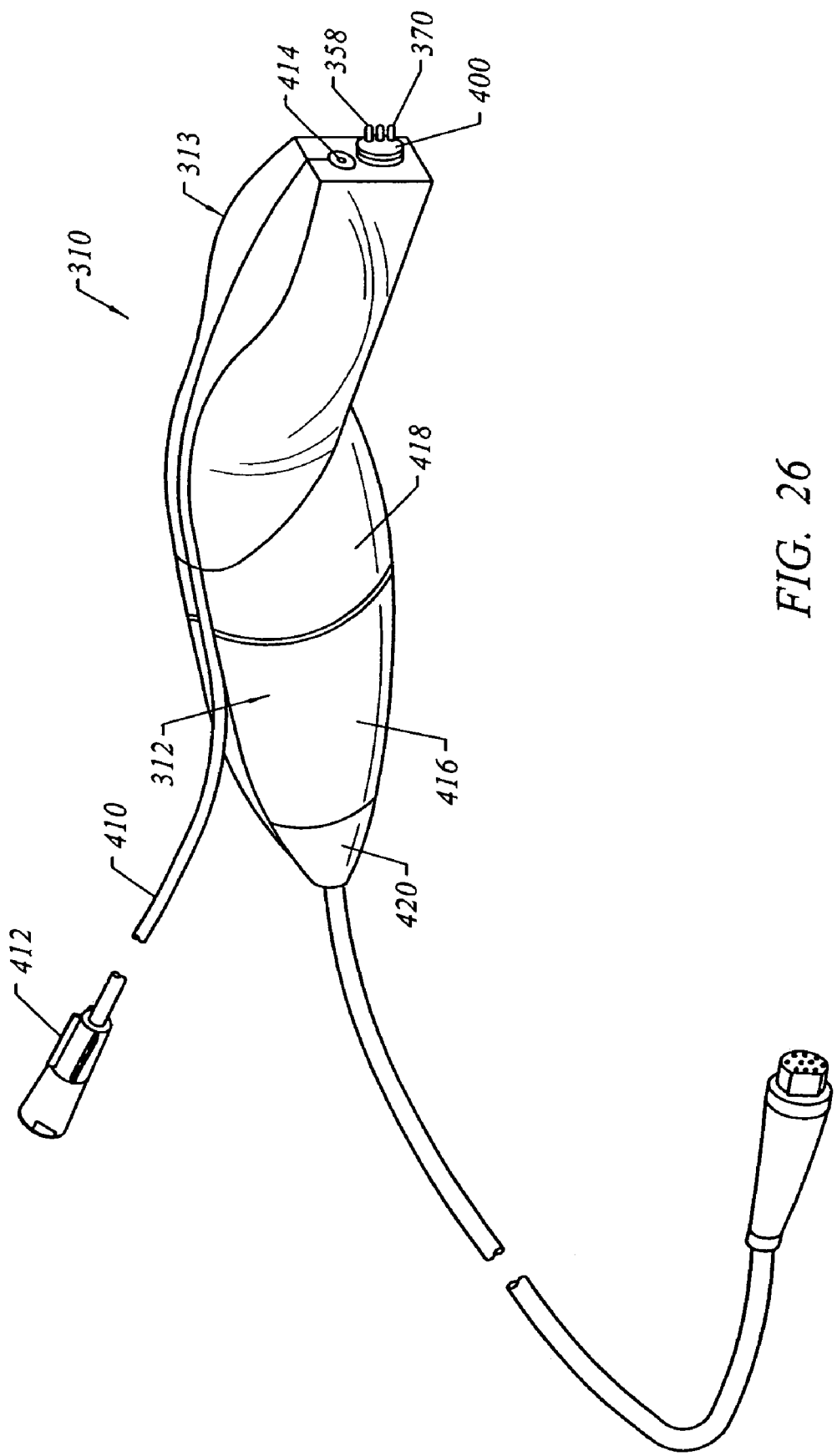
FIG. 26 is a perspective view of another embodiment of an electrosurgical probe for use in dermatology procedures.
Figure 27A:
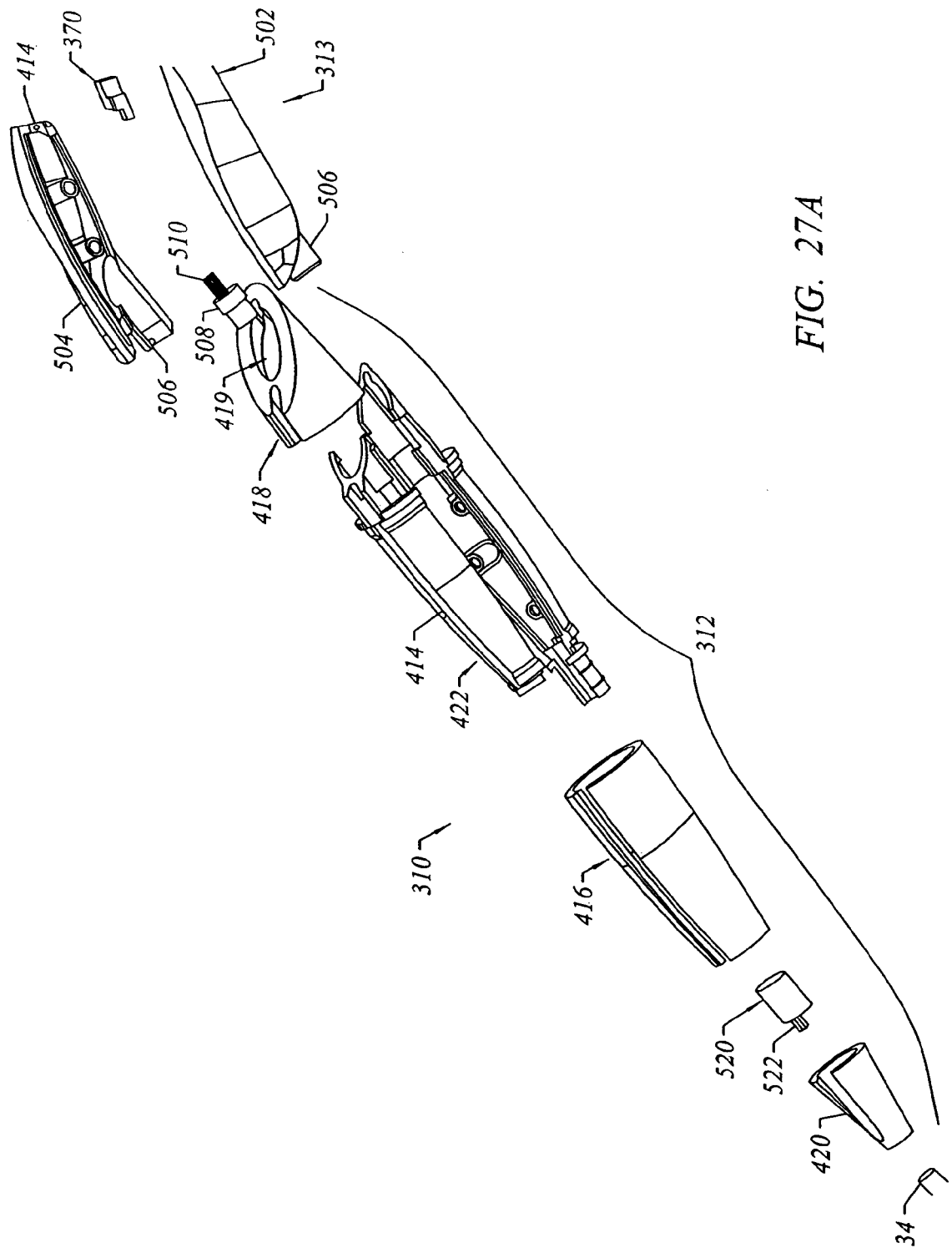
FIGS. 27A-27C are exploded, isometric views of the probe of FIG. 26.
Figure 27B:
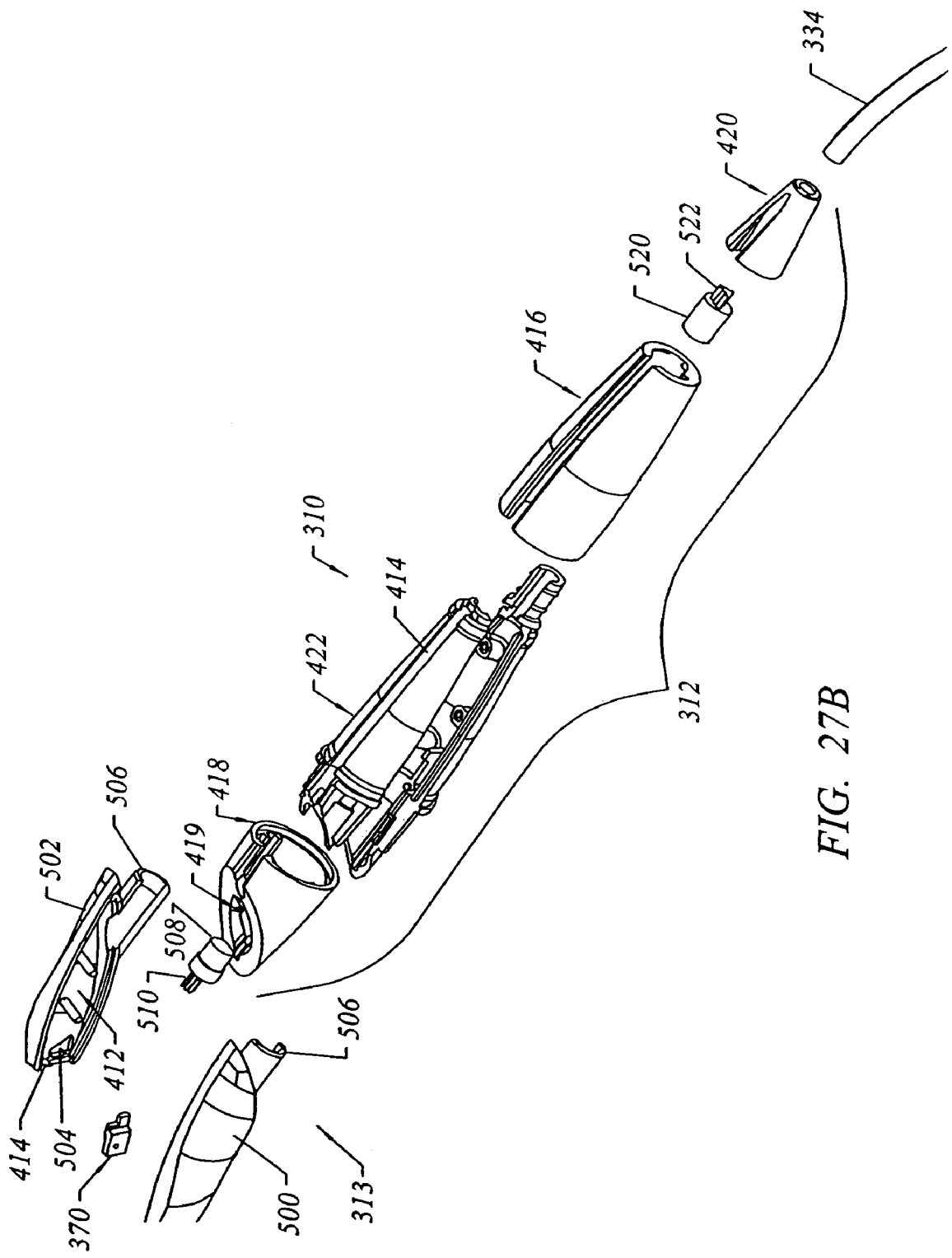

FIGS. 26, and 27A-C illustrate another exemplary electrosurgical probe 310 for cutting, incising, or removing tissue structures. Probe 310 comprises a shaft or disposable tip 313 removably coupled to a proximal handle 312, and an electrically insulating electrode support member 370 extending from tip 313 for supporting a plurality of active electrodes 358. Tip 313 and handle 312 typically comprise a plastic material that is easily molded into a suitable shape for handling by the surgeon. As shown in FIGS. 27A and 27B, handle 312 defines an inner cavity 372 that houses the electrical connections 374, and provides a suitable interface for connection to electrical connecting cable 22 (see FIG. 1). In the exemplary embodiment, handle 312 is constructed of a steam autoclavable plastic or metal (e.g., polyethylether ketone, or a stable metal alloy containing aluminum and/or zinc) so that it can be re-used by sterilizing handle 312 between surgical procedures. High service temperature materials are preferred, such as a silicone cable jacket and a polyetherimide handpiece or ULTEM® that can withstand repeated exposure to high temperatures.

Figure 27C:
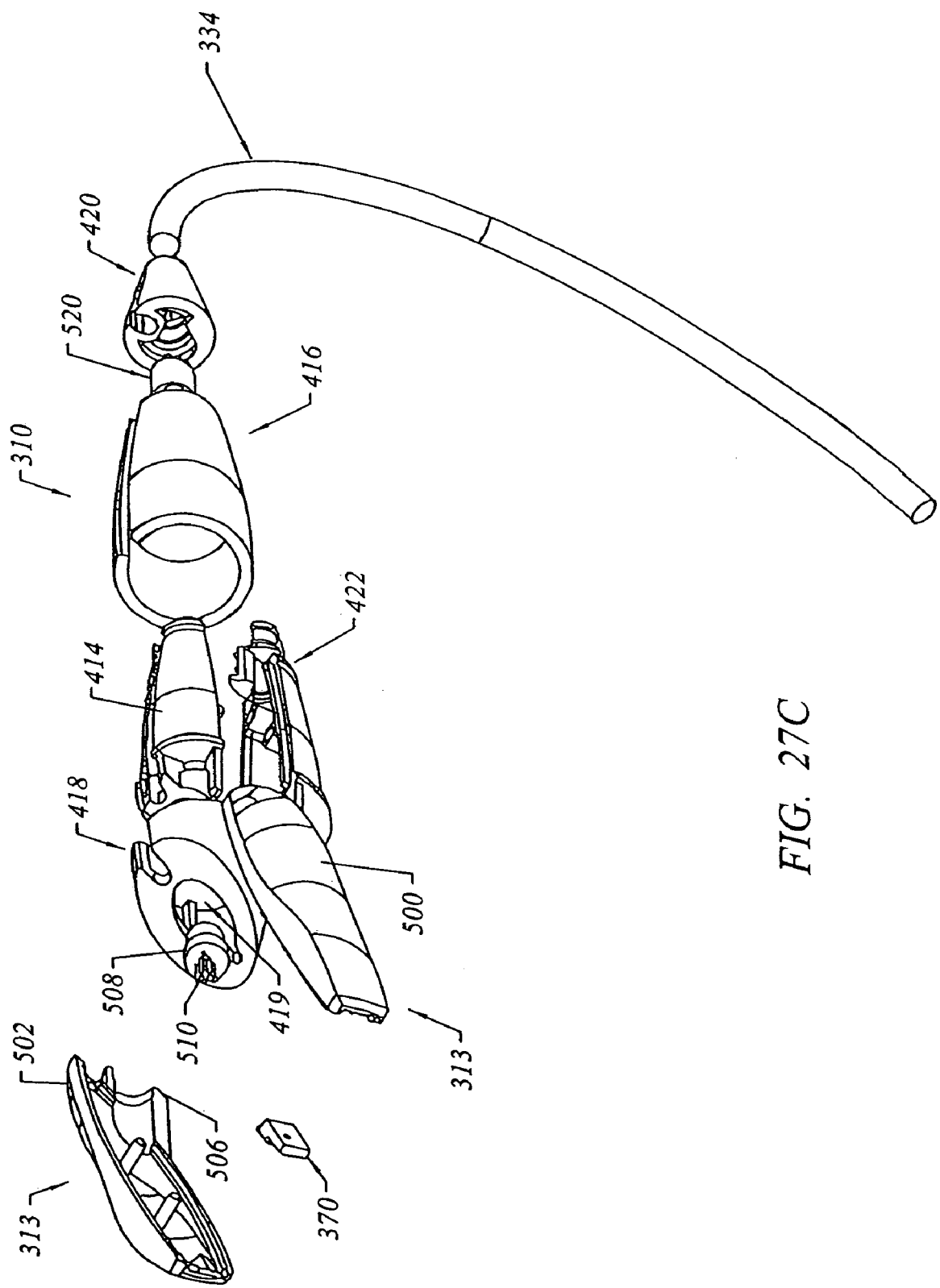

Referring to FIGS. 27A-27C, tip 313 preferably comprises first and second housing halves 500, 502 that snap fit together, and form a recess 404 therebetween for holding electrode support member 370 within the tip 313. Electrode support member 370 extends from the distal end of tip 313, usually by about 0.5 mm to 20 mm, and provides support for a plurality of electrically isolated active electrodes 358 and one or more return electrodes 400. Alternatively, electrode support member 370 may be recessed from the distal end of tip 313 to help confine the electrically conductive fluid around the active electrodes 358 during the surgical procedure, as discussed above. Electrode support member 370 has a substantially planar tissue treatment surface 380 that is usually disposed at an angle of about 10 to 90 degrees relative to the longitudinal axis of handle 312 to facilitate handling by the surgeon. In the exemplary embodiment, this function is accomplished by orienting tip 313 at an acute angle relative to the longitudinal axis of handle 312.

In the embodiment shown in FIGS. 26-27C, probe 310 includes a single annular return electrode 400 for completing the current path between active electrodes 358 and power supply 28 (see FIG. 1). As shown, return electrode 400 preferably has a fluid contact surface slightly proximal to tissue treatment surface 380, typically by about 0.1 mm to 2 mm, and preferably by about 0.2 mm to 1 mm. Return electrode 400 is coupled to a connector 404 that extends to the proximal end of handle 313, where it is suitably connected to power supply 28 (FIG. 1).

Referring again to FIGS. 27A-27C, tip 313 further includes a proximal hub 506 for supporting a male electrical connector 508 that holds a plurality of wires 510 each coupled to one of the active electrodes 358 or to return electrode 400 on support member 370. A female connector 520 housed within handle 312 is removably coupled to male connector 508, and a plurality of wires 522 extend from female connector 520 through a strain relief 524 to cable 334. Both sets of wires 510, 522 are insulated to prevent shorting in the event of fluid ingress into the probe 310. This design allows for removable connection of the electrodes in tip 313 with the connector 520 within handle 312 so that the handle can be re-used with different tips 313. Probe 310 will preferably also include an identification element, such as a coded resistor (not shown), for programming a particular voltage output range and mode of operation for the power supply. This allows the power supply to be employed with a variety of different probes for a variety of different applications.

In the representative embodiment, probe 310 includes a fluid tube 410 (FIG. 26) for delivering electrically conductive fluid to the target site. Fluid tube 410 is sized to extend through a groove 414 in handle 313 and through an inner cavity 412 in tip 312 to a distal opening 414 (FIG. 26) located adjacent electrode support member 370. Tube 410 extends all the way through inner cavity 412 to opening 414 to eliminate any possible fluid ingress into cavity 412. Fluid tube 410 includes a proximal connector for coupling to an electrically conductive fluid source 321.

Probe 310 will also include a valve or equivalent structure for controlling the flow rate of the electrically conductive fluid to the target site. In the representative embodiment shown in FIGS. 27A-27C, handle 312 comprises a main body 422 coupled between distal hub 418 and strain relief 420, and a rotatable sleeve 416 around main body 422. Distal hub 418 has an opening 419 for receiving proximal hub 506 of tip 313 for removably coupling the tip 313 to the handle 312. Sleeve 416 is rotatably coupled to strain relief 420 and distal hub 418 to provide a valve structure for fluid tube 410. As shown in FIG. 27A, fluid tube 410 extends through groove 414 from strain relief 420, through main body 422 and distal hub 420 to tip 313. Rotation of sleeve 416 will impede, and eventually obstruct, the flow of fluid through tube 410. Of course, this fluid control may be provided by a variety of other input and valve devices, such as switches, buttons, etc.

In alternative embodiments, the fluid path may be directly formed in probe 310 by, for example, a central inner lumen or an annular gap (not shown) within the handle and the tip. This inner lumen may be formed near the perimeter of the probe 310 such that the electrically conductive fluid tends to flow radially inward towards the target site, or it may be formed towards the center of probe 310 so that the fluid flows radially outward. In addition, the electrically conductive fluid may be delivered from a fluid delivery element (not shown) that is separate from probe 310. In arthroscopic surgery, for example, the body cavity will be flooded with isotonic saline and the probe 310 will be introduced into this flooded cavity. Electrically conductive fluid will be continually resupplied to maintain the conduction path between return electrode 400 and active electrodes 358. A more complete description of alternative electrosurgical probes incorporating one or more fluid lumen(s) can be found in commonly assigned, co-pending application Ser. No. 08/485,219, filed on Jun. 7, 1995, the complete disclosure of which is incorporated herein by reference.

Referring now to FIG. 26, electrically isolated active electrodes 358 are spaced apart over tissue treatment surface 380 of electrode support member 370, preferably in a linear array. In the representative embodiment, three active electrodes 358, each having a substantially conical shape, are arranged in a linear array extending distally from surface 380. Active electrodes 358 will usually extend a distance of about 0.5 mm to 20 mm from tissue treatment surface 380, preferably about 1 mm to 5 mm. Applicant has found that this configuration increases the electric field intensities and associated current densities at the distal edges of active electrodes 358, which increases the rate of tissue cutting. In the representative embodiment, the tissue treatment surface 380 has a circular cross-sectional shape with a diameter in the range of about 0.5 mm to 20 mm (preferably about 2 mm to 10 mm). The individual active electrodes 358 preferably taper outward as shown, or they may form a distal edge, such as the electrodes shown in FIGS. 3 and 24.

Figure 28:
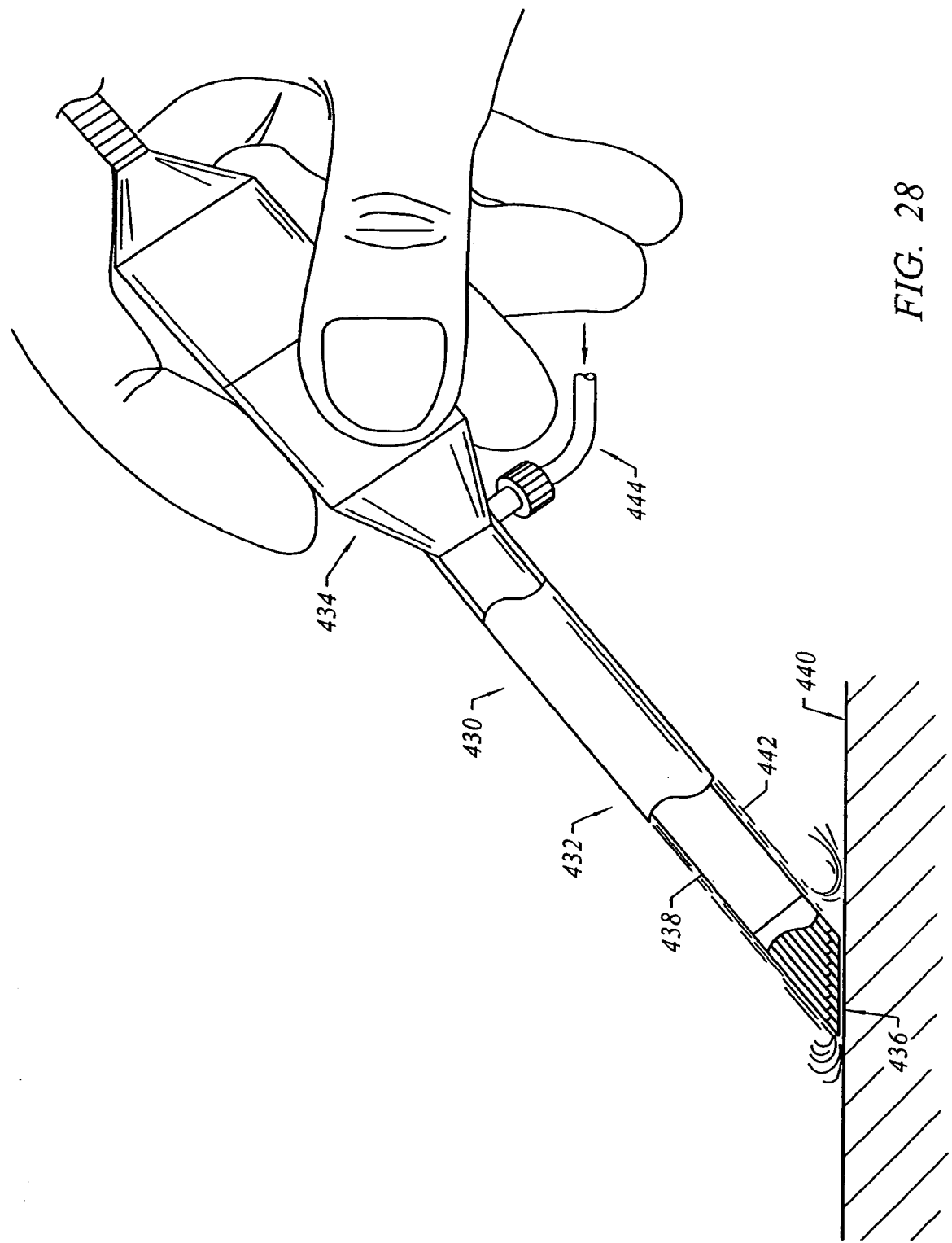
FIG. 28 is a cross-sectional view of another alternative electrosurgical probe.

Probe 430 of FIG. 28 includes a shaft 432 coupled to a proximal handle 434 for holding and controlling shaft 432. Probe 430 includes an active electrode array 436 at the distal tip of shaft 432, an annular return electrode 438 extending through shaft 432 and proximally recessed from the active electrode array 436, and an annular lumen 442 between return electrode 438 and an outer insulating sheath 446. Probe 430 further includes a liquid supply conduit 444 attached to handle 434 and in fluid communication with lumen 442, and a source of electrically conductive fluid (not shown) for delivering the fluid past return electrode 438 to the target site on the tissue 440. Electrode array 436 is preferably flush with the distal end of shaft 432 or distally extended from the distal end by a small distance (on the order of 0.005 inches) so as to minimize the depth of ablation. Preferably, the distal end of shaft 432 is beveled to improve access and control of probe 430 while treating the target tissue.

Figure 29:
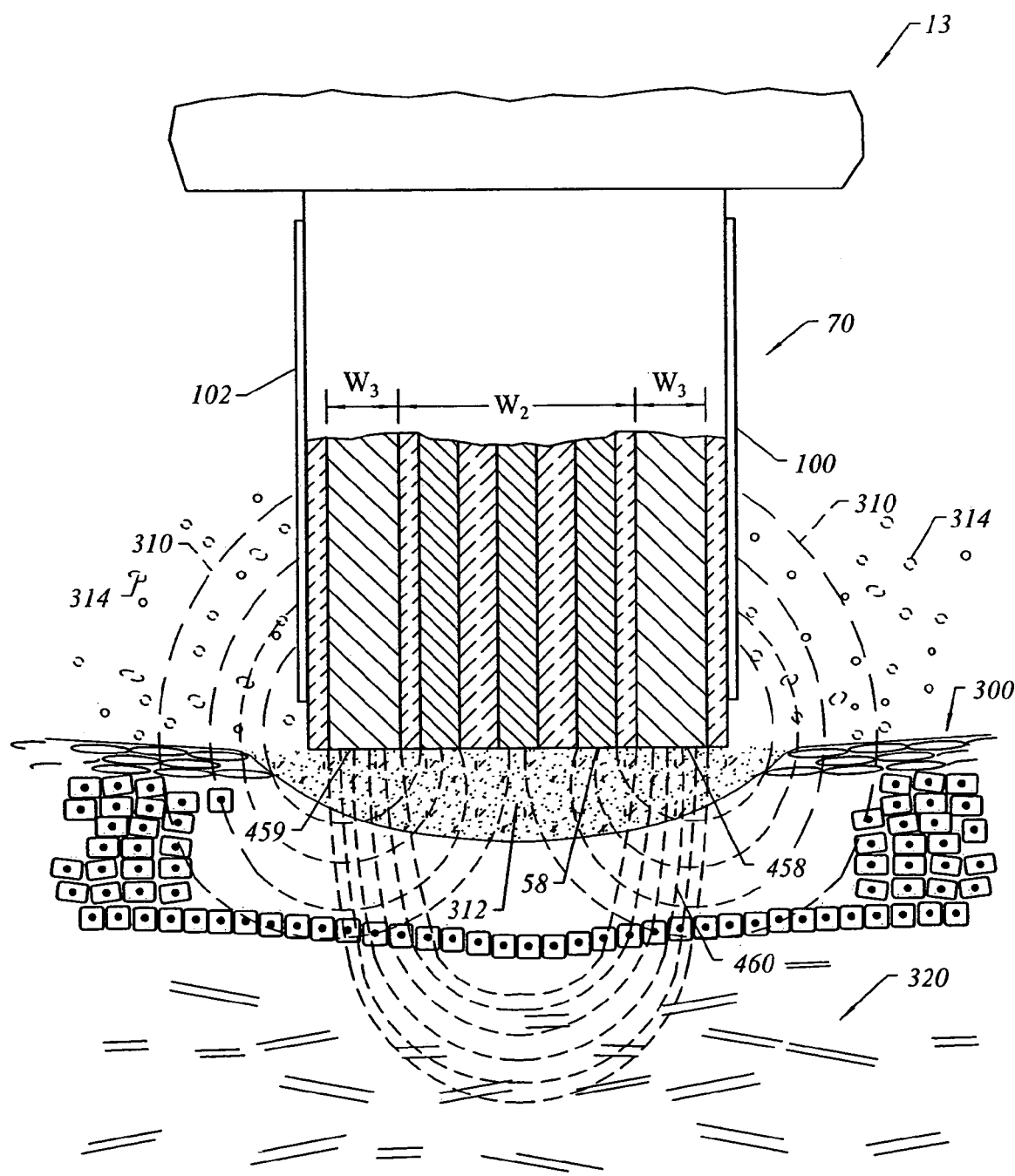
FIG. 29 illustrates another embodiment of the electrosurgical probe of the present invention, incorporating additional active electrodes.

Yet another embodiment of the present invention is shown in FIG. 29. Auxiliary active electrodes 458, 459 are positioned at the distal tip 70 of the probe. Auxiliary active electrodes 458, 459 may be the same size as ablation active electrodes 58, or larger as shown in FIG. 29. One operating arrangement is to connect auxiliary active electrodes 458, 459 to two poles of a high frequency power supply to form a bipolar circuit allowing current to flow between the terminals of auxiliary active electrodes 458, 459 as shown by current flux lines 460. Auxiliary active electrodes 458, 459 are electrically isolated from ablation electrodes 58. By proper selection of the inter-electrode spacing, $W_2$, and electrode width, $W_3$, and the frequency of the applied voltage, the current flux lines 460 can be caused to flow below the target layer as described above.

The voltage will preferably be sufficient to establish high electric field intensities between the active electrode array 436 and the target tissue 440 to thereby induce molecular breakdown or disintegration of several cell layers of the target tissue. As described above, a sufficient voltage will be applied to develop a thin layer of vapor within the electrically conductive fluid and to ionize the vaporized layer or region between the active electrode(s) and the target tissue. Energy in the form of charged particles are discharged from the vapor layer to ablate the target tissue, thereby minimizing necrosis of surrounding tissue and underlying cell layers.

Figure 30:
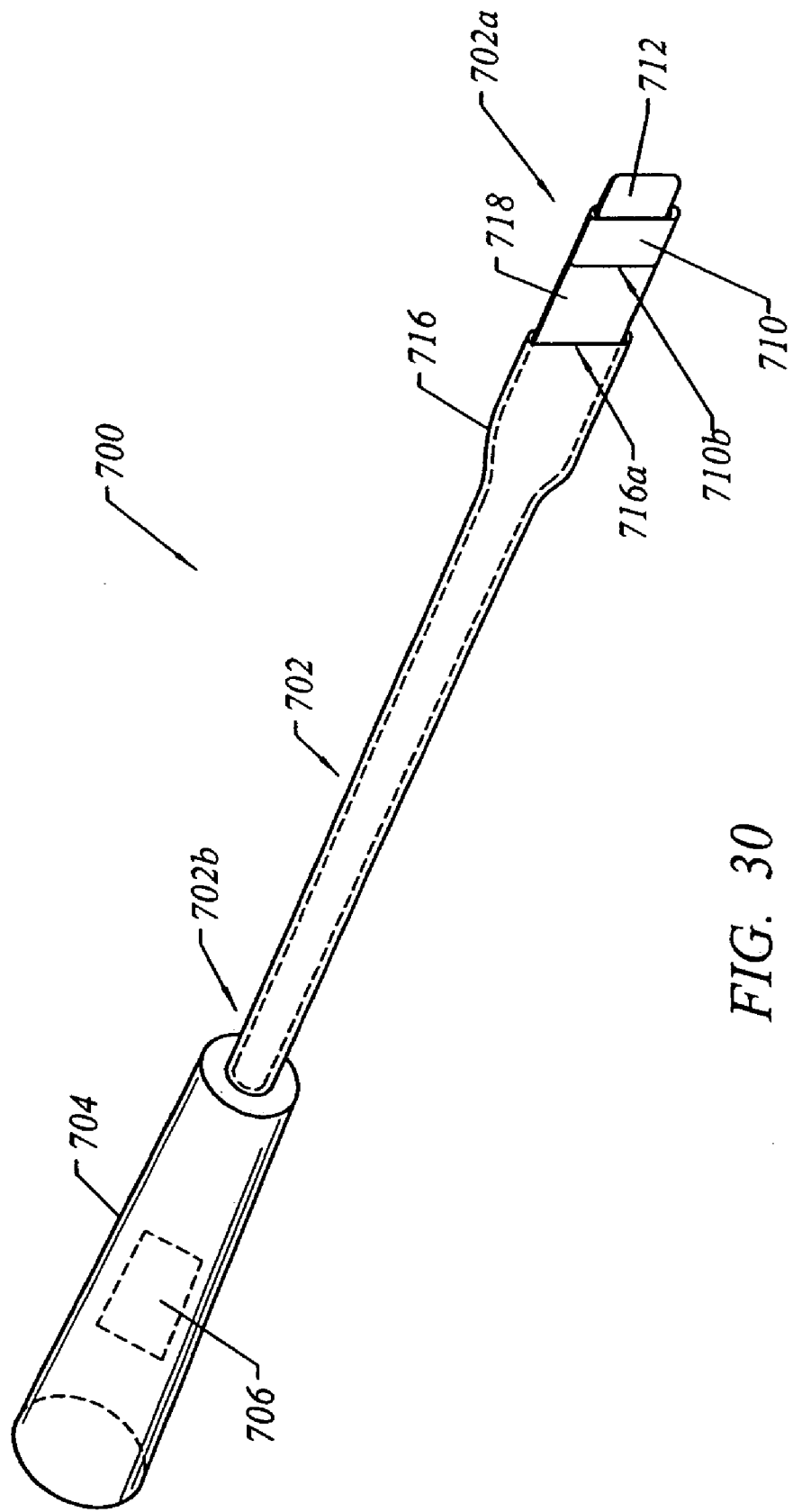
FIG. 30 is a perspective view of an electrosurgical probe having a blade electrode.

With reference to FIG. 30, there is shown in perspective view an electrosurgical probe 700, according to another embodiment of the invention. Probe 700 includes a shaft 702 having a shaft distal end portion 702a and a shaft proximal end portion 702b. Shaft 702 is affixed at its proximal end 702b to a handle 704. Shaft 702 typically comprises an electrically conductive material, usually a metal, such as tungsten, stainless steel, platinum or its alloys, titanium or its alloys, molybdenum or its alloys, nickel or its alloys. An electrically insulating electrode support 710 is disposed at shaft distal end 702a. An active electrode 712 is disposed on electrode support 710. Active electrode 712 comprises a blade electrode (e.g., FIGS. 31A, 31B). An electrically insulating sleeve 716 covers a portion of shaft 702, and terminates at sleeve distal end 716a to define an exposed portion of shaft 702 extending between electrode support proximal end 710b and sleeve distal end 716a. This exposed portion of shaft 702 defines a return electrode 718 on shaft distal end portion 702a. (In an alternative embodiment, the return electrode may take the form of an annular band of an electrically conductive material, e.g., a platinum alloy, disposed on the exterior of the shaft distal end.) A cavity within handle 704 accommodates a connection block 706, which is connected to active electrode 712 and return electrode 718 via electrode leads (not shown). Connection block 706 provides a convenient mechanism for coupling active electrode 712 and return electrode 718 to opposite poles of a power supply (e.g., power supply 28, FIG. 1).

Figure 31A:
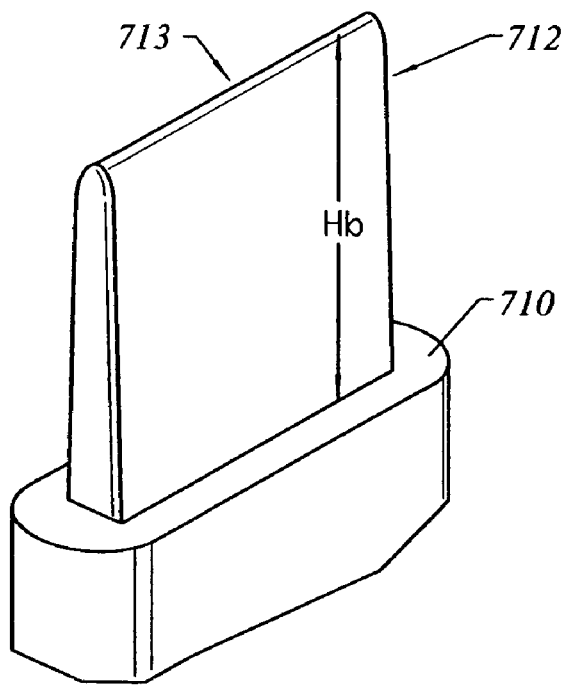
FIG. 31A is a perspective view.

FIG. 31A is a perspective view of an active electrode 712 of probe 700, according to one embodiment of the invention. Active electrode 712 is in the form of a single blade electrode which extends from electrode support 710 to a distance, $H_b$. The distance $H_b$ may vary, for example, according to the intended applications of probe 700, and the value of $H_b$ is at least to some extent a matter of design choice. Typically, for a broad array of electrosurgical procedures, the distance $H_b$ is in the range of from about 0.02 mm to about 5 mm. Active electrode 712 includes an active edge 713 which is adapted for generating high current densities thereat upon application of a high frequency voltage from the power supply between active electrode 712 and return electrode 718. In this way, active edge 713 can efficiently effect localized ablation of tissues via molecular dissociation of tissue components which contact, or are in close proximity to, active edge 713. A process for ablation of tissues via molecular dissociation of tissue components has been described hereinabove.

Figure 31B:
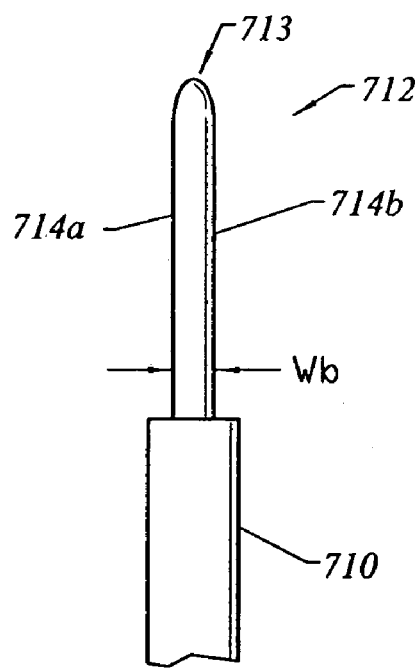
FIG. 31B is a lateral view, of a blade electrode, according to one embodiment of the invention.

As best seen in FIG. 31B, the blade-like active electrode 712 further includes first and second blade sides, 714a, 714b, respectively. First and second blade sides 714a, 714b are separated by a maximum distance, $W_b$. The distance $W_b$ is typically in the range of from about 0.1 mm to about 2.5 mm. In the embodiment of FIG. 31B, first and second blade sides 714a, 714b are substantially parallel to each other. Each of first and second blade sides 714a, 714b are adapted for engaging tissue severed, ablated, or otherwise modified by active edge 713, and for coagulating tissue engaged by first blade side 714a and/or second blade side 714b. In this way, active electrode 712 can precisely and effectively sever, ablate, or otherwise modify a target tissue with active edge 713 to form a first-modified tissue, and at the same time, or shortly thereafter, further modify the first-modified tissue by means of first and second blade sides 714a, 714b. For example, active edge 713 can make an incision in a target tissue via localized molecular dissociation of target tissue components, while first and second blade sides 714a, 714b can effect hemostasis in the severed tissue.

Figure 32A:
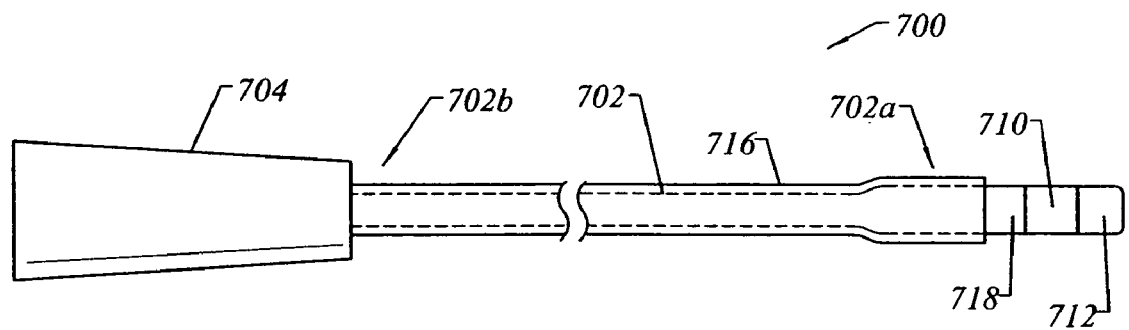
FIGS. 32A, 32B, and 32C are a side view, a plan view, and an end view, respectively, of an electrosurgical probe having a blade electrode.
Figure 32B:
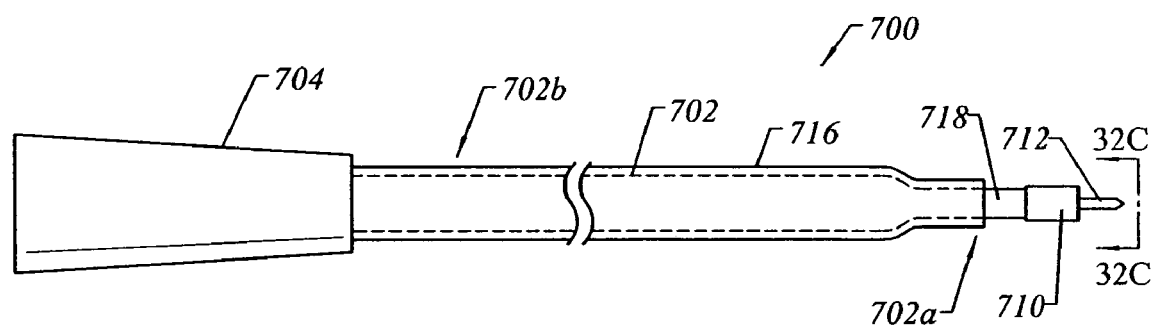
Figure 32C:
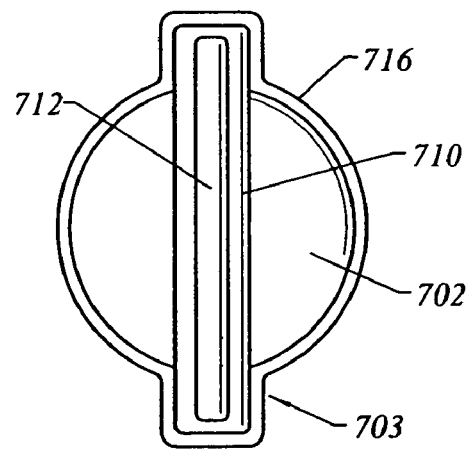

FIGS. 32A, 32B, and 32C are a side view, a plan view, and an end view, respectively, of electrosurgical probe 700 having a blade-like active electrode 712, according to one embodiment of the invention. In the embodiment of FIGS. 32A-C, electrode support 710 is disposed at the terminus of shaft 702, and active electrode 712 is affixed to support distal end 710a (e.g., FIG. 33A). However, other arrangements for electrode support 710 and active electrode 712 are within the scope of the invention (e.g., FIGS. 34A-C, 35A-C). Active electrode 712 is in the form of a substantially flat metal blade. Active electrode 712 is shown as being substantially rectangular as seen from the side (FIG. 32A). However, various other shapes for active electrode 712 are within the scope of the invention (e.g., FIGS. 33C-E). FIG. 32C is an end view of probe 700 as seen along the lines 32C-32C of FIG. 32B, showing a laterally compressed region 703 of shaft 702. Laterally compressed region 703 may be adapted for housing electrode support 710. Laterally compressed region 703 may also facilitate manipulation of shaft distal end portion 702a of probe 700 during various surgical procedures, particularly in situations where accessibility of a target tissue is restricted.

Figure 33A:
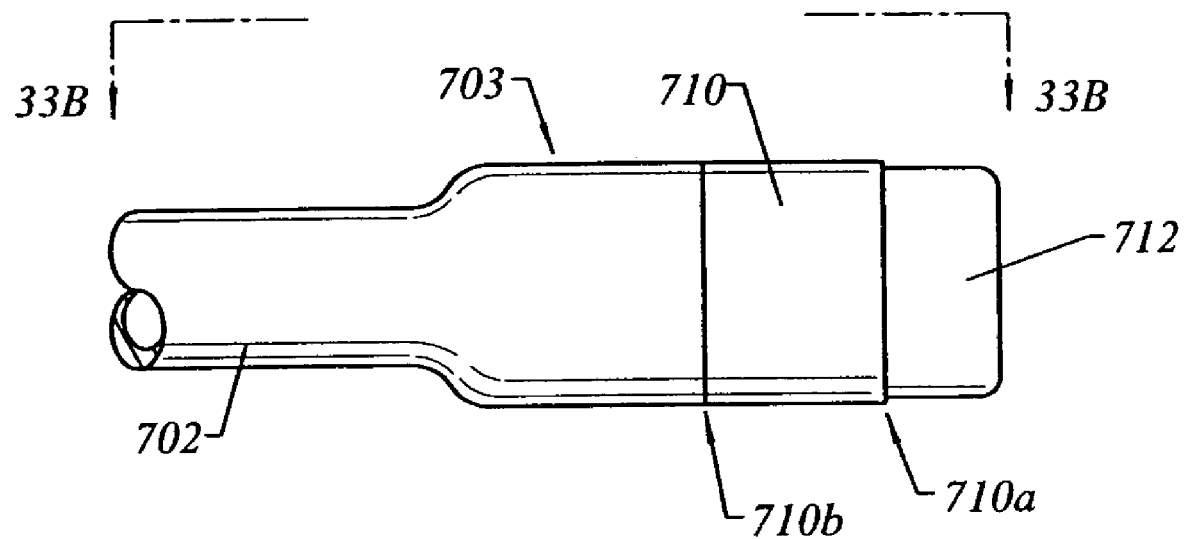
FIGS. 33A and 33B are a side view and a plan view, respectively, of the distal end of an electrosurgical probe having a terminal blade electrode, according to one embodiment of the invention.
Figure 33B:
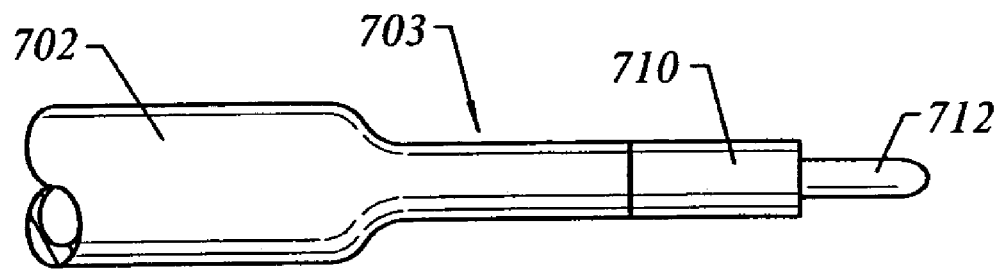

FIGS. 33A and 33B are a side view and a plan view, respectively, of the distal end of probe 700, showing details of shaft distal end portion 702a and terminally disposed blade active electrode 712, according to one embodiment of the invention. Blade electrode 712 is substantially rectangular in shape as seen from the side (FIG. 33A). The distal end of shaft 702 includes laterally compressed region 703. As seen from the side (FIG. 33A), laterally compressed region 703 appears wider than more proximal portions of shaft 702. FIG. 33B is a plan view of probe 700 as seen along the lines 33B-33B of FIG. 33A, in which laterally compressed region 703 appears narrower than more proximal portions of shaft 702. Electrode support 710 is mounted to the distal end of laterally compressed region 703. Typically, electrode support 710 comprises a durable, electrically insulating, refractory material having a certain amount of flexibility. For example, electrode support 710 may comprise a material such as a silicone rubber, a polyimide, a fluoropolymer, a ceramic, or a glass.

Figure 33C:
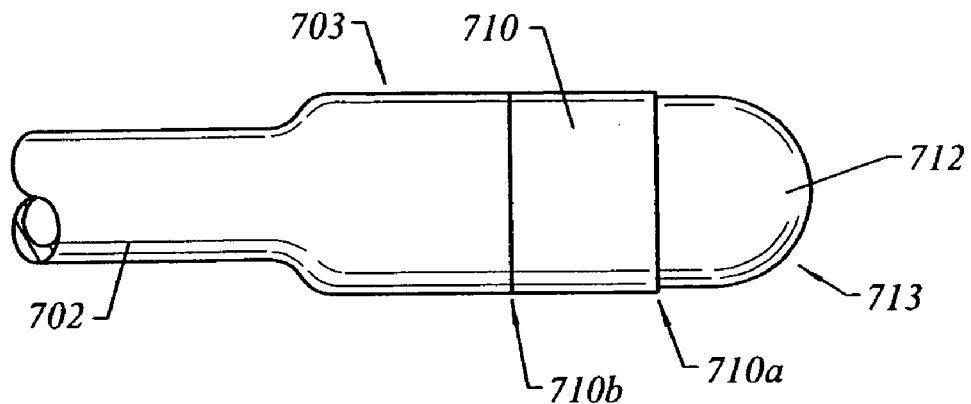
FIGS. 33C-33E each show a side view of the distal end of an electrosurgical probe having a terminal blade electrode, according to three different embodiments of the invention.
Figure 33D:
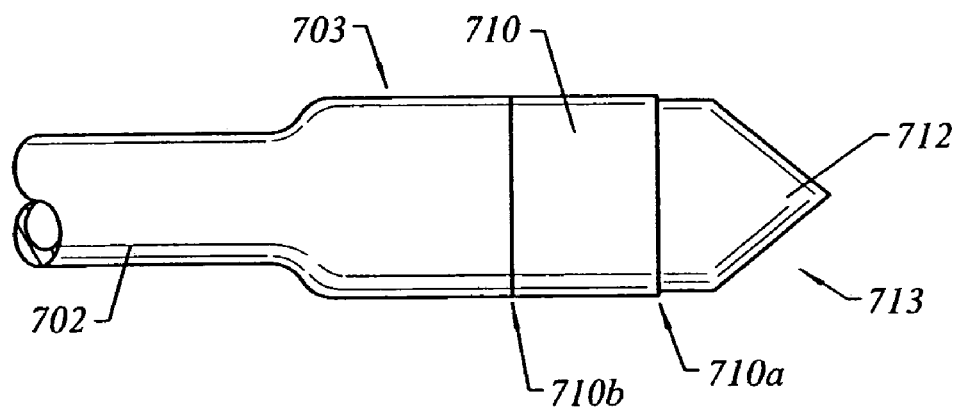
Figure 33E:
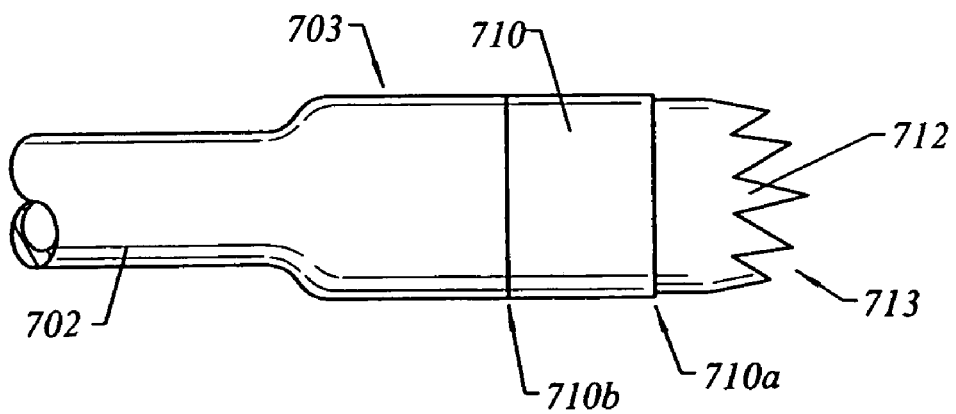

FIGS. 33C-33E each show a side view of the distal end of probe 700 having a terminal blade active electrode 712, according to three different embodiments of the invention. Electrode support 710 is mounted terminally on shaft 702, and includes a support distal end 710a and a support proximal end 710b. In the embodiment of FIG. 33C, active edge 713 of active electrode 712 is arcuate, convex, or substantially semi-circular in shape. In the embodiment of FIG. 33D, active electrode 712 has a pointed active edge 713, while in the embodiment of FIG. 33E, the active edge 713 of active electrode 712 is serrated.

Figure 34A:
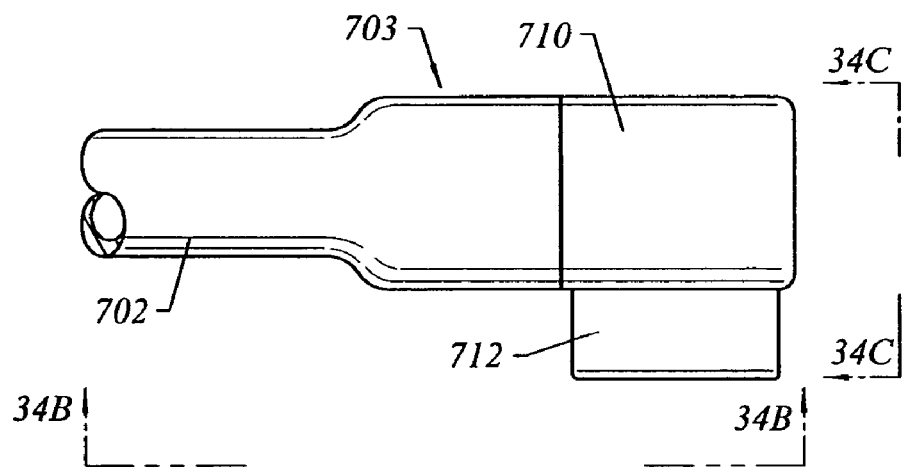
FIGS. 34A, 34B, and 34C are a side view, a plan view, and an end view, respectively, of an electrosurgical probe having a terminal electrode support and a lateral blade electrode, according to another embodiment of the invention.
Figure 34B:
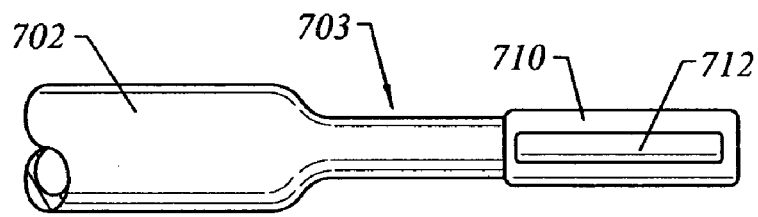
Figure 34C:
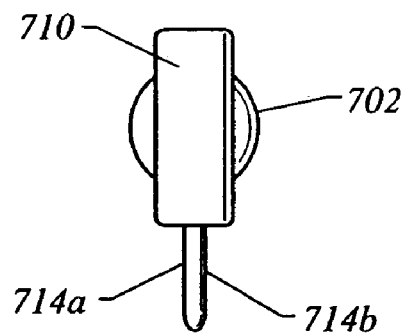

FIG. 34A shows in side view an electrosurgical probe 700 having electrode support 710 mounted terminally on shaft 702 and blade active electrode 712 disposed laterally on electrode support 710, according to another embodiment of the invention. FIG. 34B is a plan view of probe 700 taken along the lines 34B-34B of FIG. 34A. FIG. 34C is an end view taken along the lines 34C-34C of FIG. 34A. In the embodiments of FIGS. 34A-C, electrode 712 is in the form a substantially flat, metal blade having first and second blade sides 714a, 714b, substantially parallel to each other. First and second blade sides 714a, 714b are adapted for engaging and coagulating severed or modified tissue, as described hereinabove.

Figure 35A:
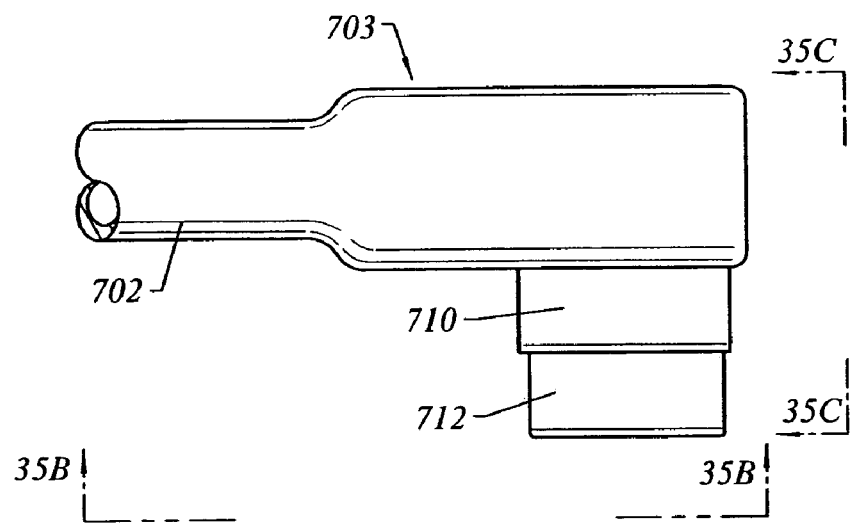
FIGS. 35A, 35B, and 35C are a side view, a plan view, and an end view, respectively, of an electrosurgical probe having a lateral electrode support and a lateral blade electrode, according to another embodiment of the invention.
Figure 35B:
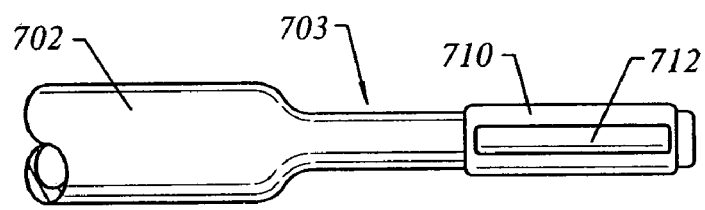
Figure 35C:
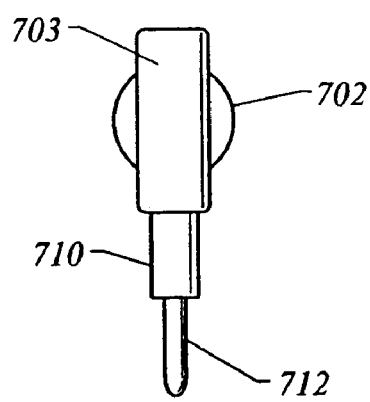

FIG. 35A shows in side view an electrosurgical probe 700 having electrode support 710 mounted laterally on the distal end of shaft 702, according to another embodiment of the invention. Blade active electrode 712 is mounted laterally on electrode support 710. FIG. 35B is a plan view of probe 700 taken along the lines 35B-35B of FIG. 35A. FIG. 35C is an end view taken along the lines 35C-35C of FIG. 35A. Active electrode 712 is in the form a substantially flat, metal blade having first and second blade sides 714a, 714b, substantially parallel to each other. Electrode support 710 is mounted laterally on laterally compressed region 703 of shaft 702.

Figure 36A:
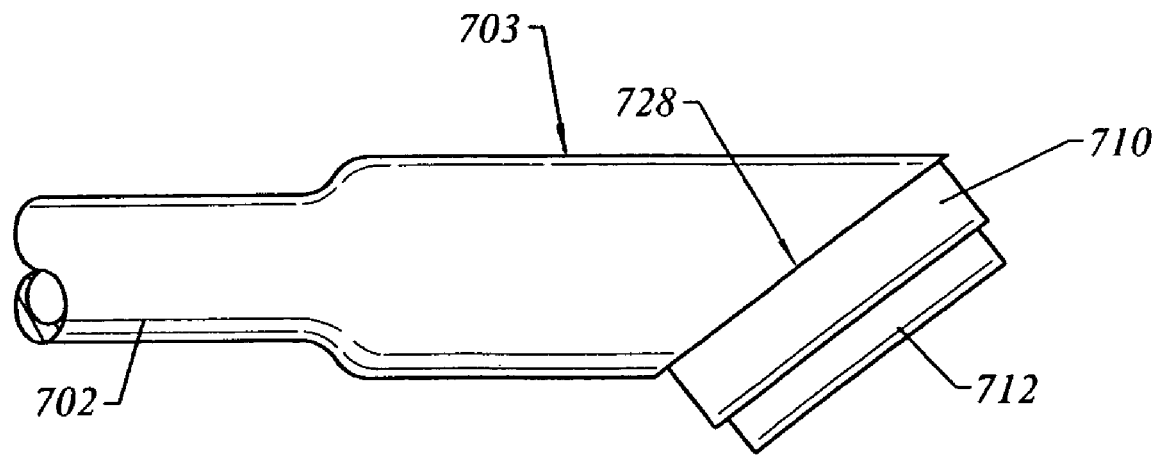
FIGS. 36A and 36B each show a side view of the distal end of an electrosurgical probe having a blade electrode, according to two different embodiments of the invention.
Figure 36B:
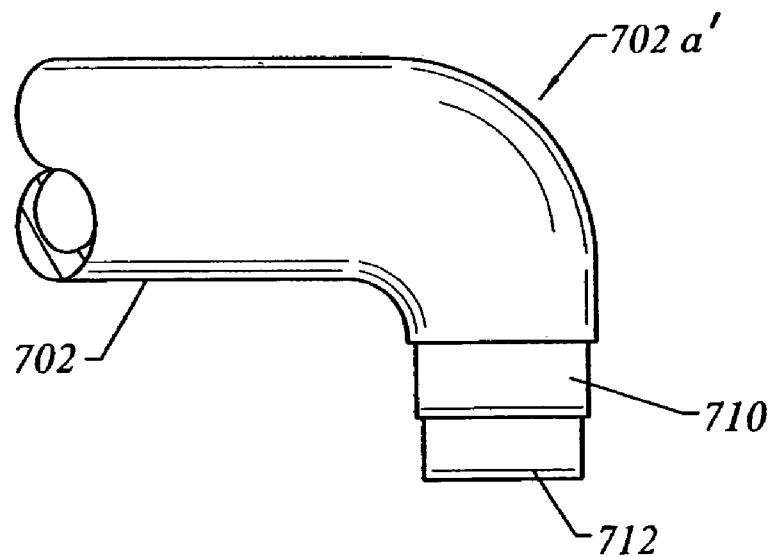

FIG. 36A shows a side view of the distal end of an electrosurgical probe 700, wherein shaft 702 includes a beveled end 728 to which electrode support 710 is mounted. Blade active electrode 712 is disposed on electrode support 710. The arrangement of electrode support 710 and electrode 712 on beveled end 728 may facilitate access of shaft distal end portion 702a in general, and of electrode 712 in particular, to a target tissue during various surgical procedures, particularly in situations where accessibility is restricted. FIG. 36B shows a side view of the distal end of an electrosurgical probe 700, according to another embodiment of the invention. Shaft 702 includes a curved distal end 702a'. Electrode support 710 is mounted on distal end 702a', and blade active electrode 712 is affixed to electrode support 710. Curved distal end 702a' facilitates access of electrode 712 to a target tissue during various surgical procedures.

Although in the embodiments of FIGS. 34A-C, 35A-C, and 36A-B active electrode 712 is shown as being substantially rectangular, this representation should not be construed as limiting these embodiments to a rectangular active electrode 712. Indeed, each of the embodiments of FIGS. 34A-C, 35A-C, and 36A-B may have an active electrode 712 in a broad range of shapes, including those represented in FIGS. 33C-E.

Figure 37A:
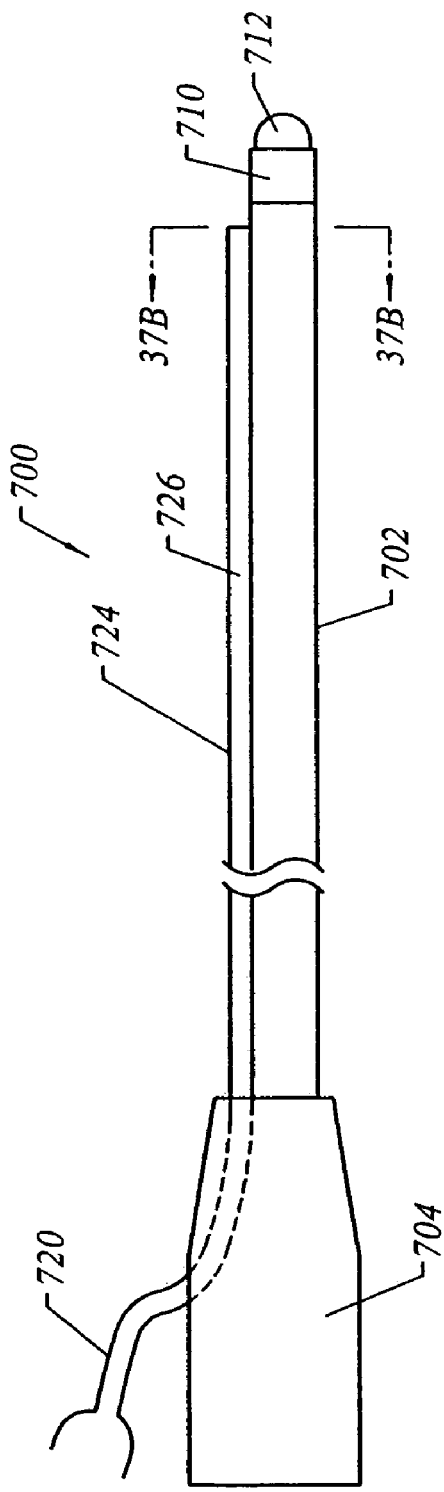
FIGS. 37A, and 37B are a side view and an end view, respectively, of an electrosurgical probe having a lumen external to the probe shaft, according to one embodiment of the invention.
Figure 37B:
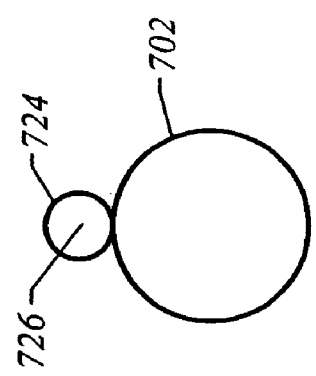

FIG. 37A shows in side view an electrosurgical probe 700 having an exterior tube 724 arranged on shaft 702 and coupled at its proximal end to a connection tube 720 at handle 704. Exterior tube 724 may comprise a plastic tube of suitable length commensurate with the size of probe 700. Exterior tube 724 defines a lumen 726, and typically terminates at shaft distal end 702a at a location somewhat proximal to electrode support 710. In some embodiments, probe 700 may include two or more exterior tubes 724, each exterior tube 724 having lumen 726. Each lumen 726 may serve as a conduit for an aspiration stream, or as a conduit for delivery of an electrically conductive fluid to the shaft distal end, generally as described hereinabove. FIG. 37B is an end view of probe 700 taken along the lines 37B-37B of FIG. 37A, showing exterior tube 724 and lumen 726 in relation to shaft 702. The diameter of exterior tube 724 is, at least to some extent, a matter of design choice. Exterior tube 724 may comprise a substantially rigid or somewhat flexible plastic tube comprising polyethylene, a polyimide, a fluoropolymer, and the like.

FIG. 38A shows, in side view, an electrosurgical probe 700 having an outer sheath 722 surrounding the exterior of a portion of shaft 702, according to another embodiment of the invention. Outer sheath 722 is coupled at its proximal end to a connection tube 720 at handle 704. Outer sheath 722 may comprise a plastic tube of suitable length and having a diameter larger than that of shaft 702. Together with the exterior of shaft 702, outer sheath 722 defines a lumen 726' in the form of an annular void. Typically, outer sheath 722 terminates at shaft distal end 702a at a location proximal to electrode support 710. Lumen 726' typically serves as a conduit for delivery of an electrically conductive fluid to the shaft distal end. FIG. 38B is an end view of probe 700 taken along the lines 38B-38B of FIG. 38A, showing outer sheath 722 and lumen 726' in relation to shaft 702. The diameter of outer sheath 722 is, at least to some extent, a matter of design choice. Outer sheath 722 may comprise a substantially rigid or somewhat flexible plastic tube comprising polyethylene, a polyimide, and the like.

Figure 39A:
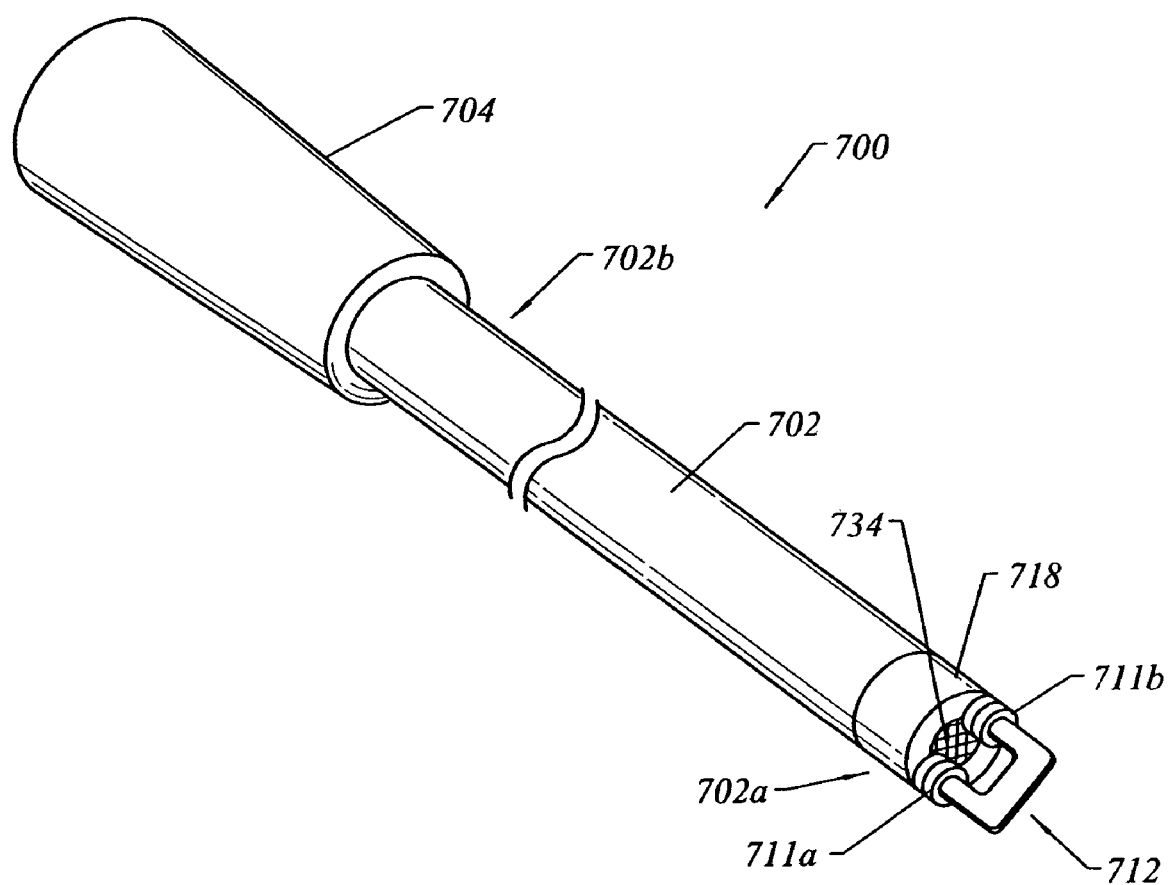
FIGS. 39A, 39B, and 39C schematically represent a perspective view, a longitudinal sectional view, and an end view, respectively, of an electrosurgical probe, according to another embodiment of the invention.

FIG. 39A schematically represents an electrosurgical probe 700, according to another embodiment of the invention. Probe 700 includes shaft 702 and handle 704 affixed at shaft proximal end 702b. A first electrode support 711a and a second electrode support 711b are disposed at shaft proximal end 702a. A blade active electrode 712 is arranged on first and second electrode supports, 711a, 711b. Each of first and second electrode supports 711a, 711b may comprise a refractory and electrically insulating material, such as a silicone rubber or the like, as described hereinabove. A return electrode 718 is located at shaft distal end 702 proximal to first and second electrode supports 711a, 711b. Return electrode 718 may comprise an exposed portion of shaft distal end 702a (e.g., FIGS. 32A-C). Blade active electrode 712 typically extends distally from electrode support 710 by a distance in the range of from about 0.1 mm to about 10 mm, an more typically from about 2 mm to 10 mm.

Blade active electrode 712 and return electrode 718 may be independently coupled to opposite poles of a high frequency power supply via electrode leads (not shown) and a connection block (e.g., FIG. 30). In one embodiment, an active electrode lead is coupled to one of first and second electrode arms 715a, 715b, and the other arm terminates in a free, electrically isolated end, for example, within first electrode support 711a or second electrode support 711b. Blade active electrode 712 includes a crosspiece 715c (FIGS. 39B-D) located distal to aspiration port 734. A fluid delivery element or unit including an outer sheath 722' (e.g., FIG. 39B) is omitted from FIG. 39A for the sake of clarity.

Figure 39B:
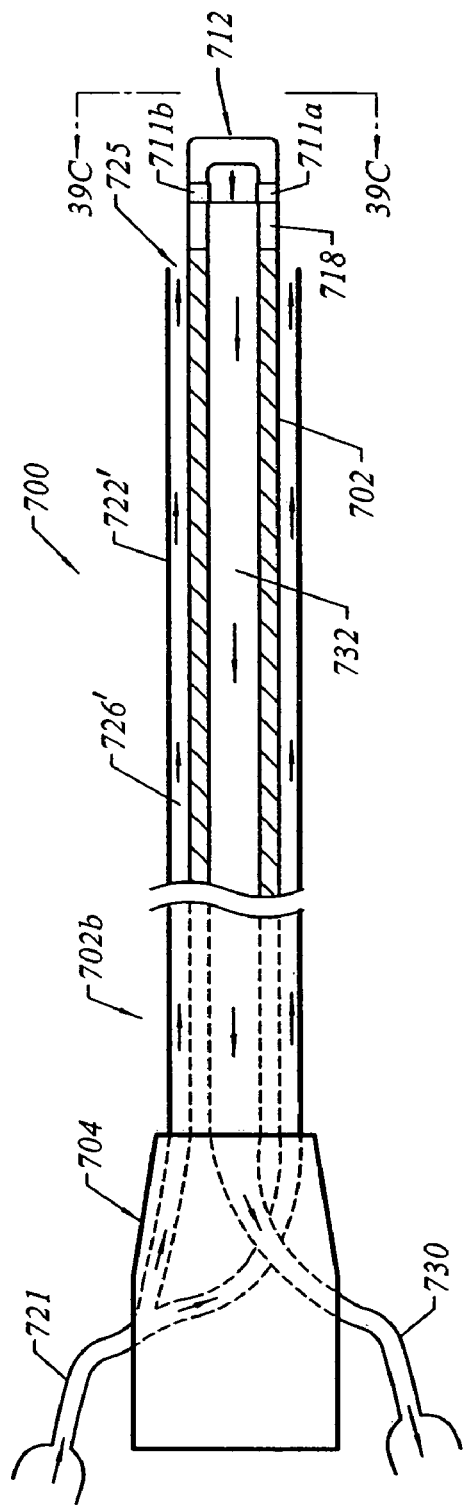

FIG. 39B is a partial sectional view of probe 700 of FIG. 39A as seen from the side. Outer sheath 722' defines an annular fluid delivery lumen 726' between sheath 722' and shaft 702. Lumen 726' terminates in an annular fluid delivery port 725 at shaft distal end 702a. Fluid delivery lumen 726' is in communication proximally with a fluid delivery tube 721. Solid arrows indicate the direction of flow of an electrically conductive fluid (e.g., isotonic saline) within fluid delivery lumen 726'. An aspiration device of probe 700 includes aspiration port 734 in communication with an aspiration lumen 732 and an aspiration tube 730. Solid arrows within aspiration lumen 732 indicate the direction of flow of an aspiration stream, which flows proximally from aspiration port 734 towards a source of vacuum (not shown), the latter coupled to aspiration tube 730. Such an aspiration device enables convenient removal of unwanted materials, for instance, excess extraneous fluid (e.g., saline), resected tissue fragments, gaseous ablation by-products, and vapors, from the surgical field, thereby greatly improving visualization of the surgical field.

During a procedure, the rate of suction or aspiration via the aspiration device will generally depend on a number of factors including the diameters of aspiration port 734, aspiration lumen 732, and aspiration tube 730. In one embodiment, the diameter of one or more of aspiration port 734, aspiration lumen 732, and aspiration tube 730 is selected so as to limit the rate of aspiration to a level that allows for continuous aspiration (when needed) during use of probe 700, without deflating the body cavity or coelom. In one embodiment, the rate of aspiration or rate of flow of the aspiration stream may be controlled by an adjustable valve (not shown). As an example, such a valve may be conveniently coupled to aspiration tube 730, or connected between aspiration tube 730 and the vacuum source.

Figure 39D:
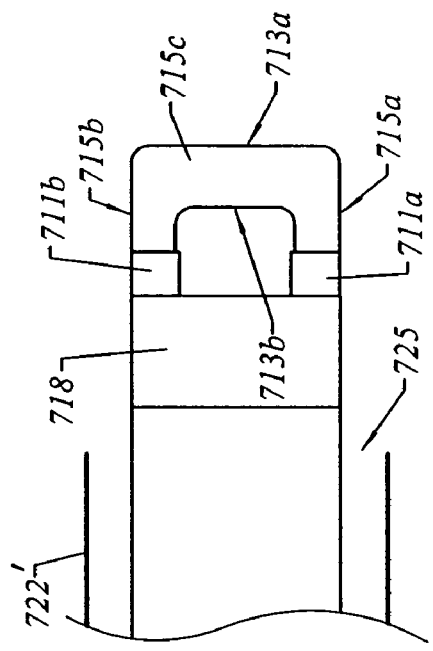
FIG. 39D shows detail of the distal portion of the probe of FIGS. 39A-C.
Figure 39C:
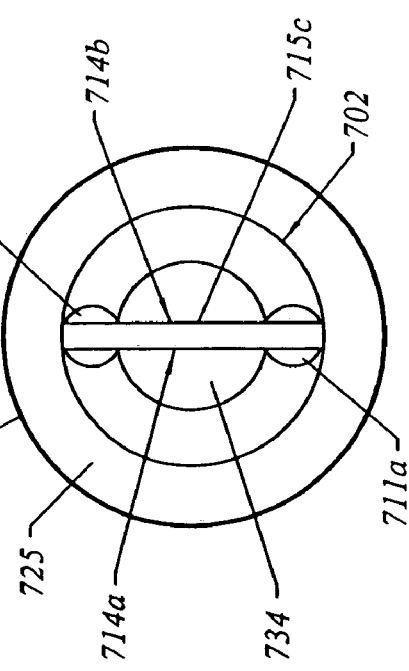

FIG. 39C is an end view of probe 700 taken along the lines 39C-39C of FIG. 39B. Active electrode 712 includes crosspiece 715c extending between first and second electrode arms 715a, 715b, respectively (FIG. 39D). Active electrode 712 further includes first and second blade sides 714a, 714b. In some embodiments, first and second blade sides 714a, 714b are adapted for engaging tissue that has been severed, and for coagulating the severed tissue. Crosspiece 715c at least partially spans aspiration port 734. Typically, active electrode 712 comprises a single metal blade, comprising a material such as platinum, tungsten, palladium, iridium, or titanium, or their alloys.

FIG. 39D shows detail of the distal portion of probe 700 of FIGS. 39A-C including blade active electrode 712. As shown, first and second electrode arms 715a, 715b are disposed on first and second electrode supports 711a, 711b, respectively. In an alternative embodiment, first and second electrode arms 715a, 715b may be disposed on a single annular electrode support having a substantially central void defining aspiration port 734. In one embodiment, active electrode 712 includes both a distal active edge 713a, and a proximal active edge 713b. Distal active edge 713a, in particular, is adapted for aggressively ablating tissue via molecular dissociation of tissue components and for severing tissue targeted for resection, transection, dissection, or other treatment.

FIG. 40A is a partial sectional view of an electrosurgical probe 700 according to another embodiment of the invention. Probe 700 of FIG. 40A generally includes shaft 702 and handle 704, together with a fluid delivery element, and an aspiration unit, essentially as for the embodiment described with reference to FIGS. 39A-D. In the interests of brevity these elements and features will not described in detail with reference to FIGS. 40A-C. The embodiment of FIG. 40A differs from other embodiments described herein in having an active electrode in the form of a plasma hook 712'. Hook 712' is in some respects analogous to plasma blade electrodes described hereinabove. For example, in one respect hook 712' is analogous to a truncated version of electrode 712 of the embodiment of FIGS. 39A-D in which one of arms 715a or 715b is omitted leaving one electrode arm affixed to crosspiece 715c. From a functional standpoint, hook 712' allows the operator (surgeon) to ablate tissue by drawing the instrument towards himself/herself. In this manner, greater control is exerted over the amount or extent of tissue removed or severed by probe 700. Hook 712' includes a first axial portion 712'a (FIG. 40C) in contact at its proximal end with electrode support 710. Hook 712' may further include a second portion 712'b extending from the distal portion of first axial portion 712'a. In some embodiments, second portion 712'b is arranged substantially orthogonal to first axial portion 712'a. In one embodiment, second portion 712'b may be structurally similar or analogous to crosspiece 715c of the embodiment of FIGS. 39A-D. Second portion 712'b at least partially spans aspiration port 734 (FIG. 40B). Electrode support 710 may comprise a refractory and electrically insulating material, such as a silicone rubber or the like, as described hereinabove.

FIG. 40B shows an end view of probe 700 taken along the lines 40B-40B of FIG. 40A. Hook 712' includes first and second blade sides 714a, 714b. Second portion 712'b extends at least partially across aspiration port 734. FIG. 40C shows detail of the distal end portion of probe 700 of FIGS. 40A, 40B, including hook 712'. Hook 712' includes a distal active edge 713a, a proximal active edge 713b, and an active tip 713c. Return electrode 718 is located proximal to electrode support 710. Upon application of a high frequency voltage between hook 712' and return electrode 718, a high current density may be generated at each of distal active edge 713a, proximal active edge 713b, and active tip 713c. Each of distal active edge 713a, proximal active edge 713b, and active tip 713c may be adapted for severing tissue via electrosurgical molecular dissociation of tissue components.

Figure 41A:
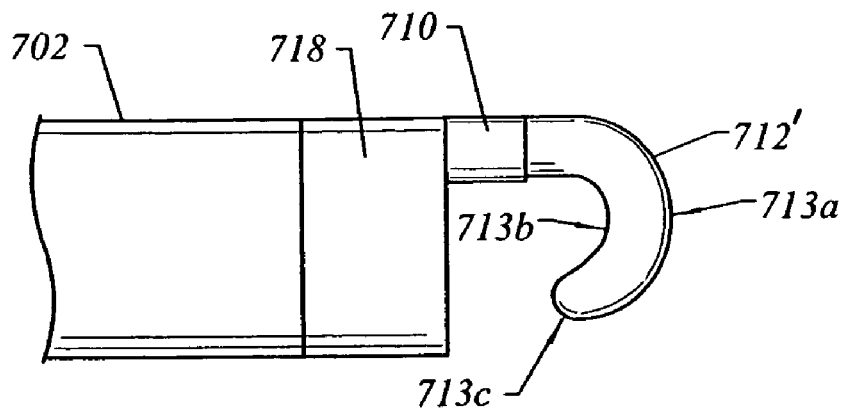
FIGS. 41A, 41B, and 41C each show detail of the distal portion of an electrosurgical probe, according to three different embodiments of the invention.
Figure 41B:
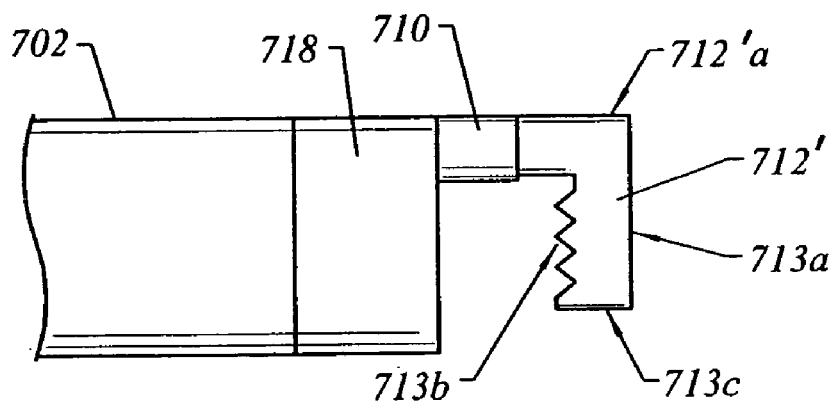
Figure 41C:
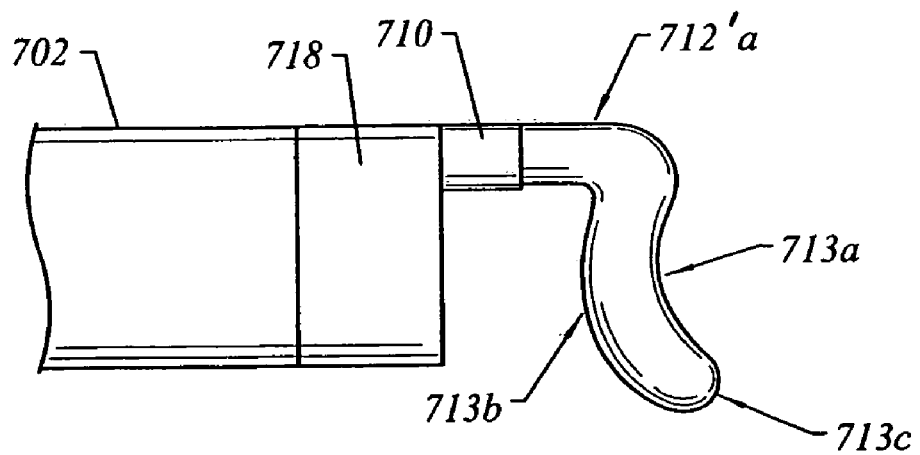

FIGS. 41A, 41B, and 41C each show detail of the distal end portion of an electrosurgical probe including a hook electrode 712', according to three different embodiments of the invention. In the embodiment of FIG. 41A, hook 712' is curved, having a convex distal edge 713a, and a concave proximal edge 713b. In the embodiment of FIG. 41B, proximal edge 713b includes serrations thereon. In an alternative embodiment (not shown), distal edge 713a, and/or active tip 713c may be similarly serrated. In the embodiment of FIG. 41C, hook 712' is curved, having a concave distal edge 713a, and a convex proximal edge 713b. According to various embodiments of probe 700, second portion 712'b may have a length which is less than, equal to, or greater than the diameter of shaft 702. In the latter case, second portion 712'b extends laterally beyond the exterior surface of shaft 702 (e.g., FIG. 41C). In each of the embodiments of FIGS. 41A-C, hook 712' typically comprises a single blade having first and second blade sides 714a, 714b (e.g., FIG. 40B). Hook 712' typically comprises a metal such as platinum, tungsten, palladium, iridium, or titanium, or their alloys.

Figure 42A:
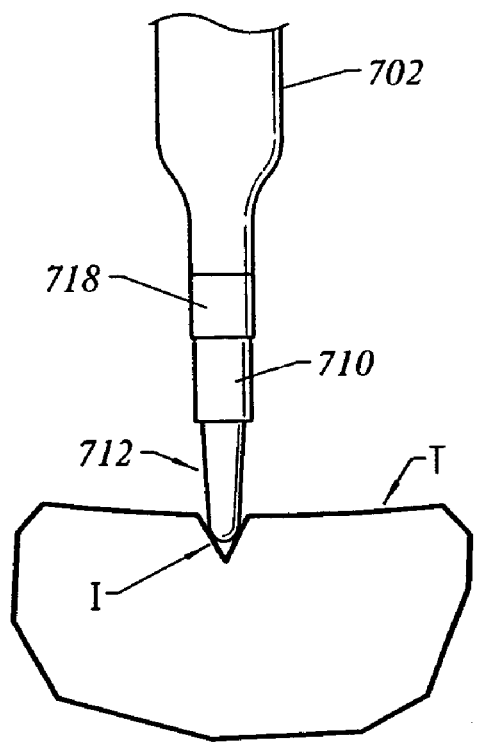
FIGS. 42A and 42B schematically represent a procedure for incising and coagulating tissue with an electrosurgical probe having a blade electrode, according to one embodiment of the invention.
Figure 42B:
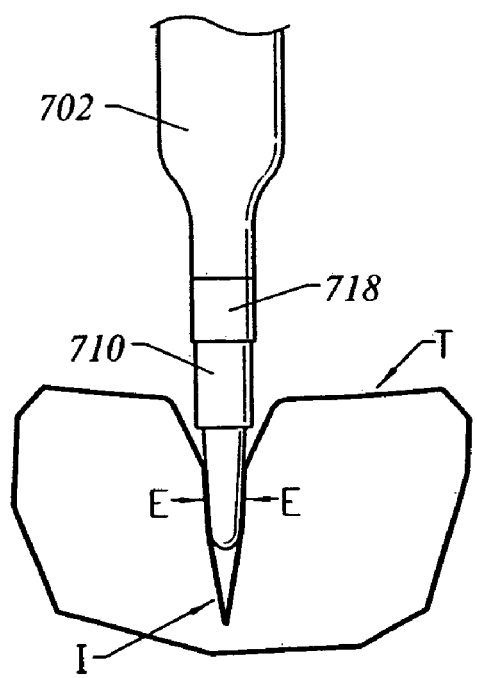

FIGS. 42A-B schematically represent a process during treatment of a patient with electrosurgical probe 700. Blade active electrode 712 is affixed to support 710 on shaft 702. Blade active electrode 712 includes active edge 713 and first and second blade sides, 714a, 714b (e.g., FIGS. 31A-B). Referring to FIG. 42A, active edge 713 forms an incision, I, in a target tissue, T, via localized molecular dissociation of tissue components upon application of a high frequency voltage between active electrode 712 and return electrode 718. (The localized molecular dissociation may be facilitated by the delivery of a suitable quantity of an electrically conductive fluid (e.g. isotonic saline) to form a current flow path between active electrode 712 and return electrode 718.) With reference to FIG. 42B, as the incision I is deepened within tissue T, first and second blade sides, 714a, 714b engage severed tissue in regions indicated by the arrows labeled E. In this way, the severed tissue is coagulated by first and second blade sides, 714a, 714b, thereby effecting hemostasis at the point of incision of the tissue.

Figure 43A:
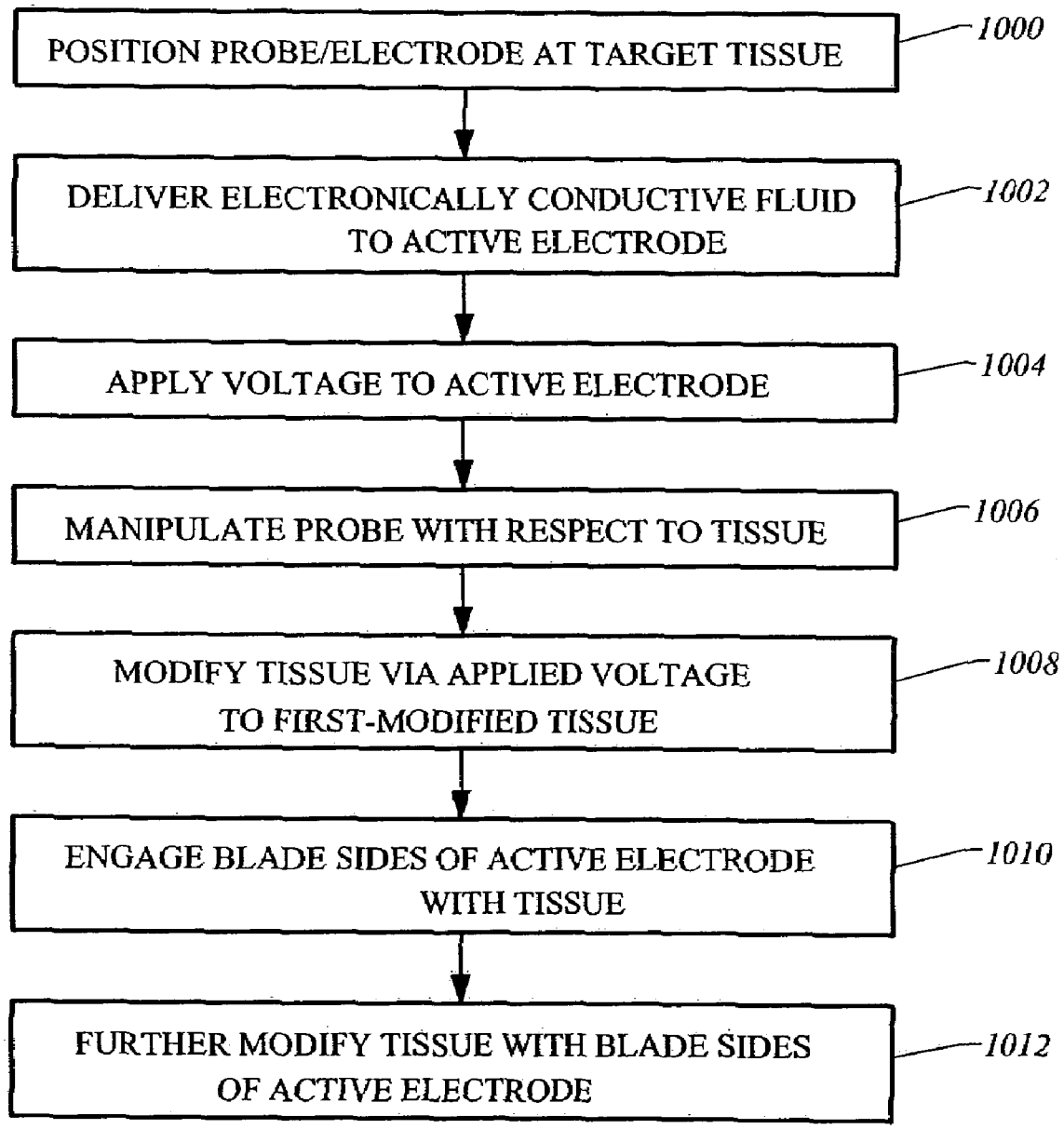
FIG. 43A schematically represents a number of steps involved in a method of treating a patient with an electrosurgical probe having a blade electrode, according to one embodiment of the invention.

FIG. 43A schematically represents a number of steps involved in a method of treating a patient with an electrosurgical probe, wherein step 1000 involves positioning the distal end of the probe adjacent to target tissue such that an active electrode of the probe is in contact with or in close proximity to the target tissue. In one embodiment, the active electrode is spaced a short distance from the target tissue, as described hereinabove. Typically, step 1000 involves positioning the probe such that an active edge of the active electrode makes contact with, or is in close proximity to, the target tissue. Step 1002 involves delivering an electrically conductive fluid to the distal end of the probe in the vicinity of the active electrode and the return electrode, such that the electrically conductive fluid forms a current flow path between the active electrode and the return electrode. The electrically conductive fluid may be delivered via an exterior tube disposed on the outside of the shaft (e.g., FIGS. 37A, 37B), or an outer sheath external to the shaft and forming an annular fluid delivery lumen (e.g., FIGS. 38A, 38B). The electrically conductive fluid may be a liquid, a gel, or a gas. Apart from providing an efficient current flow path between the active and return electrodes, a clear, colorless electrically conductive liquid, such as isotonic saline, exhibits the added advantage of increasing the visibility of the surgeon at the target site. However, in situations where there is an abundance of electrically conductive body fluids (e.g., blood, synovial fluid) already present at the target site, step 1002 may optionally be omitted.

Step 1004 involves applying a high frequency voltage between the active electrode and the return electrode sufficient to ablate or otherwise modify the target tissue via localized molecular dissociation of target tissue components. By delivering an appropriate high frequency voltage to a suitably configured probe, the target tissue can be incised, dissected, transected, contracted, or otherwise modified. In addition, the modified tissue can also be coagulated (e.g., FIG. 42B). The frequency of the applied voltage will generally be within the ranges cited hereinabove. For example, the frequency will typically range from about 5 kHz to 20 MHz, usually from about 30 kHz to 2.5 MHz, and often between about 100 kHz and 200 kHz. The root mean square (RMS) voltage that is applied in step 1004 is generally in the range of from about 5 volts RMS to 1000 volts RMS, more typically being in the range of from about 10 volts RMS to 500 volts RMS. The actual voltage applied may depend on a number of factors, including the size of the active electrode, the operating frequency, and the particular procedure or desired type of modification of the tissue (incision, contraction, etc.), as described hereinabove.

Step 1006 involves manipulating the probe with respect to the tissue at the target site. For example, the probe may be manipulated such that an active edge of a blade or hook electrode reciprocates with respect to the target tissue, such that the target tissue is severed, incised, or transected at the point of movement of the active edge by a process involving molecular dissociation of tissue components. In embodiments where the active electrode is in the form of a hook, step 1006 may involve engaging the hook against the target tissue and drawing the hook towards the operator in order to cut or sever the tissue. In this manner, the extent of cutting or severing can be precisely controlled. In one embodiment, step 1006 involves reciprocating an active edge in a direction parallel to a surface of the target tissue. Typically, step 1006 is performed concurrently with step 1004. Step 1002 may be performed at any stage during the procedure, and the rate of delivery of the electrically conductive fluid may be regulated by a suitable mechanism, such as a valve.

Step 1008 involves modifying the target tissue as a result of the high frequency voltage applied in step 1004. The target tissue may be modified in a variety of different ways, as referred to hereinabove. The type of tissue modification achieved depends, inter alia, on the voltage parameters of step 1004; the shape, size, and composition of the active electrode; and the manner in which the probe is manipulated by the surgeon in step 1006. At relatively high voltage levels, tissue components typically undergo localized molecular dissociation, whereby the target tissue can be dissected, incised, transected, etc. At a lower voltage, or at a lower current density on the active electrode surface, the target tissue can be contracted (e.g., by shrinkage of collagen fibers in the tissue), or a blood vessel can be coagulated. For example, in step 1010 the first and second blade sides of the active electrode may be engaged against a region of the target tissue which has been modified as a result of localized molecular dissociation of tissue components in step 1008. The first and second blade sides are substantially flat metal plates having lower current densities than the active edge. In this manner, the lower current densities of the first and second blade sides effect further modification (e.g., coagulation) of the previously modified (e.g., severed) target tissue (step 1012).

Figure 43B:
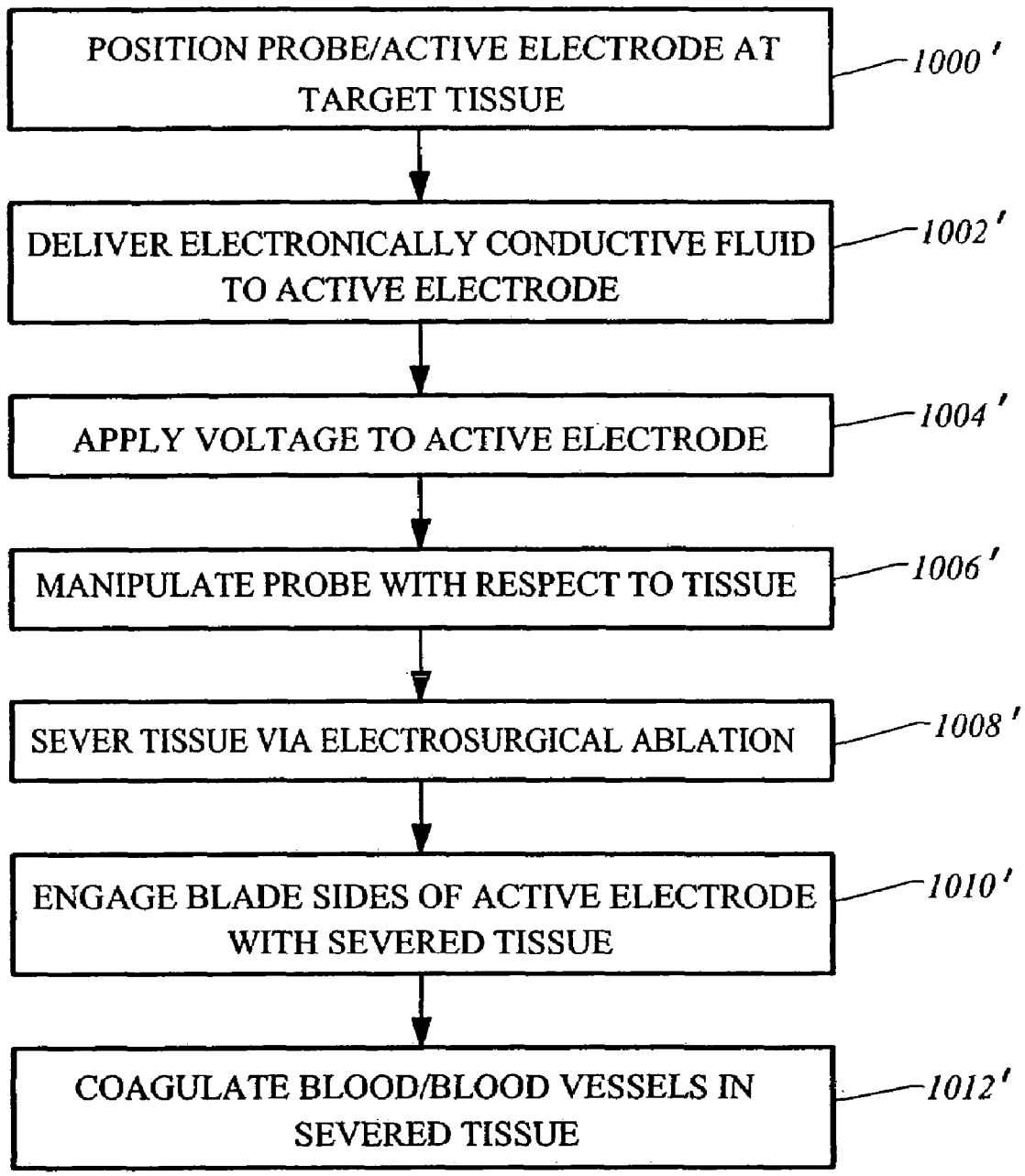
FIG. 43B schematically represents a number of steps involved in a method of concurrently severing and coagulating tissue, according to one embodiment of the invention.

FIG. 43B schematically represents a number of steps involved in a method of severing tissue with an electrosurgical probe via a process involving molecular dissociation of tissue components, and of coagulating the severed tissue with the same electrosurgical probe during a single procedure, according to one embodiment of the invention. The electrosurgical probe typically comprises an active electrode in the form of a single, substantially flat metal hook or blade having at least one active edge adapted for electrosurgically severing the tissue, and first and second blade sides adapted for effecting hemostasis of the severed tissue. Steps 1000' through 1006' are substantially the same or analogous to steps 1000 through 1006, as described hereinabove with reference to FIG. 43A. Step 1008' involves severing the target tissue via localized molecular dissociation of tissue components due to high current densities generated at the position of an active edge upon execution of step 1004'. Step 1010' involves engaging the first and second blade sides against the tissue severed in step 1008', whereby blood/blood vessels in the severed tissue are coagulated as a result of the relatively low current densities on the first and second blade sides (step 1012').

Figure 44:
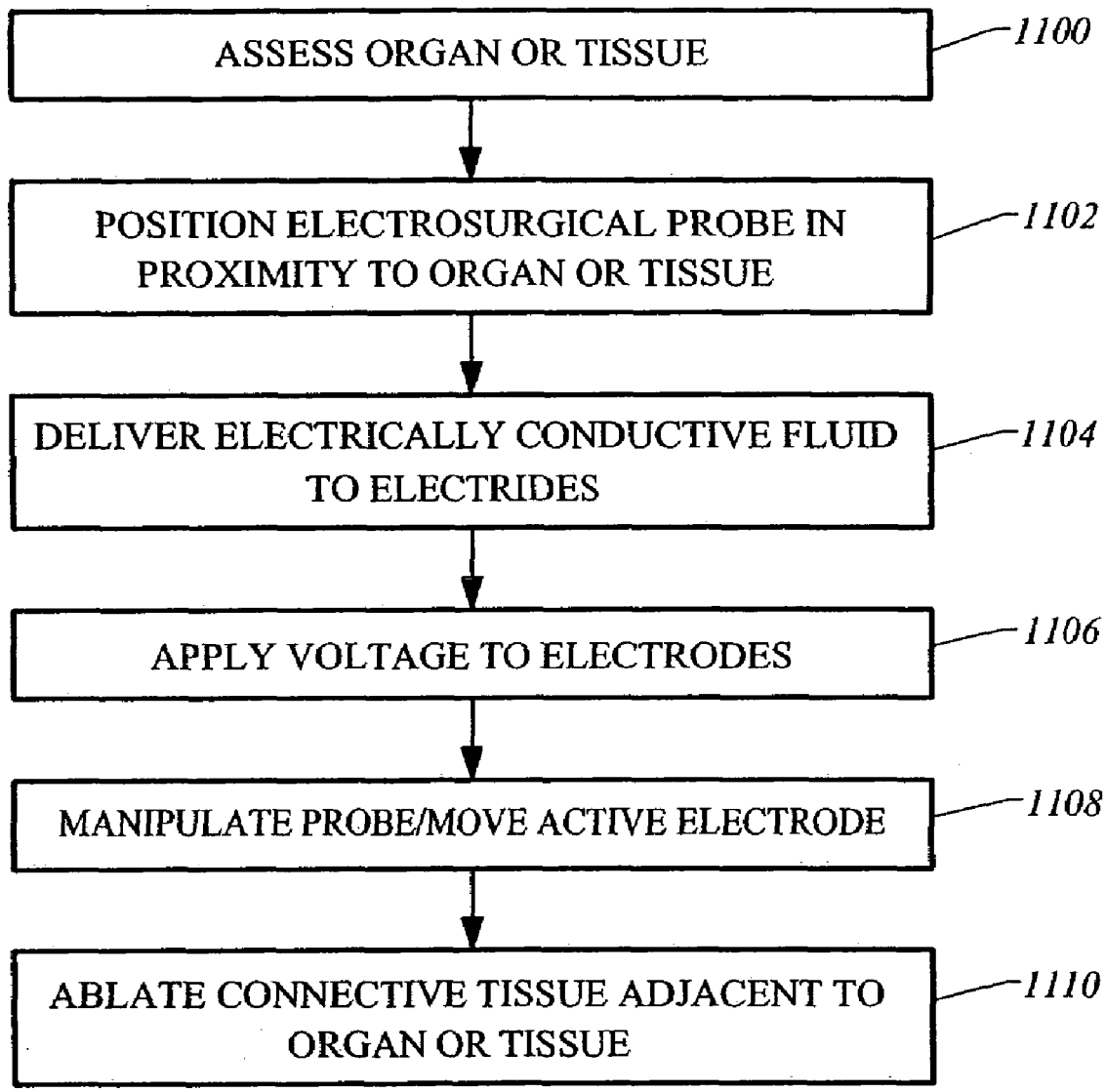
FIG. 44 schematically represents a number of steps involved in a method of dissecting a tissue or organ of a patient with an electrosurgical probe, according to another embodiment of the invention.

FIG. 44 schematically represents a number of steps involved in a method of dissecting a tissue or organ of a patient with an electrosurgical probe having a hook or blade active electrode, according to one embodiment of the invention, wherein step 1100 involves accessing an organ or tissue. Typically, accessing an organ or tissue in step 1100 involves incising an overlying tissue which conceals the organ or tissue to be dissected. As an example, in an open chest procedure involving a median sternotomy, the thoracic cavity is accessed by making a longitudinal incision though the sternum. Incising an overlying tissue in step 1100 may be performed generally according to the methods described with reference to FIG. 43A or 43B. Step 1102 involves positioning the distal end of the electrosurgical probe, and in particular an active edge of the hook or blade active electrode, in at least close proximity to connective tissue adjacent to the tissue or organ to be dissected. As an example, the connective tissue may be soft tissue, such as adipose tissue, or relatively hard tissue such as cartilage or bone. Optional step 1104 involves delivering an electrically conductive fluid to the distal end of the probe such that the electrically conductive fluid forms a current flow path between the active electrode and the return electrode, generally as described for step 1002, supra. Step 1106 involves applying a high frequency voltage between the active electrode and the return electrode, generally as described for step 1004, supra.

Depending on the type of procedure, e.g., the nature of the tissue or organ to be dissected, optional step 1108 may be performed, in which the probe is manipulated such that an active edge of the active electrode is moved with respect to the connective tissue adjacent to the tissue or organ to be dissected. Where the active electrode comprises a hook, the hook may be engaged against the connective tissue and drawn towards the operator of the probe to precisely control the degree of cutting or tissue removal. Step 1110 involves electrosurgically ablating, via molecular dissociation of connective tissue components, at least a portion of the connective tissue adjacent to the tissue or organ to be dissected. As an example, connective tissue adjacent to the internal mammary artery may be dissected by a process involving molecular dissociation of connective tissue components, in either an open-chest or a minimally invasive procedure, such that the IMA is substantially free from connective tissue over a portion of its length.

Figure 45A:
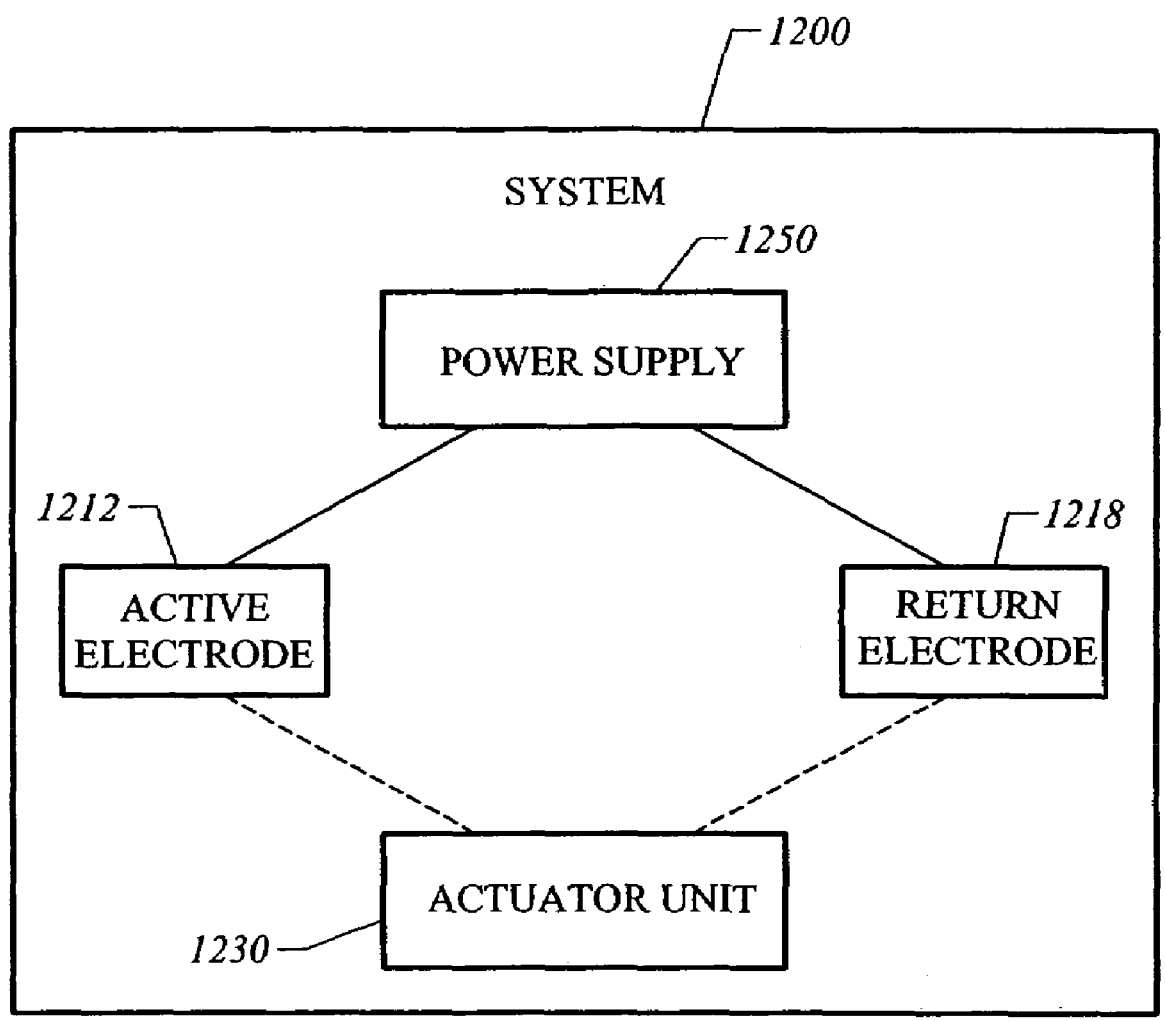
FIGS. 45A-C each schematically represent an electrosurgical system, according to three different embodiments of the invention.

FIG. 45A schematically represents an electrosurgical system 1200 of the instant invention, including a high frequency power supply 1250, coupled to an active electrode 1212 and a return electrode 1218, for applying a high frequency voltage between active electrode 1212 and return electrode 1218. System 1200 is adapted for operating in a sub-ablation mode (e.g., a coagulation mode) or in an ablation mode. In particular, system 1200 is adapted for coagulating or otherwise modifying a target tissue while operating in the sub-ablation mode; and for ablating or severing a target tissue while operating in the ablation mode. System 1200 further includes an actuator unit 1230 coupled to at least one of active electrode 1212 and return electrode 1218. At least one of active electrode 1212 and return electrode 1218 is moveable upon actuation of actuator unit 1230 by an operator of system 1200. Movement of at least one of active electrode 1212 and return electrode 1218, via actuator unit 1230, allows target tissue to be clamped by an electrosurgical probe during a surgical procedure and subsequently released, as will be discussed fully hereinbelow.

Figure 45B:
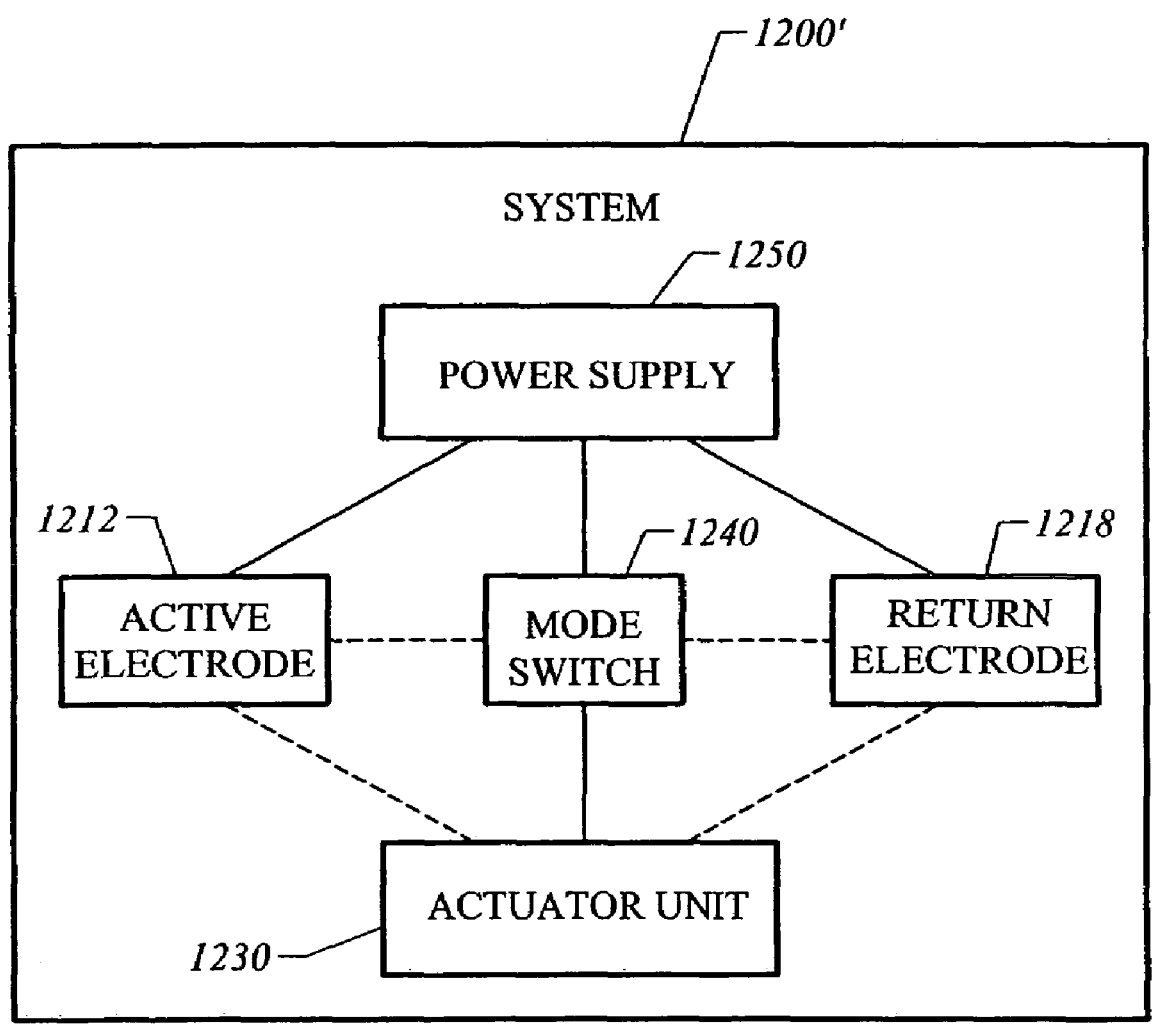

FIG. 45B is a box diagram which schematically represents an electrosurgical system 1200', according to another embodiment of the instant invention. System 1200' includes power supply 1250, active electrode 1212, return electrode 1218, and actuator unit 1230, as for system 1200 of FIG. 45A. System 1200' is similarly adapted for coagulating, severing, ablating, or otherwise modifying a target tissue. System 1200' further includes a mode switch 1240 coupled to both actuator unit 1230 and power supply 1250. Mode switch 1240 is for switching system 1200' between an ablation mode and a sub-ablation mode upon actuation of actuator unit 1230. Actuation of actuator unit 1230 enables movement of at least one of active electrode 1212 and return electrode 1218, and at the same time signals mode switch 1240 to switch system 1200' between the ablation and sub-ablation modes. In particular, actuator unit 1230 is adapted for shifting a probe (e.g., FIG. 47) between a closed configuration and an open configuration, such that the system operates in the sub-ablation mode when the probe is in the closed configuration, and the system operates in the ablation mode when the probe is in the open configuration.

In one embodiment, actuator unit 1230 provides a variable response, whereby the extent or degree of movement of active electrode 1212 and/or return electrode 1218 can be controlled. The ablation mode is characterized by a relatively high voltage applied by power supply 1250 between active electrode 1212 and return electrode 1218, whereas the sub-ablation mode is characterized by a relatively low voltage, as described in detail hereinabove. Typically, the ablation mode is characterized by a high frequency voltage in the range of from about 200 volts RMS to 1800 volts RMS, more typically from about 500 volts RMS to 1500 volts RMS. The sub-ablation mode is typically characterized by a high frequency voltage in the range of from about 10 volts RMS to 1000 volts RMS, more typically from about 50 volts RMS to 250 volts RMS. The ablation mode is adapted for ablating or severing target tissue via vaporization or, preferably, localized molecular dissociation of tissue components, while the sub-ablation mode is adapted for coagulating or contracting target tissue.

Figure 45C:
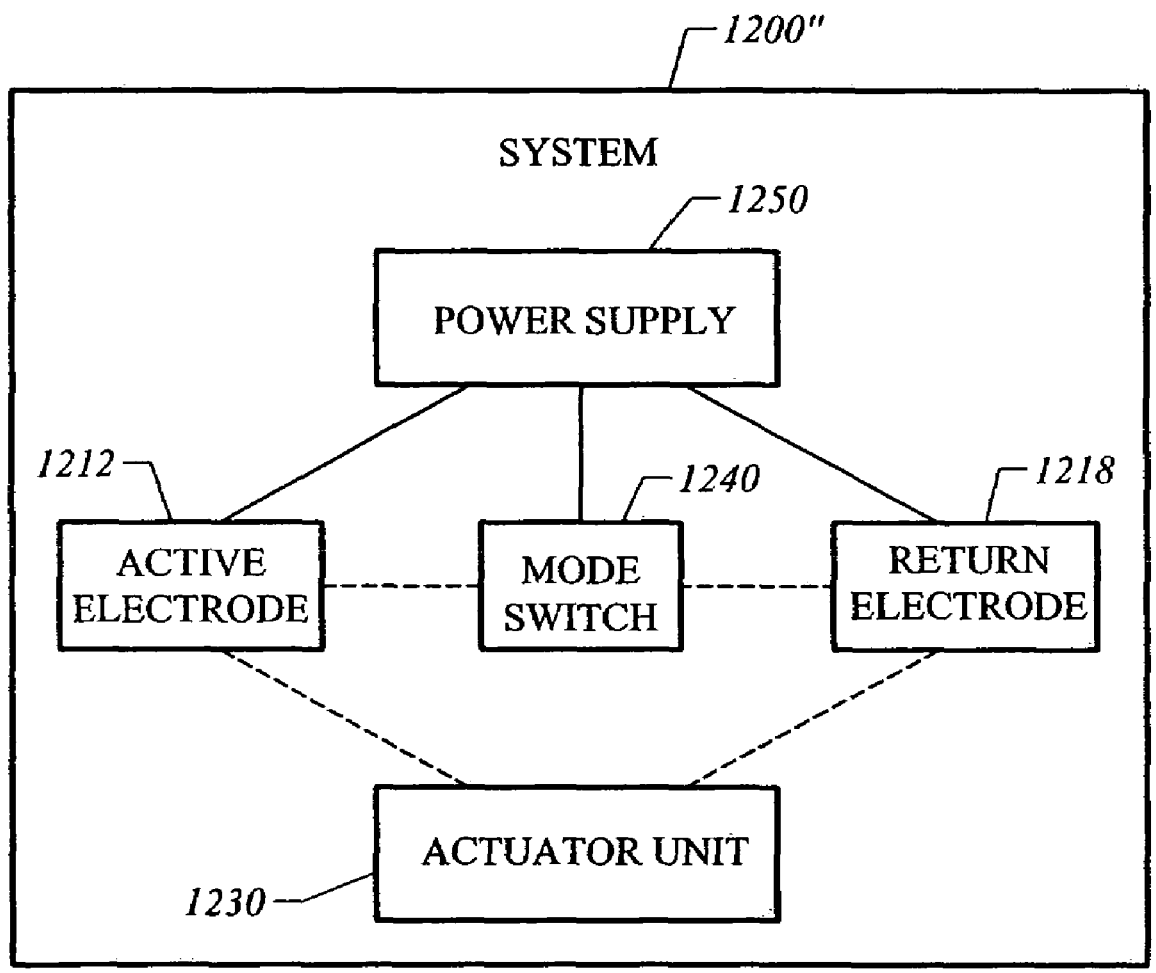

FIG. 45C is a box diagram which schematically represents an electrosurgical system 1200", according to another embodiment of the invention. System 1200" includes power supply 1250, active electrode 1212, return electrode 1218, and actuator unit 1230, as for system 1200 of FIG. 45A. System 1200" is also adapted for coagulating, severing, ablating, or otherwise modifying a target tissue while operating in the ablation mode or the sub-ablation mode, as for systems 1200, 1200'. In the embodiment of FIG. 45C, actuator unit 1230 is coupled to at least one of active electrode 1212 and return electrode 1218, wherein at least one of active electrode 1212 and return electrode 1218 is moveable between a first configuration and a second configuration. Actuation of actuator unit 1230 effects movement of active electrode 1212 and/or return electrode 1218 such that a probe 1201 (e.g., FIG. 47) of system 1200" is shifted between the first configuration and the second configuration.

System 1200" further includes mode switch 1240 coupled to power supply 1250 and to at least one of active electrode 1212 and return electrode 1218. Mode switch 1240 is for switching system 1200" between the ablation mode and the sub-ablation mode upon shifting of probe 1201 between the first configuration and the second configuration via actuation of actuator unit 1230. Thus in the embodiment of system 1200", actuation of actuator unit 1230 effects shifting of probe 1201 between the first and second configurations, essentially as for system 1200'. In contrast to system 1200', in the embodiment of system 1200", mode switch 1240 is responsive to movement of active electrode 1212 or movement of return electrode 1218, such that system 1200" is switched between the ablation and sub-ablation modes as the probe shifts between the first and second configuration. In both system 1200' and system 1200", mode switch 1240 may be integrated with actuator unit 1230, integrated with power supply 1250, or may be a separate device.

Figure 46:
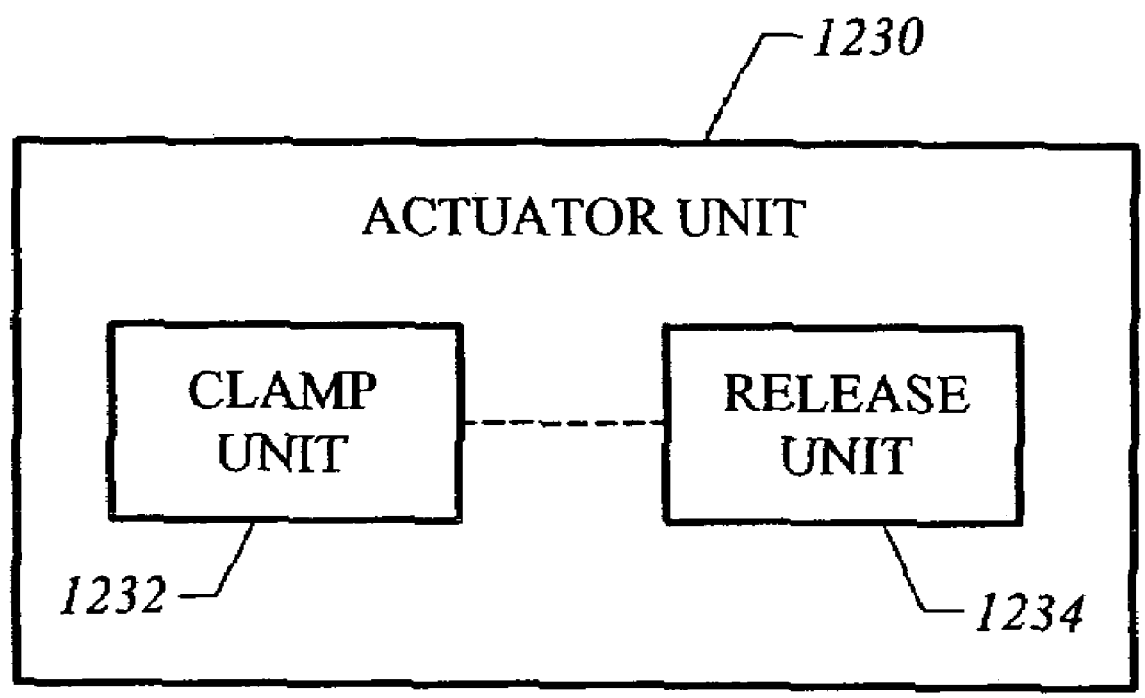
FIG. 46 is a block diagram representing an actuator unit of an electrosurgical system of the invention.

FIG. 46 is a block diagram representing actuator unit 1230 of an electrosurgical system of the invention, e.g., system 1200' or 1200" (FIGS. 45B, 45C). As shown, actuator unit 1230 includes a clamp unit 1232 and a release unit 1234. Clamp unit 1232 and release unit 1234 may be in communication with each other. Clamp unit 1232 is for urging an electrosurgical probe (e.g., probe 1201, FIG. 48C) towards a closed configuration such that a target tissue or portion of a blood vessel can be clamped by the probe during a surgical procedure.

Clamp unit 1232 may take various forms and may function in a number of different ways. For example, clamp unit 1232 may be manually operated by the exertion of a mechanical force on clamp unit 1232 by the surgeon, may take the form of a switch for turning on power to an electrically powered mechanism (not shown) for effecting clamping of tissue, or may take the form of a closure spring (also not shown) arranged so as to force the probe towards the closed configuration. Release unit 1234 may similarly take various forms, for example, release unit 1234 may be operated by the exertion, by the surgeon, of a counteracting mechanical force, via release unit 1234, sufficient to exceed the force exerted by a closure spring of clamp unit 1232. One or both of clamp unit 1232 and release unit 1234 may be hand- or foot-operated. For example, actuator unit 1230 may comprise one or more foot pedals, or actuator unit 1230 may be affixed to a handle of the probe (e.g., FIG. 47) for hand operation.

Figure 47:
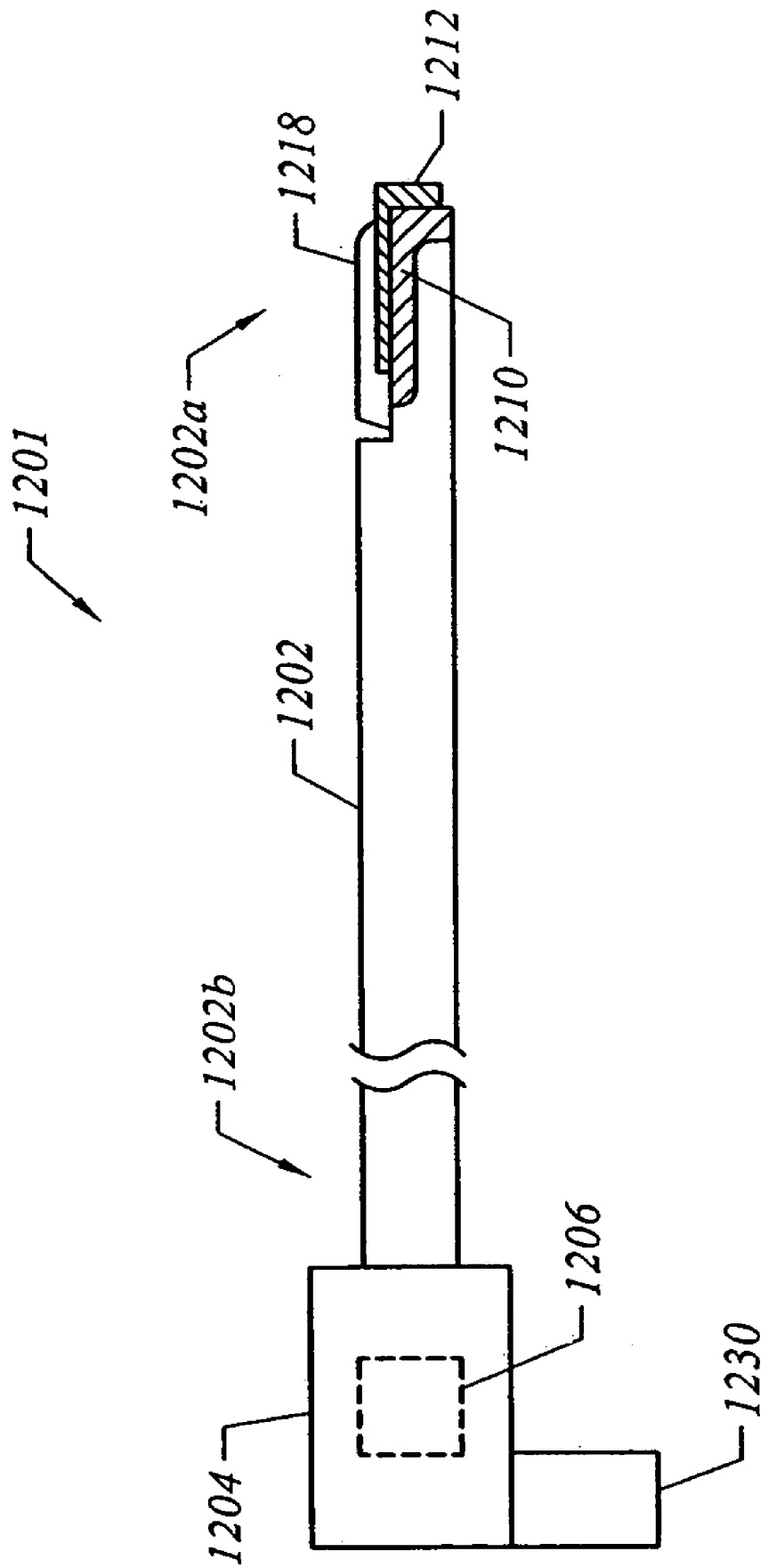
FIG. 47 schematically represents an electrosurgical probe as seen from the side, the probe including at least one moveable electrode, according to one embodiment of the instant invention.

FIG. 47 is a side view of an electrosurgical probe 1201 including a shaft 1202 having a shaft distal end portion 1202*a* and a shaft proximal end portion 1202*b*. An active electrode 1212 and a return electrode 1218 are disposed at shaft distal end portion 1202*a*. Active electrode 1212 is arranged on an electrically insulating electrode support 1210 for electrically isolating active electrode 1212 from other components of probe 1201. At least one of active electrode 1212 and return electrode 1218 is moveable such that shaft distal end portion 1202*a* can adopt a closed configuration or an open configuration. In one embodiment, active electrode 1212 and return electrode 1218 are in opposition to each other. Shaft distal end portion 1202*a* as shown in FIG. 47 is in the closed configuration, wherein active electrode 1212 and return electrode 1218 are parallel or substantially parallel to each other. In the open configuration, e.g., FIG. 48B, active and return electrodes 1212, 1218 are parted. In one embodiment, active electrode 1212 is fixed and return electrode 1218 takes the form of a moveable, or removeable, cowl (e.g., FIGS. 48B-E, 50A, 51).

A handle 1204 is affixed to shaft proximal end 1202*b*. Handle 1204 accommodates a connection block 1206, the latter in communication with active electrode 1212 and return electrode 1218 via electrode leads (not shown in FIG. 47). As shown, actuator unit 1230 is affixed to, or integral with, handle 1204. Actuator unit 1230 effects movement of one or both of active electrode 1212 and return electrode 1218, thereby enabling probe 1201 to be shifted between the closed configuration and the open configuration. Mode switch 1240 (FIGS. 45B, 45C) may be integral with actuator unit 1230 and/or handle 1204. Connection block 1206 provides for convenient coupling of active electrode 1212 and return electrode 1218 to power supply 1250. Mode switch 1240 may also be connected to power supply 1250 via connection block 1206. Actuator unit 1230 may also be coupled to active electrode 1212 and return electrode 1218 via connection block 1206. The components of probe 1201, including active electrode 1212 and electrode support 1210, may be constructed from the same or similar materials as described for the corresponding components of other probes of the invention, for example, probe 700 described with reference to FIGS. 30-41C, supra.

Figure 48A:
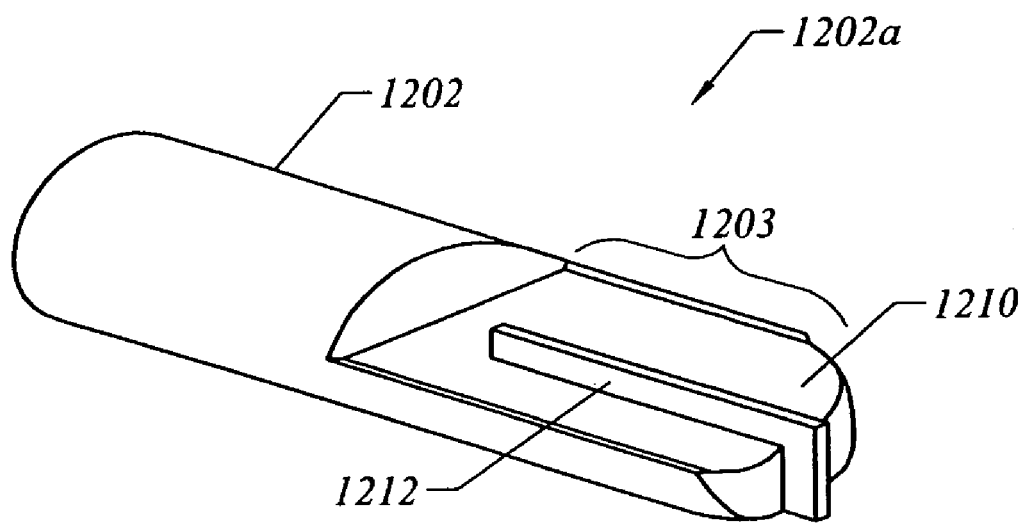
FIGS. 48A-E each show the distal end portion of an electrosurgical probe including a moveable return electrode, according to the invention.

FIGS. 48A-E each show detail of shaft distal end portion 1202*a* of an electrosurgical probe 1201 having a moveable return electrode 1218, according to one embodiment of the invention. FIG. 48A is a perspective view of shaft distal end portion 1202*a* in which return electrode 1218 is omitted for the sake of clarity. Electrode support 1210 is arranged on a recessed portion 1203 of shaft 1202. In the embodiment as shown, active electrode 1212 protrudes both laterally and terminally from electrode support 1210. Active electrode 1212 is adapted for coagulating and severing target tissue, as described in detail hereinbelow, during a broad range of surgical procedures. In one embodiment, active electrode 1212 may be in the form of a blade electrode, for example, having features and characteristics similar to those described hereinabove for active electrode 712 of probe 700 (e.g., FIGS. 30-41C).

Figure 48B:
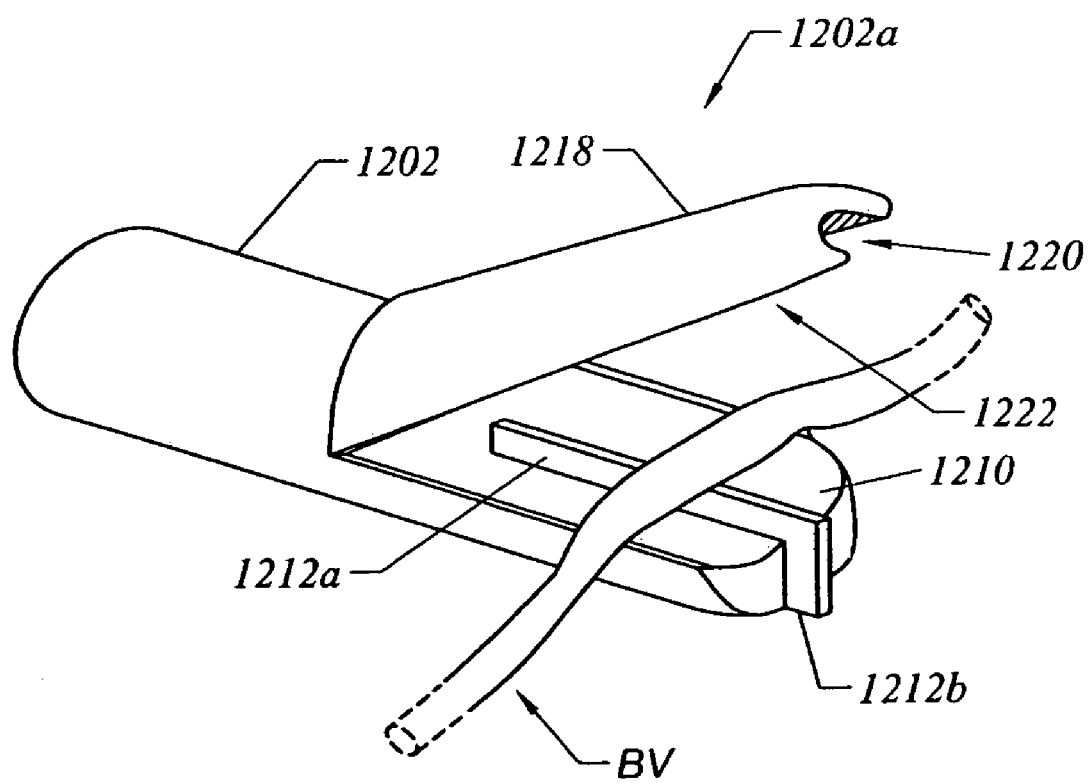
Figure 48C:
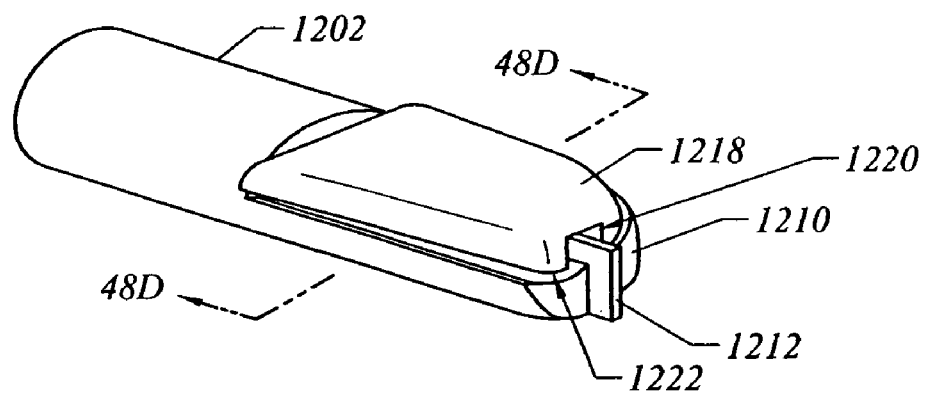

FIG. 48B is a perspective view of shaft distal end 1202*a* in an open or partially open configuration, in which return electrode 1218 is pivoted about its proximal end away from active electrode 1212. In the open configuration shaft distal end 1202*a* can accommodate at least a portion of a target tissue or blood vessel, BV, between active electrode 1212 and return electrode 1218. As shown, active electrode 1212 includes an elongate lateral portion 1212*a* and a distal terminal portion 1212*b*. Return electrode 1218 includes a return electrode perimeter 1222. In one embodiment, return electrode 1218 includes a distal notch 1220 for accommodating active electrode 1212. Notch 1220 prevents shorting between active electrode 1212 and return electrode 1218 when shaft distal end 1202*a* adopts the closed configuration (FIG. 48C). Return electrode 1218 may be forced into the open configuration and urged towards the closed configuration by actuator unit 1230 (e.g., FIG. 47).

FIG. 48C is a perspective view of shaft distal end 1202*a* in the closed configuration, in which return electrode 1218 lies parallel to active electrode 1212. Return electrode 1218 is in the form of a cowl, which largely conceals electrode lateral portion 1212*a*. Notch 1220 accommodates electrode lateral portion 1212*a* and allows return electrode 1218 to adopt a fully closed configuration. As shown, electrode terminal portion 1212*b* protrudes distally from the distal terminus of probe 1201. In the closed configuration, probe 1201 may be used in the sub-ablation mode for coagulating or contracting tissue. Alternatively, probe 1201 may also be used in the closed configuration in the ablation mode, for ablating or severing tissue with electrode terminal portion 1212*b*. In the open configuration, probe 1201 may be used in the ablation mode for ablating or severing tissue with one or both of lateral portion 1212*a* and terminal portion 1212*b*.

Figure 48D:
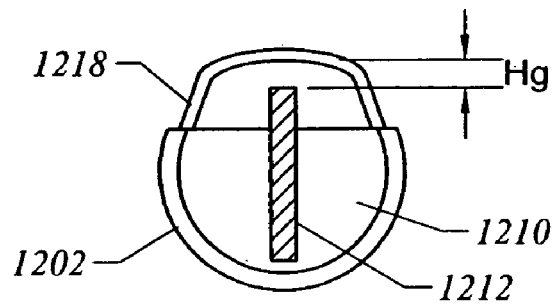
Figure 48E:
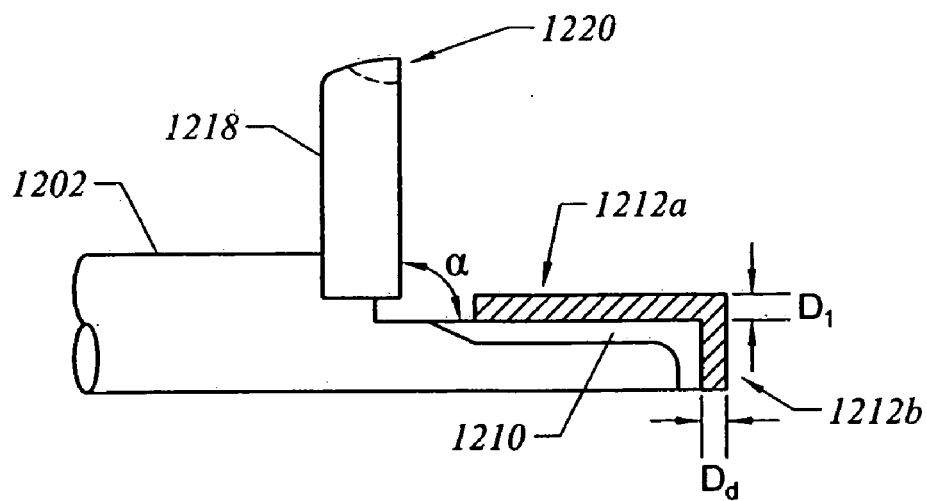

FIG. 48D is a sectional view of shaft distal end 1202*a* in the closed configuration, as taken along the lines 48D-48D of FIG. 48C. It can be seen that when shaft distal end 1202*a* is in the closed configuration, a gap $H_g$ exists between active electrode 1212 and the cowl of return electrode 1218. Typically, the gap $H_g$ is in the range of from about 0.05 mm to 10 mm, and more typically from about 1.0 mm to 10 mm. FIG. 48E is a side view of shaft distal end 1202*a* in the open or partially open configuration, in which return electrode 1218 is arranged at an angle ∀ to active electrode 1212. Typically, when shaft distal end 1202*a* is in the open or partially open configuration, angle ∀ is in the range of from about 30° to 180°, and more typically in the range of from about 45° to 180°. In one embodiment, the extent to which return electrode 1218 pivots away from active electrode 1212 can be controlled via actuator unit 1230. Typically, lateral portion 1212*a* protrudes laterally from electrode support 1210 by a distance $D_l$. Typically the distance $D_l$ is in the range of from about 0.05 mm to 10 mm, and more typically from about 0.5 mm to 8 mm. Electrode terminal portion 1212*b* typically protrudes distally from electrode support 1210 by a distance $D_d$, in the range of from about 0.2 mm to 10 mm, and more typically from about 0.5 mm to 10 mm.

Figure 49A:
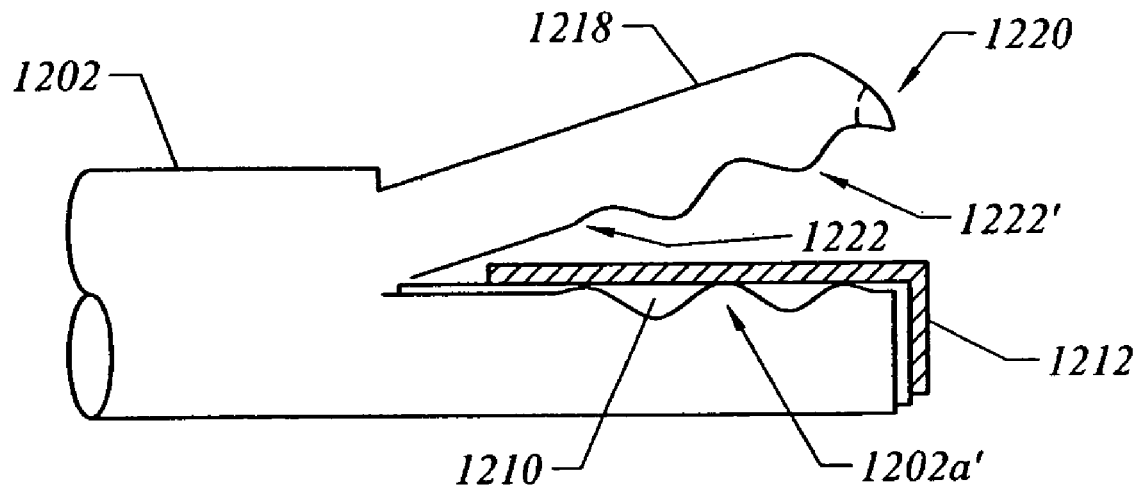
FIGS. 49A and 49B each show the distal end portion of an electrosurgical probe including a return electrode having an undulating perimeter, according to one embodiment of the invention.
Figure 49B:
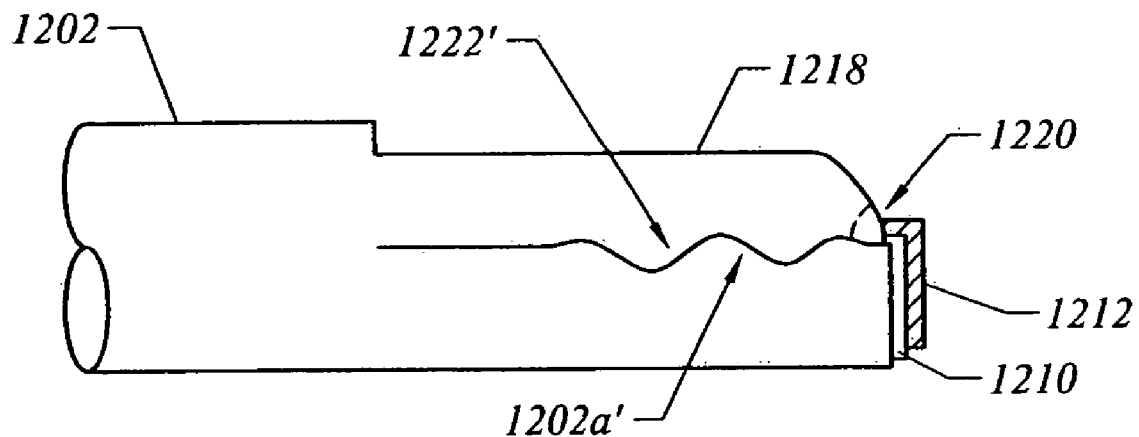

FIG. 49A shows shaft distal end portion 1202*a* of an electrosurgical probe 1201 in the open or partially open configuration, according to another embodiment of the invention. Perimeter 1222 of return electrode 1218 includes an undulating portion 1222'. A shaft undulating portion 1202*a*' of shaft distal end portion 1202*a* undulates in a manner complementary to perimeter undulating portion 1222'. As seen in FIG. 49B, when shaft distal end portion 1202*a* is in the closed configuration, the two undulating surfaces of portions 1222', 1202' are "interlocked." The presence of interlocking undulating surfaces of perimeter portion 1222' and shaft portion 1202' facilitates grasping and clamping of target tissue during use of probe 1201.

Figure 50A:
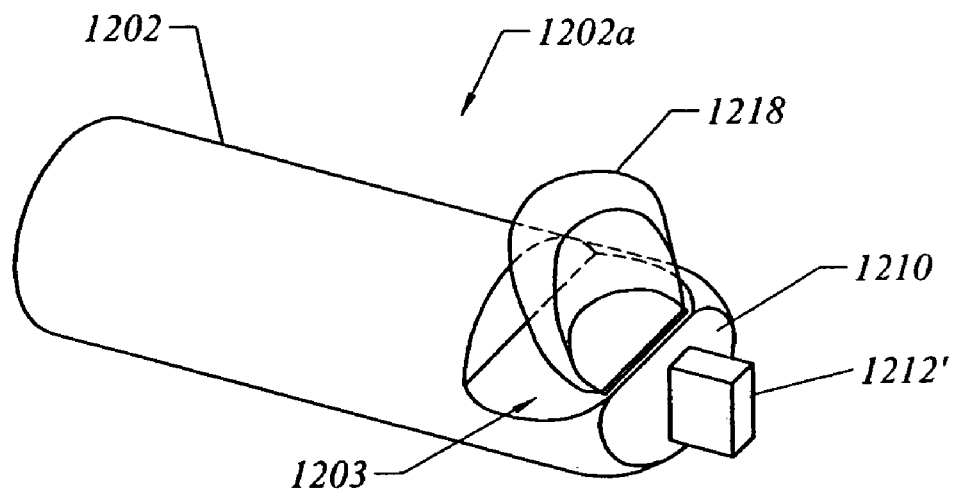
FIGS. 50A-C each show the distal end portion of an electrosurgical probe including a terminal active electrode and a moveable return electrode, according to another embodiment of the invention.
Figure 50B:
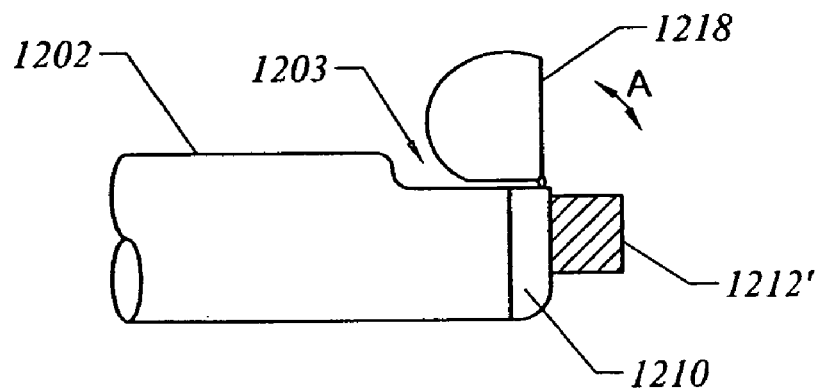
Figure 50C:
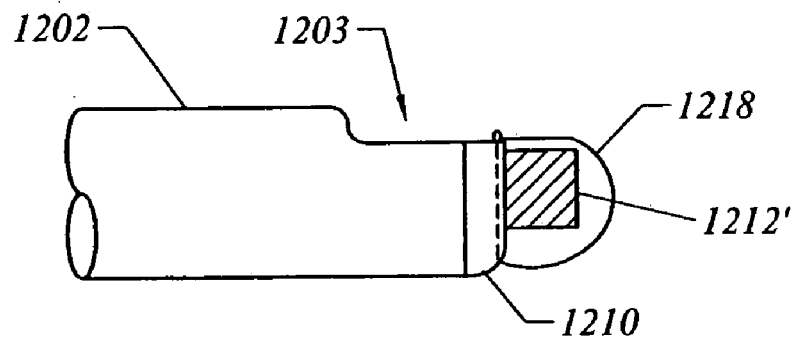

FIG. 50A is a perspective view of a shaft distal end portion 1202*a* of an electrosurgical probe 1201 including an active electrode 1212' mounted terminally on electrode support 1210, and a moveable return electrode 1218. The embodiment of FIGS. 50A-C differs from that described with reference to FIGS. 47-49B in that active electrode 1212' does not extend or protrude laterally on shaft distal end portion 1202*a*. FIGS. 50B and 50C are side views of shaft distal end portion 1202*a* in the open and closed configurations, respectively. In the embodiment of FIGS. 50A-C, return electrode 1218 is in the form of a quasi dome-shaped cowl mounted on recessed portion 1203 of shaft 1202. The pivotable nature of return electrode 1218 is indicated by the double-headed curved arrow marked A in FIG. 50B. As can be seen in FIG. 50C, when shaft distal end portion 1202*a* is in the closed configuration, a gap exists between active electrode 1212' and return electrode 1218. The presence of the gap prevents shorting between active electrode 1212' and return electrode 1218. Return electrode 1218 is adapted for clamping a target tissue or blood vessel against active electrode 1212'. In the closed configuration, with the probe operating in the sub-ablation mode, active electrode 1212' is adapted for coagulating or contracting target tissue clamped between active electrode 1212' and return electrode 1218. In the open configuration, with the probe operating in the ablation mode, active electrode 1212' is adapted for ablating or severing target tissue via localized molecular dissociation of tissue components.

Figure 51:
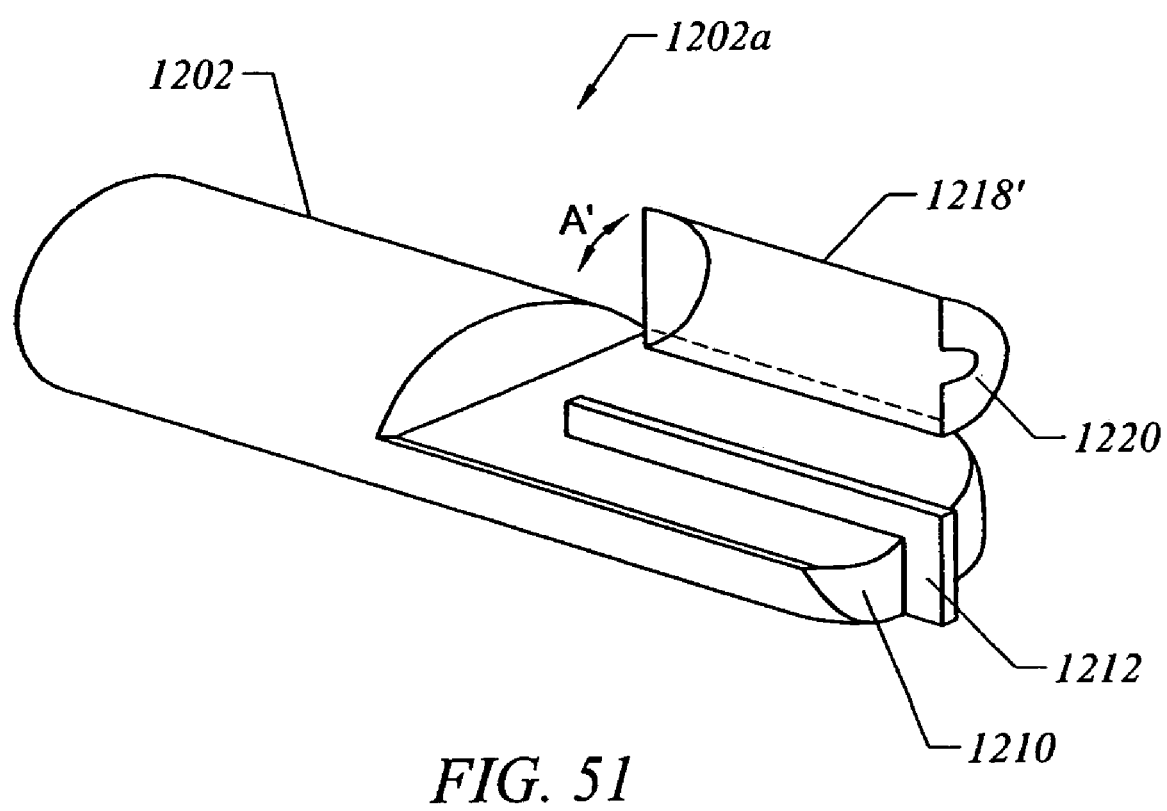
FIG. 51 shows the distal end portion of an electrosurgical probe including a moveable return electrode which is pivotable laterally, according to another embodiment of the invention.

With reference to FIG. 51 there is shown a shaft distal end portion 1202*a* of an electrosurgical probe 1201 according to another embodiment of the invention. A moveable return electrode 1218' comprises a cowl which is pivotable laterally, as indicated by the double-headed curved arrow marked A' in FIG. 51. Return electrode 1218' includes notch 1220 for accommodating active electrode 1212 when shaft distal end portion 1202*a* is in the closed configuration, thus preventing shorting between active and return electrodes 1212, 1218', respectively. Active electrode 1212 may comprise an elongate metal blade, which protrudes distally and laterally from electrode support 1210. While in the open configuration, shaft distal end portion 1202*a* may be positioned such that a target tissue lies between active electrode 1212 and return electrode 1218'. Return electrode 1218' may then be urged towards the closed configuration, e.g., by actuator unit 1230, whereby the target tissue is clamped between active electrode 1212 and return electrode 1218'. In use, active electrode 1212 and return electrode 1218' are coupled to opposite poles of a high frequency power supply for applying a high frequency voltage between active electrode 1212 and return electrode 1218'.

Figure 52A:
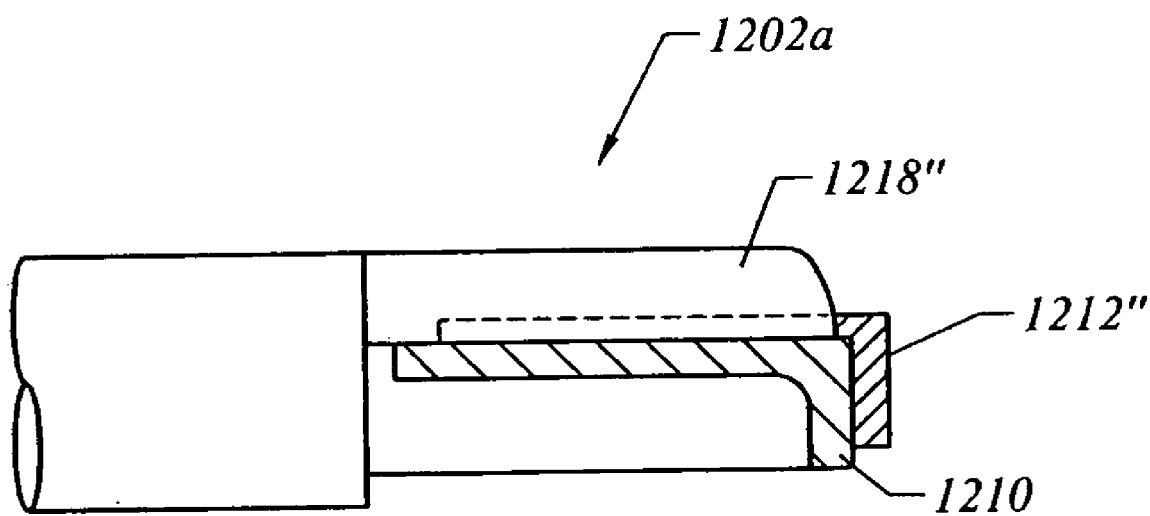
FIGS. 52A and 52B each show the distal end portion of an electrosurgical probe including a moveable active electrode, according to another embodiment of the invention.
Figure 52B:
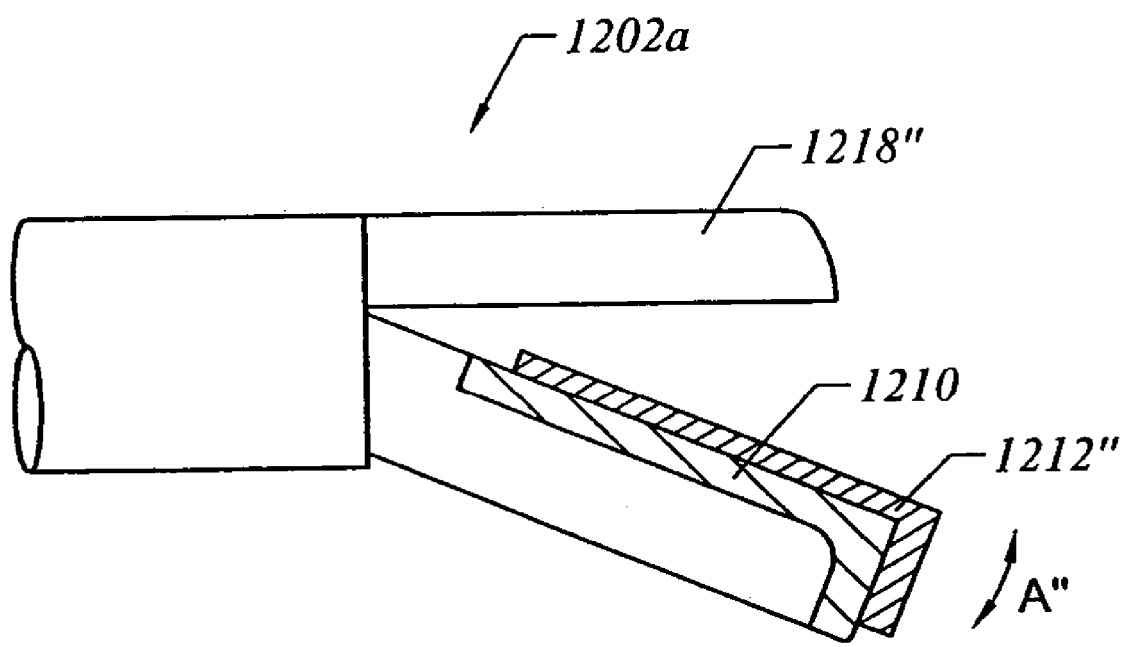

FIGS. 52A and 52B show a shaft distal end portion 1202*a* of an electrosurgical probe 1201 in the closed configuration, and in the open or partially open configurations, respectively, according to another embodiment of the invention. In the closed configuration shown in FIG. 52A, a fixed return electrode 1218" lies substantially parallel to a moveable active electrode 1212". Active electrode 1212" may be moved, e.g., via actuation of actuation unit 1230, such that shaft distal end portion 1202*a* is shifted to an open or partially open configuration, e.g., FIG. 52B. In one embodiment, active electrode 1212" may pivot about its proximal end, as indicated by the double-headed curved arrow marked A". When urged towards the closed configuration, active electrode 1212" combines with opposing return electrode 1218" to effectively clamp target tissue or a blood vessel at shaft distal end portion 1202*a*. Tissue clamped between active electrode 1212" and return electrode 1218" may be first coagulated by application of a first high frequency voltage from power supply 1250 operating in the sub-ablation/coagulation mode, and subsequently the coagulated tissue may be ablated by application of a second high frequency voltage from power supply 1250 operating in the ablation mode. Switching between the sub-ablation and ablation modes may be controlled by mode switch 1240. As described hereinabove, mode switch 1240 may be responsive either to actuation of actuator unit 1230 (e.g., system 1200', FIG. 45B), or to movement of active electrode 1212" (e.g., resulting in a change in configuration of shaft distal end 1202*a*).

Figure 53A:
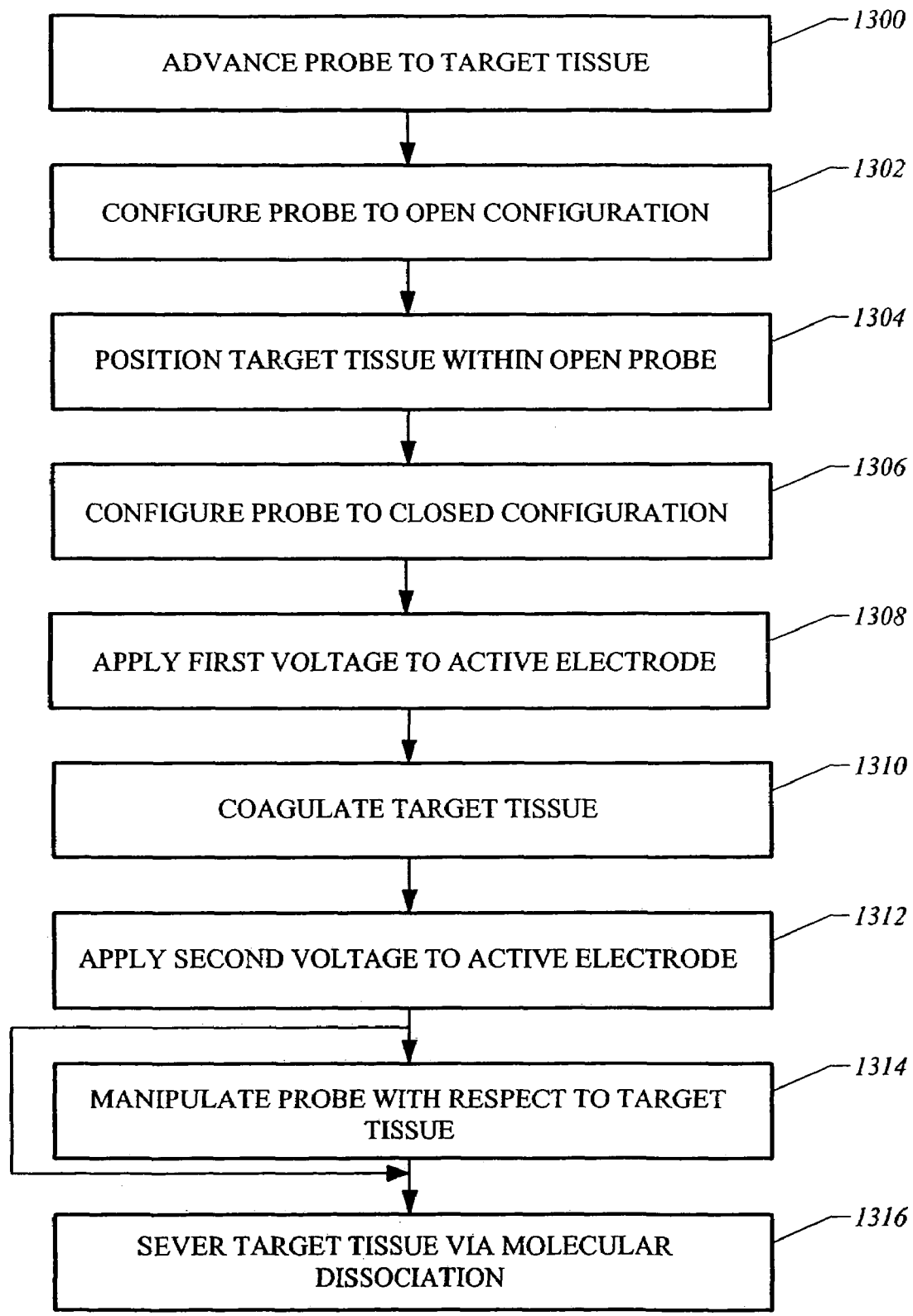
FIG. 53A schematically represents a number of steps involved in a method of coagulating and severing a target tissue with an electrosurgical probe, according to one embodiment of the invention.

FIG. 53A schematically represents a number of steps involved in a method of coagulating and severing a target tissue with an electrosurgical probe, wherein step 1300 involves advancing the electrosurgical probe towards the target tissue. The probe typically includes opposing active and return electrodes arranged at a shaft distal end portion, wherein at least one of the active and return electrodes is moveable such that the shaft distal end portion can adopt an open configuration or a closed configuration. Step 1302 involves configuring the probe such that the shaft distal end is in the open or partially open configuration. Typically, in the open configuration, the probe can accommodate at least a portion of a target tissue and/or a portion of a blood vessel between the active and return electrodes. The probe may be configured to the open configuration via an actuator unit, for example, by actuation of a release unit of the actuator unit.

Step 1304 involves positioning the target tissue between the active and return electrodes. Step 1306 involves configuring the probe such that the shaft distal end is in the closed or partially closed configuration. For example, the active electrode and/or the return electrode may be urged towards the closed configuration via actuation of a clamp unit of the actuator unit. In this manner, the target tissue, e.g., a portion of a blood vessel, may be clamped between the active electrode and the return electrode. The clamp unit and the release unit may be hand- or foot-operated by the surgeon, as described hereinabove, e.g., with reference to FIG. 46.

Step 1308 involves applying a first high frequency voltage between the active electrode and the return electrode. Typically, the first high frequency voltage is sufficient to coagulate the target tissue, but insufficient to ablate the tissue via molecular dissociation of tissue components, i.e., the system is operating in the sub-ablation mode. Step 1310 involves coagulating the target tissue or blood vessel as a result of the voltage applied in step 1308. Thereafter, step 1312 involves applying a second high frequency voltage between the active electrode and the return electrode sufficient to ablate, or Coblate, the tissue via molecular dissociation of tissue components. That is to say, during step 1308 the system is operating in the ablation mode. Voltage levels characteristic of the sub-ablation mode and the ablation mode are presented hereinabove.

According to one aspect of the invention, during a procedure the electrosurgical system may be conveniently switched, "automatically," between the sub-ablation and ablation modes via a mode switch (FIGS. 45B-C). In one embodiment of the invention (FIG. 45B), the mode switch may be directly responsive to actuation of the actuator unit, such that the system is automatically switched to the ablation mode when the release unit is actuated to force the probe into the open configuration. Similarly, the system may be automatically switched to the sub-ablation mode when the clamp unit is actuated to urge the probe into the closed configuration. According to an alternative embodiment (FIG. 45C), the mode switch may be responsive to movement of a moveable electrode (either a moveable active electrode (FIGS. 52A-B) or a moveable return electrode (FIGS. 48B-D), such that the system is automatically switched to the ablation mode when the at least one moveable electrode is moved into the open configuration, and/or the system is automatically switched to the sub-ablation mode when the at least one moveable electrode is moved into the closed configuration. Optional step 1314 involves manipulating the probe during step 1312, such that the active electrode is engaged and moved against the coagulated target tissue. As a result of application of the second high frequency voltage the coagulated target tissue is severed due to the localized molecular dissociation of tissue components, step 1316.

Figure 53B:
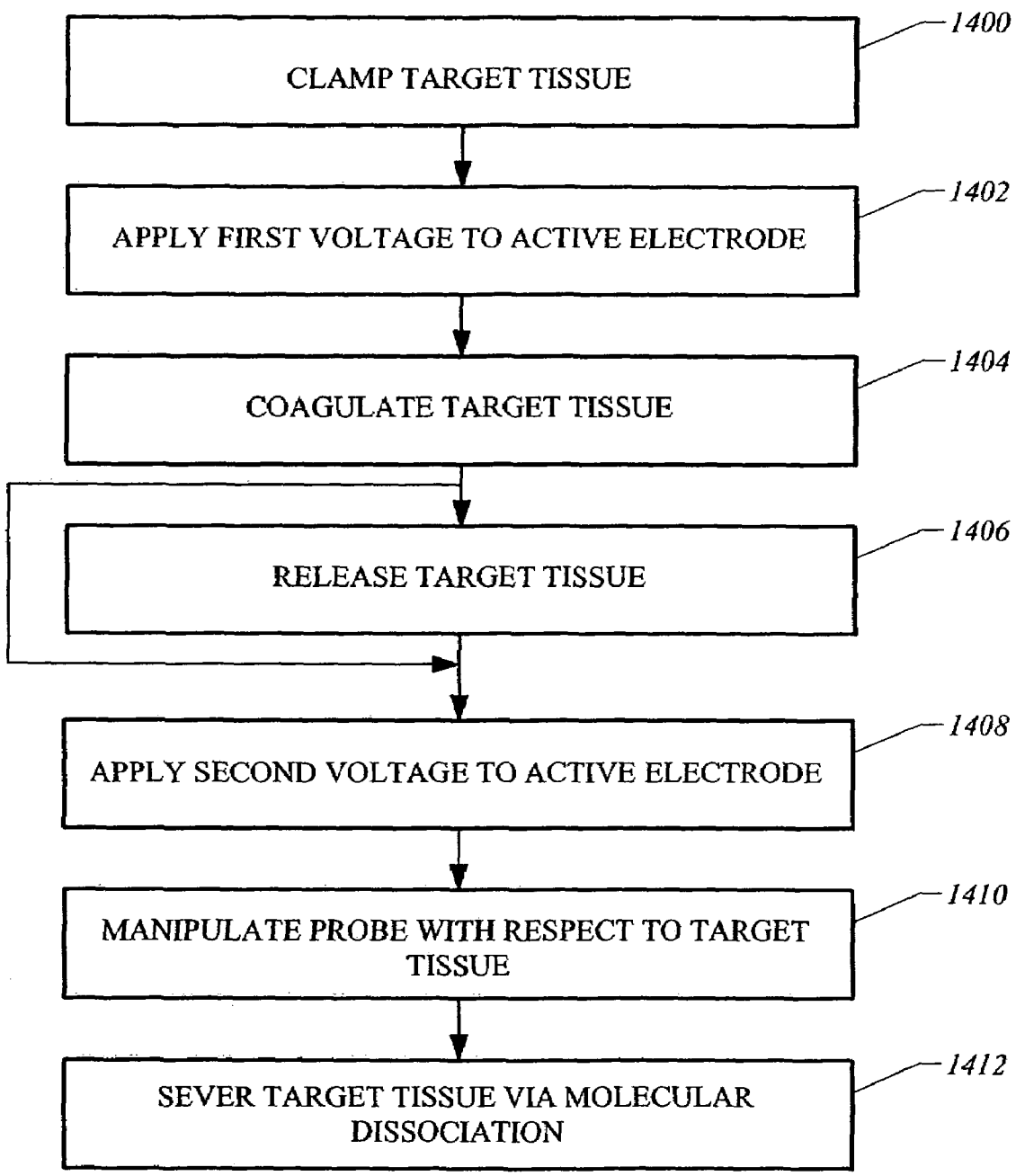
FIG. 53B schematically represents a number of steps involved in a method of modifying and ablating a target tissue, according to yet another embodiment of the invention.

FIG. 53B schematically represents a number of steps involved in a method of modifying and/or ablating a target tissue with an electrosurgical system including a probe and a high frequency power supply, wherein step 1400 involves clamping a target tissue. In one aspect, the target tissue may comprise a portion of a blood vessel. For example, during resection of a connective tissue via electrosurgical ablation, the surgeon may encounter one or more substantial blood vessels which require coagulation before proceeding with the resection. Upon encountering such a blood vessel, the surgeon may coagulate the blood vessel, as follows. With the electric power from the power supply turned off, or with the electrosurgical system operating in a sub-ablation mode, the blood vessel may be clamped between the active and return electrodes, essentially as described hereinabove, e.g., with reference to FIG. 53A. Thereafter, with the electrosurgical system in the sub-ablation mode, step 1402 involves applying a first high frequency voltage between the active electrode and the return electrode, wherein the first high frequency voltage is effective in coagulating the blood vessel, but insufficient to ablate the blood vessel. As used in this context, the term "ablate" refers to electrosurgical ablation via molecular dissociation of tissue components at relatively low temperatures (typically in the range of about 45° C. to 90° C.).

While the blood vessel or other target tissue remains clamped by the probe, step 1404 involves coagulating the clamped blood vessel or other target tissue as a result of the first high frequency voltage applied in step 1402. After coagulation has occurred to a suitable extent, optional step 1406 involves releasing or unclamping the clamped vessel or other target tissue from the probe. Typically, releasing the target tissue involves configuring the probe to the open or partially open configuration, e.g., via a release unit of the electrosurgical system (FIG. 46). Thereafter, the electrosurgical system is switched to the ablation mode, and a second, higher voltage is applied between the active electrode and the return electrode in step 1408, wherein the second voltage is sufficient to ablate the coagulated tissue via molecular dissociation of tissue components.

With the probe in the open configuration, the probe may be manipulated by the surgeon such that the active electrode is engaged and moved against the coagulated tissue, step 1410. Step 1412 involves severing the coagulated tissue via localized molecular dissociation of tissue components. In the example cited above, namely wherein a blood vessel is encountered during resection of a tissue, after the blood vessel has been coagulated and severed according to steps 1400 through 1412, with the system operating in the ablation mode, the surgeon may then resume resection via molecular dissociation of tissue components. During resection of tissue such as connective tissue, the probe will typically be in the open configuration (e.g., FIG. 48E). However, in embodiments of probe 1201 in which the active electrode protrudes both laterally and distally from the electrode support (e.g., FIGS. 48A-C), the probe may also be used in the closed configuration for ablation or modification of target tissue.

It is to be understood that the electrosurgical apparatus of the invention is by no means limited to those methods described with reference to FIGS. 42A-44, or FIGS. 53A-B. Thus, as stated hereinabove, embodiments of an electrosurgical probe are applicable to a broad range of surgical procedures, such as ablation, incision, contraction, coagulation, or other modification of: connective tissue, including adipose tissue, cartilage, and bone; dermal tissue; vascular tissues and organs, including arteries and veins; and tissues of the shoulder, knee, and other joints. Thus, while the exemplary embodiments of the present invention have been described in detail, by way of example and for clarity of understanding, a variety of changes, adaptations, and modifications will be apparent to those of skill in the art. Therefore, the scope of the present invention is limited solely by the appended claims.

What is claimed is:

1. An electrosurgical system for ablating or modifying tissue at a target site, comprising:
   a shaft having a shaft distal end portion and a shaft proximal end portion, the shaft distal end portion having an active electrode and an opposing return electrode in pivotable relationship with said active electrode such that said electrodes have an open configuration or a closed configuration and wherein the closed configuration is adapted to clamp and hold tissue between the first and second electrode;
   a voltage supply in electrical communication with said active and return electrode;
   an electrically conductive fluid supply assembly containing electrically conductive fluid having an electrical conductivity equal to or greater than isotonic saline, wherein the electrically conductive fluid supply assembly is adapted to supply electrically conductive fluid to the target site such that a current flow path is present through the electrically conductive fluid between the active and the return electrode when a first high frequency voltage is applied between the active electrode and the return electrode;
   a mode switch for switching the system between a coagulation mode and an ablation mode, wherein the mode switch is responsive to a shift in configuration of the shaft distal end portion.

2. The system of claim 1, wherein the closed configuration is adapted for coagulating a target tissue.

3. The system of claim 1, wherein the first high frequency voltage is sufficient to ablate the target tissue via localized molecular dissociation of target tissue components.

4. The system of claim 1 further comprising an electrode support supporting the active electrode.

5. The system of claim 4, wherein the closed configuration is adapted for coagulating a target tissue.

6. The system of claim 1 wherein the return electrode comprises a notch adapted to accommodate the active electrode.

7. The system of claim 1 wherein the active electrode comprises an elongate lateral portion.

8. The system of claim 7 wherein the active electrode comprises a distal terminal portion.

9. The system of claim 1 comprising an actuator unit adapted to force the active electrode and the return electrode toward the closed configuration.

10. The system of claim 1 wherein the active electrode is parallel to the return electrode in the closed configuration.

11. The system of claim 1 wherein the return electrode comprises a cowl.

12. The system of claim 1 wherein in the open configuration the active electrode is disposed at an angle with respect to the return electrode.

13. An electrosurgical system for ablating or modifying tissue at a target site, comprising:
- a shaft having a shaft distal end portion and a shaft proximal end portion, the shaft distal end portion having an active electrode and an opposing return electrode in pivotable relationship with said active electrode such that said electrodes have an open configuration or a closed configuration and wherein the closed configuration is adapted to clamp and hold tissue between the first and second electrode;
- a voltage supply in electrical communication with said active and return electrode; and
- a mode switch for switching the system between a coagulation mode and an ablation mode, wherein the mode switch is responsive to a shift in configuration of the shaft distal end portion.

14. The system of claim 13, further comprising an electrode support supporting the active electrode.

15. The system of claim 13 wherein the return electrode comprises a notch adapted to accommodate the active electrode.

16. The system of claim 13 wherein the active electrode comprises an elongate lateral portion.

17. The system of claim 16 wherein the active electrode comprises a distal terminal portion.

18. The system of claim 13 comprising an actuator unit adapted to force the active electrode and the return electrode toward the closed configuration.

19. The system of claim 13 wherein the active electrode is substantially parallel to the return electrode in the closed configuration.

20. The system of claim 13 wherein the return electrode comprises a cowl.

21. The system of claim 13 wherein in the open configuration the active electrode is disposed at an angle with respect to the return electrode.

* * * * *